(12) United States Patent
Travis et al.

(10) Patent No.: US 11,549,953 B2
(45) Date of Patent: Jan. 10, 2023

(54) IMMOBILIZED PROTEIN SYSTEM FOR RAPID AND ENHANCED MULTIPLEXED DIAGNOSTICS

(71) Applicant: CORNELL UNIVERSITY, Ithaca, NY (US)

(72) Inventors: Alexander J. A. Travis, Ithaca, NY (US); Roy Cohen, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 767 days.

(21) Appl. No.: 15/373,020

(22) Filed: Dec. 8, 2016

(65) Prior Publication Data

US 2017/0089926 A1   Mar. 30, 2017

Related U.S. Application Data

(62) Division of application No. 14/125,221, filed as application No. PCT/US2012/041886 on Jun. 11, 2012, now Pat. No. 9,547,014.

(60) Provisional application No. 61/495,804, filed on Jun. 10, 2011.

(51) Int. Cl.
| | |
|---|---|
| G01N 33/68 | (2006.01) |
| C12Q 1/25 | (2006.01) |
| C12Q 1/42 | (2006.01) |
| C12Q 1/48 | (2006.01) |
| C12N 11/18 | (2006.01) |
| C12Q 1/32 | (2006.01) |
| C12Q 1/66 | (2006.01) |

(52) U.S. Cl.
CPC ......... *G01N 33/6896* (2013.01); *C12N 11/18* (2013.01); *C12Q 1/25* (2013.01); *C12Q 1/32* (2013.01); *C12Q 1/42* (2013.01); *C12Q 1/485* (2013.01); *C12Q 1/66* (2013.01); *G01N 2800/2814* (2013.01); *G01N 2800/2821* (2013.01); *G01N 2800/2835* (2013.01); *G01N 2800/2857* (2013.01); *G01N 2800/2871* (2013.01)

(58) Field of Classification Search
CPC ....... G01N 33/6896; G01N 2800/2814; G01N 2800/2871; C12Q 1/32
See application file for complete search history.

(56) References Cited

U.S. PATENT DOCUMENTS

| | | |
|---|---|---|
| 7,005,264 B2 | 2/2006 | Su et al. |
| 7,126,136 B2 | 10/2006 | Chen |
| 7,459,145 B2 | 12/2008 | Bao et al. |
| 7,462,325 B2 | 12/2008 | Hancock et al. |
| 7,744,816 B2 | 6/2010 | Su et al. |
| 9,547,014 B2 | 1/2017 | Travis et al. |
| 2005/0143472 A1 | 6/2005 | Wu et al. |
| 2005/0260654 A1 | 11/2005 | Wang et al. |
| 2007/0031283 A1 | 2/2007 | Davis et al. |
| 2007/0189359 A1 | 8/2007 | Chen et al. |
| 2008/0100279 A1 | 5/2008 | Mohapatra et al. |
| 2008/0176076 A1 | 7/2008 | Van Veggel et al. |
| 2008/0241071 A1 | 10/2008 | West et al. |
| 2008/0305045 A1 | 12/2008 | Kuniyil et al. |
| 2009/0087868 A1 | 4/2009 | Wang et al. |
| 2009/0104614 A1 | 4/2009 | Tsourkas et al. |
| 2009/0104643 A1 | 4/2009 | Bartholomeusz |
| 2009/0155173 A1 | 6/2009 | Scherman et al. |
| 2009/0186368 A1 | 7/2009 | Raven et al. |
| 2009/0263914 A1 | 10/2009 | Pettersson |
| 2010/0124789 A1 | 5/2010 | Bamdad |
| 2011/0177620 A1 | 7/2011 | Pettersson |
| 2011/0200529 A1 | 8/2011 | Rao et al. |

FOREIGN PATENT DOCUMENTS

| | | |
|---|---|---|
| WO | 2007011660 A2 | 1/2007 |
| WO | 2007106900 A2 | 9/2007 |
| WO | 2007125300 A1 | 11/2007 |
| WO | 2009048533 A2 | 4/2009 |

OTHER PUBLICATIONS

Zimmer et al., "Identification of a Molecular Target for the Calcium-modulated Protein S100. Fructose-1,6-Biophosphate Aldolase," J. Biol. Chem. 261(24):11424-11428 (1986).
Burns et al., "The Photometric Estimation of Luciferase in Luminous Bacterial Cells," Anal. Biochem. 5:393-415 (1963).
Kanner et al., "Serum S100beta. A Noninvasive Marker of Blood-Brain Barrier Function and Brain Lesions," Cancer 97(11):2806-2813 (2003).
International Search Report and Written Opinion for Corresponding PCT Application No. PCT/US2012/041886, filed Jun. 11, 2012 (dated Nov. 5, 2012).
Chikkaveeraiah et al., "Microfluidic Electrochemical Immunoarray for Ultrasensitive Detection of Two Cancer Biomarker Proteins in Serum," Biosens. Bioelectron. 26:4477-4483 (2011).
Akella et al., "Electrochemical Studies of Glucose Oxidase Immobilized on Glutathione Coated Gold Nanoparticles," Indian J. Biochem. & BioPhys. 44:82-87 (2007).
Algar et al., "New Opportunities in Multiplexed Optical Bioanalyses Using Quantum Dots and Donor-Acceptor Interactions," Anal. Bioanal. Chem. 398:2439-2449 (2010).
Algar et al., "Beyond Labels: A Review of the Application of Quantum Dots as Integrated Components of Assays, Bioprobes, and Biosensors Utilizing Optical Transduction," Analytica Chimica Acta 673:1-25 (2010).

(Continued)

*Primary Examiner* — Olga N Chernyshev
(74) *Attorney, Agent, or Firm* — Troutman Pepper Hamilton Sanders LLP

(57) ABSTRACT

The present invention relates to methods of detecting a neural injury biomarker in a biological sample. The method includes subjecting a biological sample to an assay according to the present invention that produces a measurable signal and detecting the measurable signal. The presence or absence of the measurable signal indicates the presence or absence of the biomarker in the sample. The present invention also relates to methods of determining the state of a subject's neural injury. The present invention also relates to systems and devices useful in carrying out the methods of the present invention.

45 Claims, 23 Drawing Sheets

(56) References Cited

OTHER PUBLICATIONS

He et al., "Ultrasensitive Nucleic Acid Biosensor Based On Enzyme-Gold Nanoparticle Dual Label and Lateral Flow Strip Biosensor," Biosens. Bioelectron. 26:2018-2024 (2011).
Cheng et al., "Combining Biofunctional Magnetic Nanoparticles and ATP Bioluminescence for Rapid Detection of *Escherichia coli*," Talanta 77:1332-1336 (2009).
Liu et al., "Rare Cell Chemiluminescence Detection Based on Aptamer-Specific Capture in Microfluidic Channels," Biosens. Bioelectron. 28:438-442 (2011).
Wagner et al., "Use of Quantum Dots in the Development of Assays for Cancer Biomarkers," Anal. Bioanal. Chem. 397:3213-3224 (2010).
Ambrosi et al., "Enhanced Gold Nanoparticle Based ELISA for a Breast Cancer Biomarker," Anal. Chem. 82:1151-1156 (2010).
Saenger et al., "Stroke Biomarkers: Progress and Challenges for Diagnosis, Prognosis, Differentiation, and Treatment," Clinical Chemistry 56:21-33 (2010).
Gurnett et al., "Analysis of Cerebrospinal Fluid Glial Fibrillary Acidic Protein After Seizures in Children," Epilepsia 44:1455-1458 (2003).
Marion et al., Proceedings of the Military mTBI Diagnostics Workshop, St. Pete Beach, Journal of Neurotrauma 28:517-526 (2011).

FIG. 1A

| DETECTION MODALITIES | BIOMARKER | LUMINESCENCE TRANSDUCER | LUMINESCENCE INTERMEDIATE |
|---|---|---|---|
| Enzymatic: | | | |
| | NSE* | Luc | ATP |
| | PGM# | Luc | ATP |
| | NDK-A | Luc | ATP |
| Oxidation: | | | |
| I. Oxidized | Spermine | HRP | $H_2O_2$ |
| | Uric acid# | HRP | $H_2O_2$ |
| | Glutamate# | HRP | $H_2O_2$ |
| | Arginine | HRP | $H_2O_2$ |
| | Glycine | HRP | $H_2O_2$ |
| | Glucose# | HRP | $H_2O_2$ |
| | Homocysteine | HRP | $H_2O_2$ |
| | Iron | HRP | $H_2O_2$ |
| II. Oxidase | SMO | HRP | $H_2O_2$ |
| | PAO | HRP | $H_2O_2$ |
| Cleavage: | | | |
| I. Release of BL Enzyme | MMP1 | BL | |
| | MMP2 | BL | |
| | MMP9 | BL | |
| | APC | BL | |
| | Chitotriosidase | BL | |
| | TPA | BL | |
| II. release of BL substrate | GST* | Luc | Lun-NT |
| Affectors: | | | |
| | S100β* | Luc | ATP |
| BL cofactors: | | | |
| | $Ca^{2+\#}$ | Aequorin | coelenterazine |
| Phosphorylation: | | | |
| | GFAP | Luc | ATP/AMP | indicates data described herein

FIG. 1B

| Biomarker | Assay Components According to Selected Assay Embodiments (*Indicates an enzyme; # indicates a co-factor; $indicates a substrate) |
|---|---|
| NSE | PK*, Luc*, 2-PG$, ADP#, lun$, $O_2$ |
| PGM | enolase*, PK*, Luc*, 3-PG, ADP#, lun$, $O_2$ |
| NDK-A | GTP#, ADP#, lun$, $O_2$, luc *; |
| Spermine | spermine oxidase*, HRP*, luminol$, $H_2O$, $O_2$ |
| Uric acid | uricase*, HRP*, $H_2O$, $O_2$, luminol$; |
| Glutamate | glutamate oxidase*, HRP*, luminol$, $H_2O$, $O_2$; |
| Arginine | arginine oxidase*, HRP*, luminol$, $H_2O$, $O_2$ |
| Glycine | glycine oxidase*, HRP*, luminol$, $H_2O$, $O_2$ |
| Glucose | glucose oxidase*, HRP*, $H_2O$, $O_2$, luminol$ |
| Homocysteine | methionine synthase*, methionine oxidase*, $H_2O$, $O_2$, HRP*, luminol$ |
| Iron | iron oxidase*, HRP*, luminol$, $H_2O$, $O_2$ |
| PAO | N1AS$, $H_2O$, $O_2$, HRP*, luminol$ |
| SMO | spermine$, HRP*, luminol$, $H_2O$, $O_2$ |
| MMP(1, 2, 9) | collagen-Luciferase* (Luc), ATP#, luciferin$ (Lun), $O_2$ |
| APC | factor V-Luc*, ATP#, $O_2$, lun$ |
| Chitotriosidase | chitin-Luc*, ATP#, Lun$, $O_2$ |
| TPA | plasminogen-Luc*, ATP#, $O_2$, lun$ |
| GST | luciferin-NT$, GSH$, Luc*, ATP#, $O_2$ |
| S100β | [aldolase*, GAPDH*, PGK*, F1.6.BP$] or [PGM*, ENO*, PK*] Luc*, ADP#, Lun, $O_2$ |
| $Ca^{2+}$ | aequorin*, coelenterazine$, $O_2$ |
| GFAP | GFAP-kinase (e.g. ROCK-I*, ROCK-II, aurora-b*) ADPTK*, ATP#, Luc*, Lun$, $O_2$ |

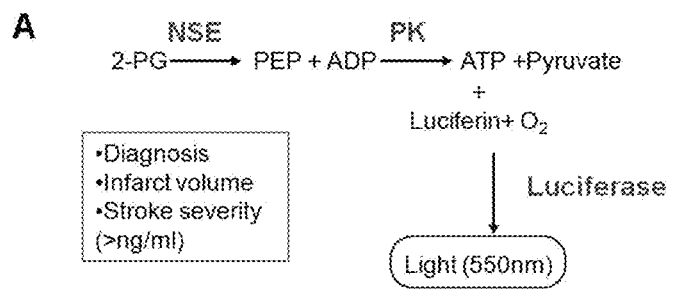
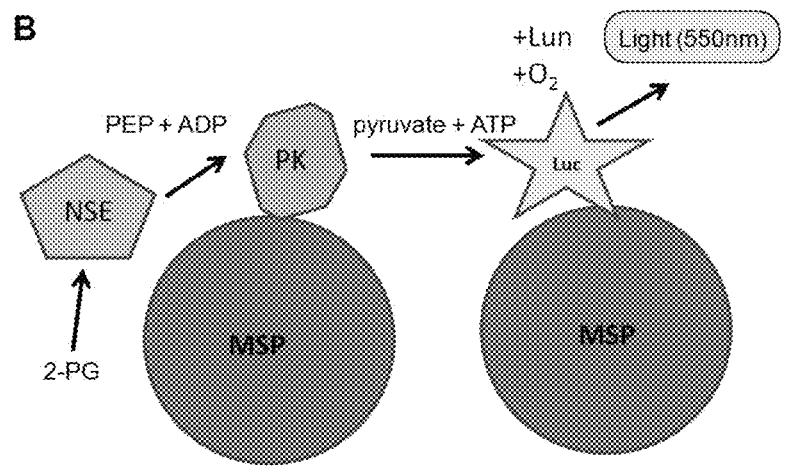
FIGS. 6A-6B
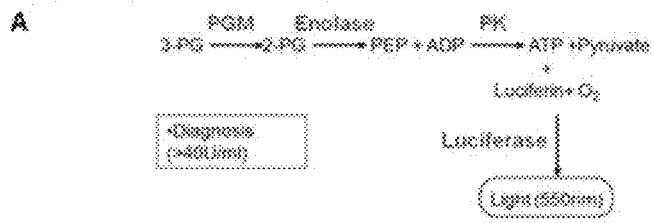
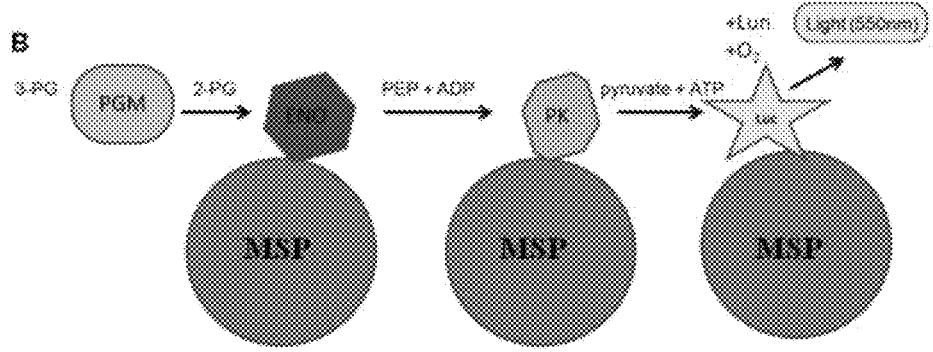
FIGS. 7A-7B

Uric acid
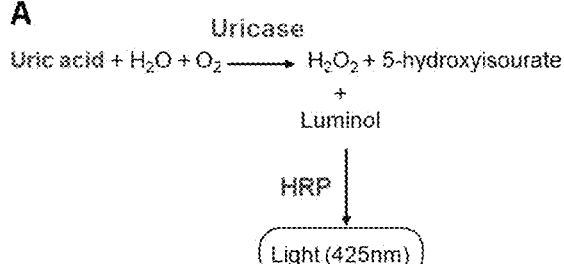 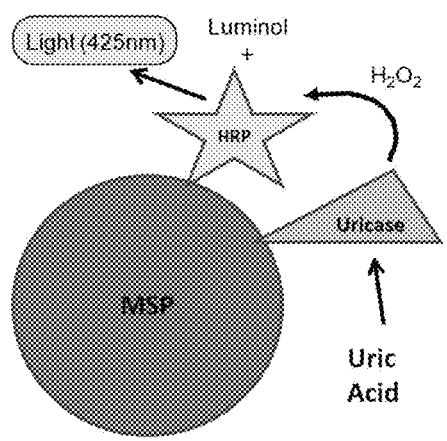
FIGS. 10A-10B
Glutamate
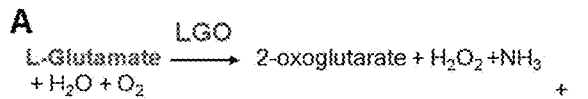 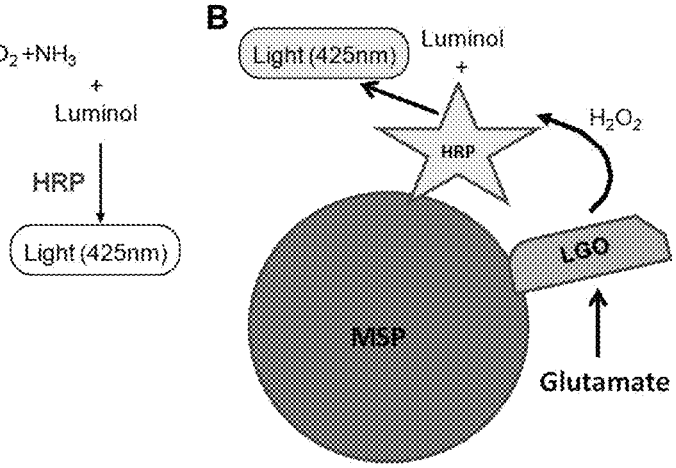
FIGS. 11A-11B Arginine
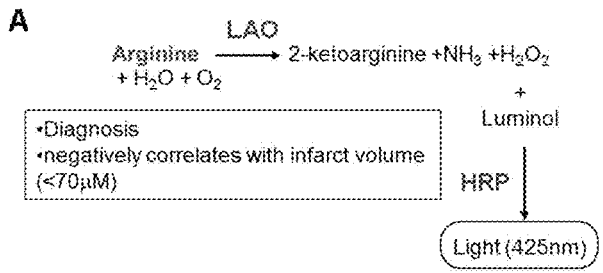 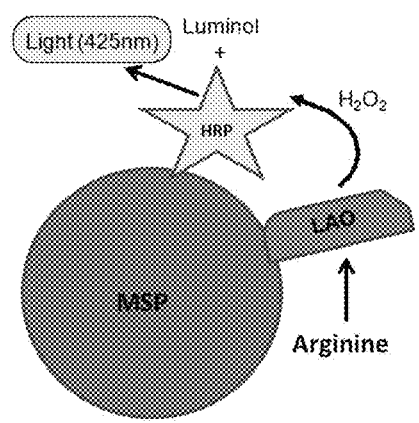
FIGS. 12A-12B
Glycine
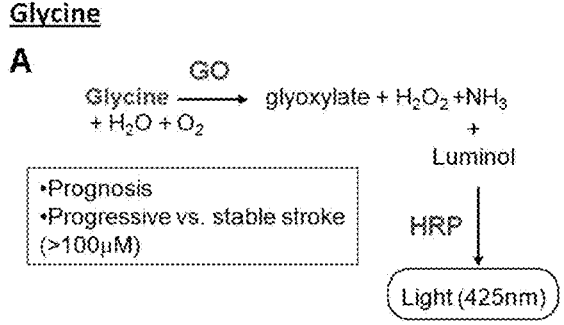 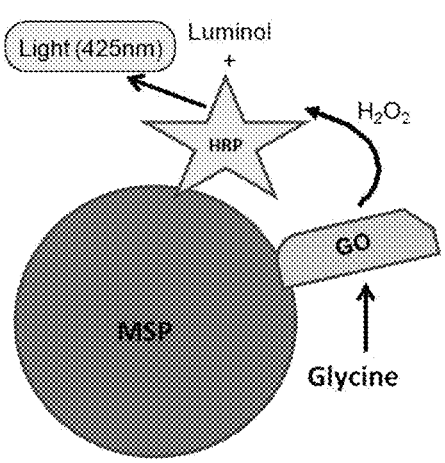
FIGS. 13A-13B
Glucose
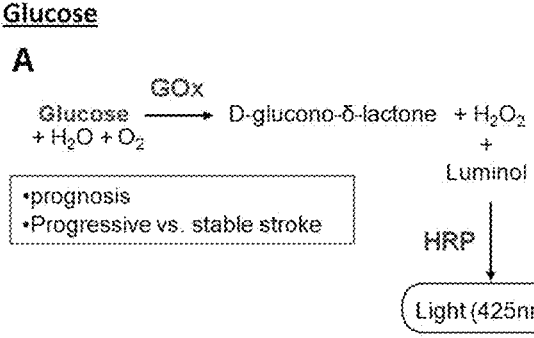 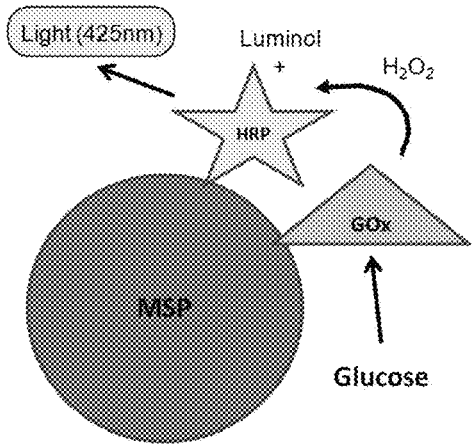
FIGS. 14A-14B

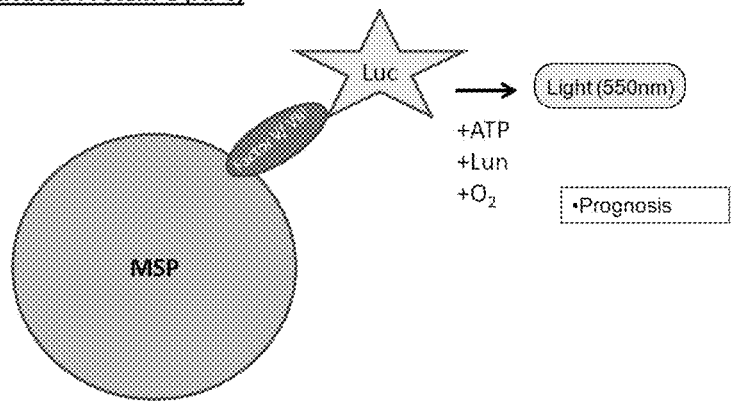
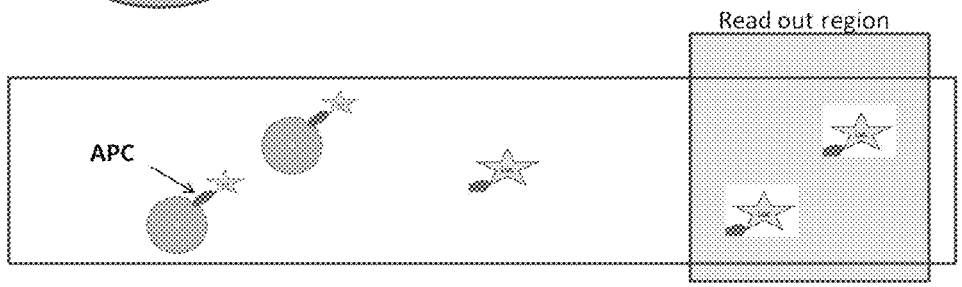
FIGS. 21A-21B
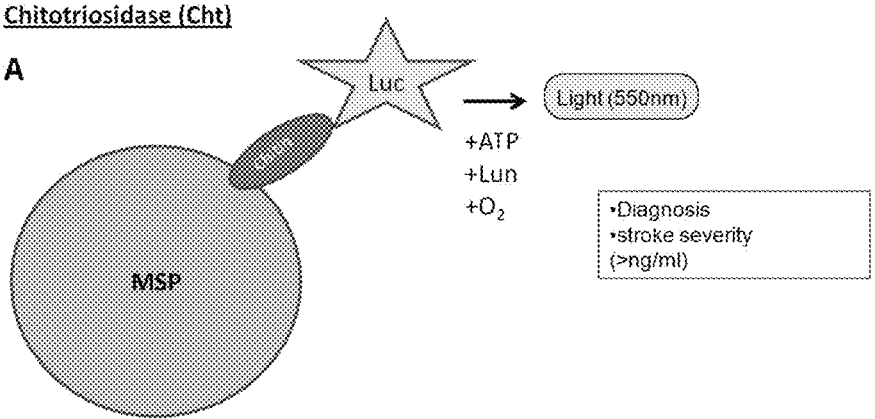
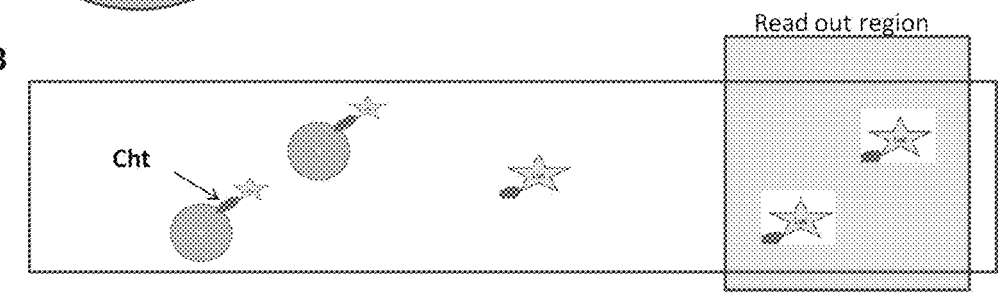
FIGS. 22A-22B

Tissue Plasminogen Activator (TPA)
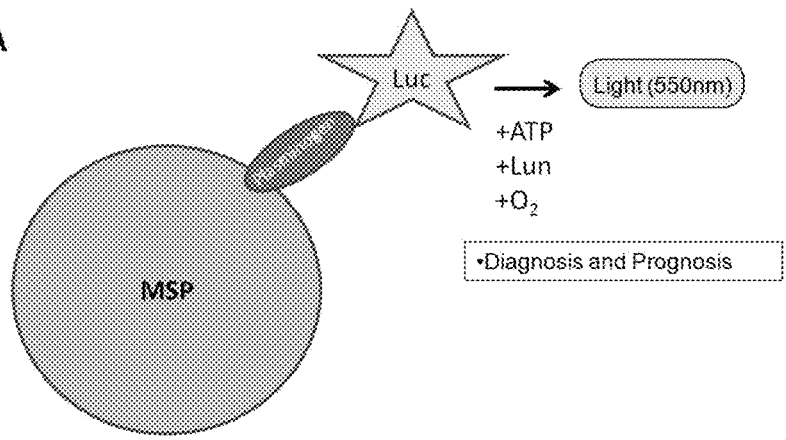
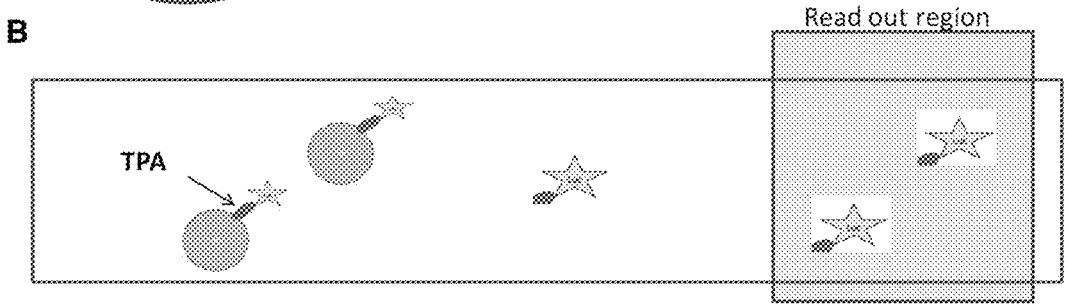
FIGS. 23A-23B
Glutathione S transferase (GST)
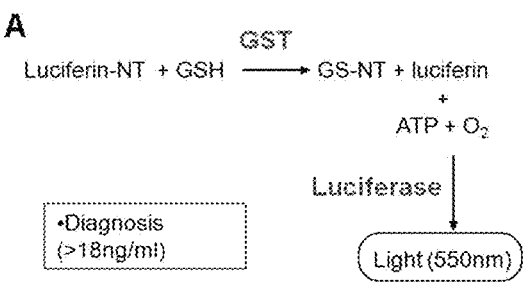
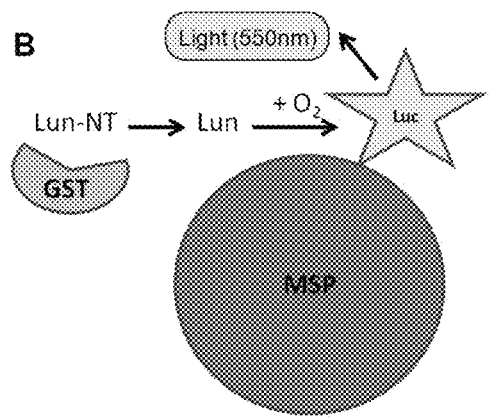
FIGS. 24A-24B

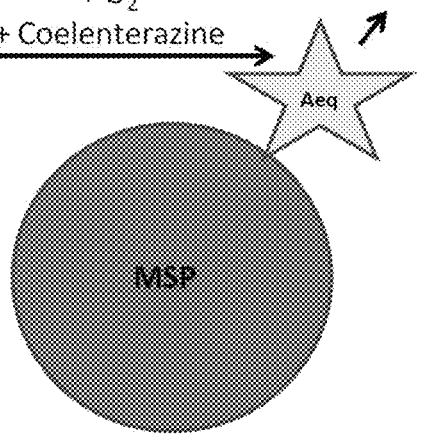
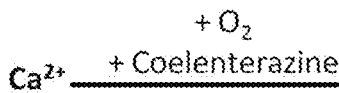
FIGS. 25A-25B
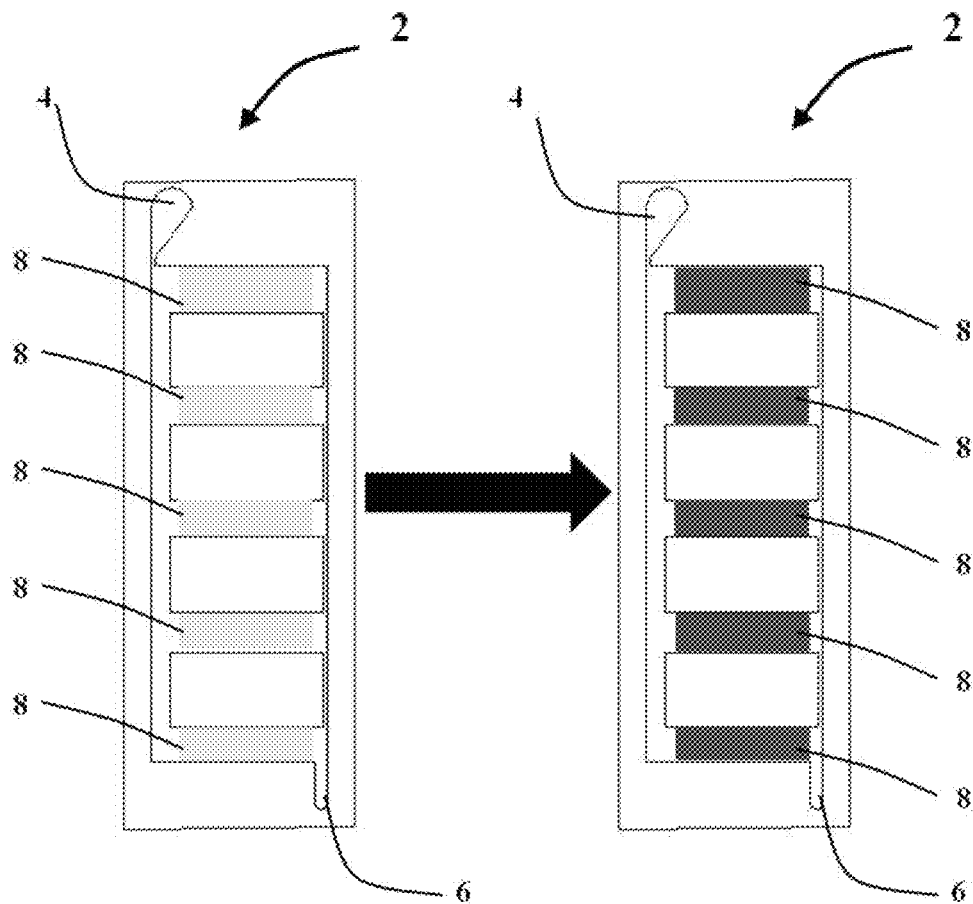
FIG. 26

A. Neuron Specific Enolase (enzymatic detection modality)

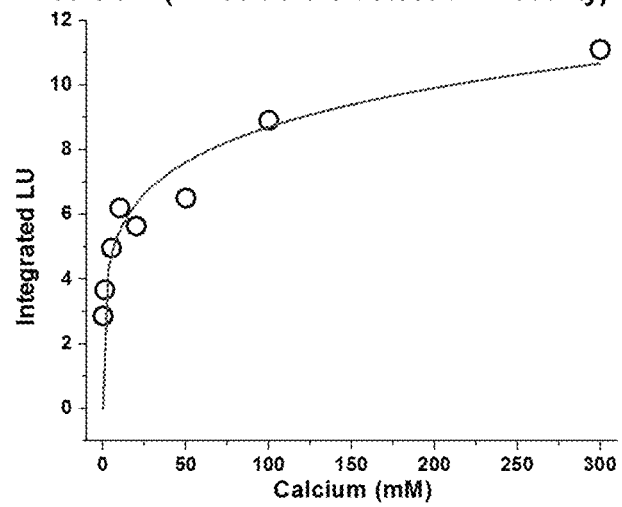
FIG. 31H
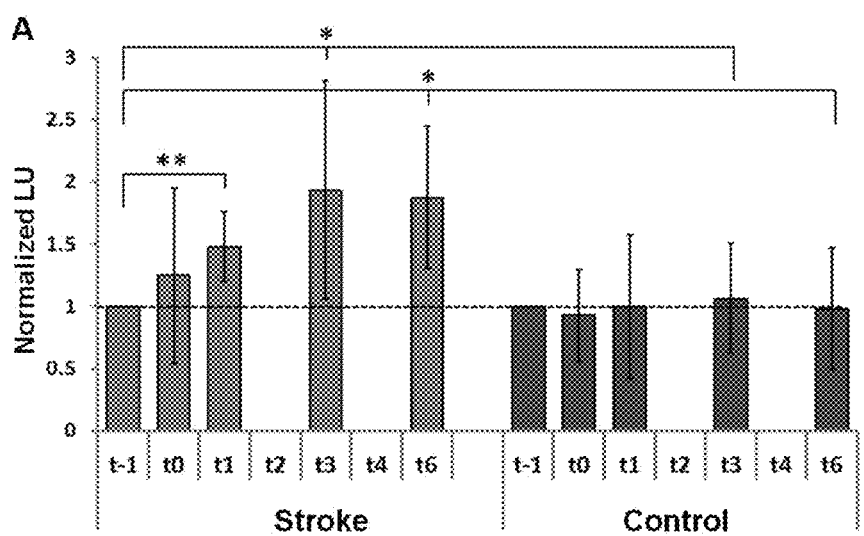
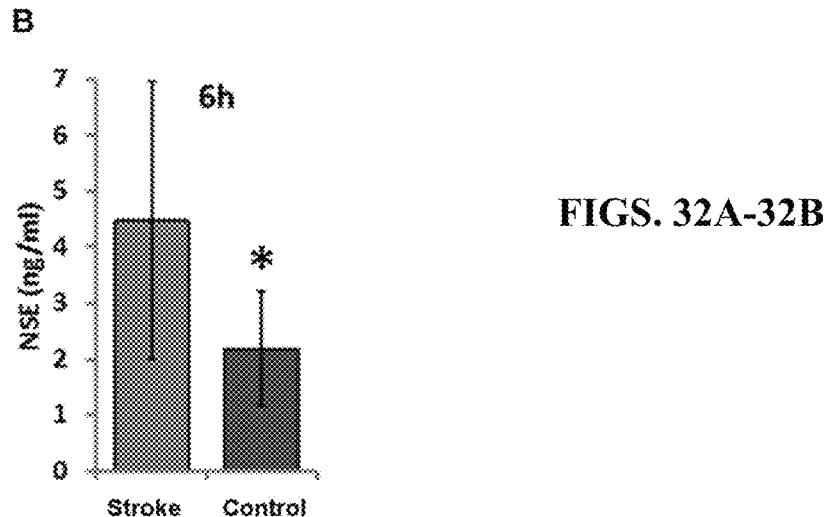
FIGS. 32A-32B

IMMOBILIZED PROTEIN SYSTEM FOR RAPID AND ENHANCED MULTIPLEXED DIAGNOSTICS

This application is a divisional of U.S. patent application Ser. No. 14/125,221, filed Feb. 7, 2014, now U.S. Pat. No. 9,547,014, issued Jan. 17, 2017, which is a national stage application under 35 U.S.C. § 371 of International Patent Application No. PCT/US2012/041886, filed Jun. 11, 2012, which claims the benefit of U.S. Provisional Patent Application Ser. No. 61/495,804, filed Jun. 10, 2011, each of which is hereby incorporated by reference in its entirety.

This invention was made with government support under grant number 5-DP-1OD-006431 awarded by National Institutes of Health. The government has certain rights in the invention.

FIELD OF THE INVENTION

The present invention relates to assays for the detection of neural injury biomarkers.

BACKGROUND OF THE INVENTION

There is a great clinical need for Point-of-Care Testing ("PoCT") devices so that an accurate diagnosis can be made quickly, enabling appropriate treatment or response as early as possible. A rapid detection system for the diagnosis of neural injury (e.g., stroke, concussion, contusion, trauma, and aneurism) is especially important, because the treatment options for certain neural injuries such as stroke are extremely time sensitive, with maximal benefits occurring only if treatment can be initiated within the first few hours post-event.

Continuing the example of stroke, current diagnostic methodology relies on neurological expertise and advanced medical imaging techniques (e.g., Computerized Tomography/Magnetic Resonance Imaging ("CT/MRI"), which are not widely available, and are time consuming and expensive. Because of these limitations, only 4% of patients suffering from ischemic stroke receive treatment (tissue plasminogen activator) within the 3-hour effective window (Roger et al., "Heart Disease and Stroke Statistics—2011 Update: A Report From the American Heart Association," *Circulation* 123(4):e18-e209 (2011)). Because of the enormity of the clinical need, much attention is focused on developing PoCT to detect pathology-specific biomarkers. Biomarkers can themselves be various substances, such as proteins, lipids, sugars, nucleic acids, or ions. Blood biomarkers for neural injury have received much attention due to the difficulties regarding timely clinical diagnosis. Currently, over 50 candidate bio-molecules including proteins, metabolites and antibodies have been identified and investigated for varied applications in diagnosis, outcome prediction, or treatment (Jickling and Sharp, "Blood Biomarkers of Ischemic Stroke," *Neurotherapeutics* 8(3):349-60 (2011); Saenger and Christenson, "Stroke Biomarkers: Progress and Challenges for Diagnosis, Prognosis, Differentiation, and Treatment," *Clin. Chem.* 56(1):21-33 (2010); Whiteley et al., "Blood Markers for the Prognosis of Ischemic Stroke: A Systematic Review," *Stroke* 40(5):e380-9 (2009); and Hasan et al., "Towards the Identification of Blood Biomarkers for Acute Stroke in Humans: A Comprehensive Systematic Review," *Br. J. Clin. Pharmacol.* (2012)). The growing list of potential biomarkers provides a useful resource to guide the development of PoCT diagnostic technologies. However, there remains a great need for a rapid detection system for the diagnosis of neural injury.

Several examples of PoCT biomarker detection technologies for the diagnosis of various diseases have recently been described. These technologies are divided into 3 major categories including chemical-, immunoassay- or nucleic acid-based detection systems with various signal readout methods such as absorbance, fluorescence, luminescence, electrochemical and colorimetric (Chin et al., "Commercialization of Microfluidic Point-of-Care Diagnostic Devices," *Lab Chip* (2012)). This list includes Atolyzer® (Atonomics), Triage® (Alere), Spinit® (Biosurfit), and i-STAT® (i-STAT Corp). However, despite such PoCT systems, there remains a great need for increased sensitivity and speed in detecting biomarkers, especially neural injury biomarkers.

The present invention is directed to overcoming these and other deficiencies in the art.

SUMMARY OF THE INVENTION

One aspect of the present invention relates to a method for detecting the presence or absence of a neural injury biomarker in a biological sample. This method includes providing a biological sample and subjecting the biological sample to an assay to detect the neural injury biomarker. The assay is selected from the group consisting of: (a) an assay to detect S100β, where the assay includes (i) providing aldolase, glyceraldehyde 3-phosphate dehydrogenase ("GAPDH"), and a signal-transducing molecule, each immobilized on one or more supports, (ii) providing fructose 1,6-bisphosphate and $NAD^+$, and (iii) contacting the biological sample with the one or more supports, $NAD^+$, and fructose 1,6-bisphosphate under conditions effective to cause a cascading biological reaction leading to production of a measurable signal by the signal-transducing molecule if S100β is present in the biological sample; (b) an assay to detect S100β, where the assay includes (i) providing phosphoglyceromutase ("PGM"), enolase, pyruvate kinase, and a signal-transducing molecule, each immobilized on one or more supports, (ii) providing 3-phosphoglycerate and (iii) contacting the biological sample with the one or more supports and 3-phosphoglycerate under conditions effective to cause a cascading biological reaction leading to production of a measurable signal by the signal-transducing molecule if S100β is present in the biological sample; (c) an assay to detect glial fibrillary acidic protein ("GFAP"), where the assay includes (i) providing a GFAP-phosphorylating kinase and luciferase, each immobilized on one or more supports, (ii) providing D-luciferin, $O_2$, and ATP, and (iii) contacting the biological sample with the one or more supports, D-luciferin, $O_2$, and ATP under conditions effective to permit a sequential reaction, whereby GFAP, if present in the biological sample, will react with the GFAP-phosphorylating kinase and ATP thereby producing ADP, whereby a decreased amount of ATP reacts with D-luciferin, $O_2$, and luciferase to produce a measurable signal compared to when GFAP is not present in the biological sample and the sequential reaction does not take place; (d) an assay to detect a neural injury biomarker, wherein the neural injury biomarker is an enzyme, the assay including (i) providing one or more substrates of the neural injury-biomarker and one or more co-factors, (ii) providing one or more enzymes capable of acting upon the product of a reaction between the neural injury biomarker and the one or more substrates, wherein at least one enzyme is immobilized on one or more supports and at least one of the one or more enzymes is a signal-transducing molecule; and (iii) contacting the biological sample with the one or more substrates and the one or more enzymes under conditions effective to permit a sequential reaction, whereby the neural injury biomarker, if present in the biological sample, will react with the one or more substrates causing a single reaction or a series of coupled reactions that cause production of a measurable signal by the signal-transducing molecule; and (e) combinations of two or more of (a), (b), (c), and (d). The method also includes detecting, based on the subjecting, the measurable signal, where the measurable signal indicates presence or absence of the neural injury biomarker in the biological sample.

Another aspect of the present invention relates to a method of determining a subject's neural injury state. This method comprises carrying out a method for detecting the presence or absence of a neural injury biomarker in a biological sample according to the present invention, where the biological sample is provided from a subject. The method also comprises determining, based on the detecting, the neural injury state of the subject.

Yet another aspect of the present invention relates to a system. This system includes a platform including one or more channels. At least one channel of the one or more channels includes (a) biological assay components suitable to detect the presence of S100β in a biological sample, said components including: (i) aldolase, GAPDH, and a signal-transducing molecule, each immobilized within the at least one channel and (ii) fructose 1,6-bisphosphate and $NAD^+$, said components positioned in the channel to permit a cascading biological reaction leading to production of a measurable signal by the signal-transducing molecule if S100β is present in the biological sample; (b) biological assay components suitable to detect the presence of S100β in a biological sample, said components including: (i) phosphoglyceromutase ("PGM"), enolase, pyruvate kinase, and a signal-transducing molecule, each immobilized within the at least one channel and (ii) 3-phosphoglycerate, said components positioned in the channel to permit a cascading biological reaction leading to production of a measurable signal by the signal-transducing molecule if S100β is present in the biological sample; (c) biological assay components suitable to detect the presence of GFAP in a biological sample, the components including: (i) a GFAP-phosphorylating kinase and luciferase, each immobilized within the at least one channel, (ii) D-luciferin, $O_2$, and ATP, said components positioned in the at least one channel to permit a sequential reaction in the presence of GFAP, whereby GFAP will react with the GFAP-phosphorylating kinase and ATP to produce ADP; (d) biological assay components suitable to detect the presence of a neural injury biomarker in a biological sample, wherein the neural injury biomarker is an enzyme, said components including: (i) one or more substrates of the neural injury biomarker and one or more co-factors; (ii) one or more enzymes capable of acting upon the product of a reaction between the neural injury biomarker and the one or more substrates, wherein at least one enzyme is immobilized within the at least one channel on one or more supports and at least one enzyme is a signal-transducing molecule, said components positioned in the channel to permit a sequential reaction, whereby the neural injury biomarker, if present in the biological sample, will react with the one or more substrates causing a single reaction or a series of coupled reactions that cause production of a measurable signal by the signal-transducing molecule; or (e) combinations of two or more of (a), (b), (c), and (d).

The present invention relates to significant advances in methods of detecting specific biomarkers through the use of, for example, enzyme reactions in which the enzymes are tethered to surfaces (e.g., nanoparticles using an approach of oriented immobilization). The present invention also relates to how this method can be employed as a system to detect one or more biomarkers (e.g., to diagnose neural injury). Several embodiments are presented, including, e.g., use in a microfluidic card/reader system for diagnostic and prognostic applications in which luminescence is a readout or in small devices that have colorimetric readouts. In certain embodiments, the present invention relates to the use of recombinant protein technology to tether proteins to surfaces via specifically positioned binding domains that optimize their function in contrast to proteins that are attached via non-specific or non-oriented chemical approaches. Biomarker recognition is performed by enzymatic reactions that differ depending on the biomarker. For neural injury, examples of diagnostic and/or prognostic biomarkers are provided. Because biomarkers differ in terms of their nature (ranging from ions to sugars to proteins), several classifications of enzymatic reaction methodologies are presented (enzymatic, oxidative, cleavage, affector, bioluminescent cofactor, phosphorylation) that can be used to achieve detection. Examples of how to link these reactions to a bioluminescent readout that can be identified with a hand-held photon detector are also provided. The technology is suitable for a point-of-care testing device which can be employed in the field, in transit to a medical facility, or in a medical facility.

The present invention encompasses, inter alia, enzyme-based methods and systems that integrate those methods for the detection of biomarkers. Using the example of diagnosis of neural injury such as stroke, a selected panel of biomarkers can be detected through the use of specific assays utilizing, e.g., enzymatic reactions described herein that are tailored to each biomarker. These assays are referred to as assays, assay modalities, detection modalities, assay detection modalities, or modalities. Each of these assay modalities may be transduced into a common luminescent output. That is, in certain embodiments, they may be all linked to bioluminescent (BL) proteins or substrates that will allow light to be emitted and read, with the amount of that light correlated to the amount of biomarker in the system or biological sample. This technology is suitable for generating qualitative as well as quantitative results for these various biomarkers. The detection of one or more biomarkers for neural injury may also be transduced into a colorimetric readout, showing the flexibility of the method and the systems described herein. For example, a diagnostic card comprising a system according to the present invention with colorimetric readout could be used in field settings to diagnose neural trauma. Yet other embodiments could use tethered enzymes as diagnostics for, e.g., idiopathic hemolytic anemia diagnosis or for determining blood glucose.

The present invention confers multiple advantages over other detection methods and systems. For example, advantages of certain features of various embodiments of the present invention include 1) speed—assays using enzymatic reactions occur thousands of times faster than antibody-antigen interactions currently used; 2) luminescence or colorimetric based readouts may be used, which enable stand-alone, highly portable systems and devices that do not require bulky excitation elements (such as for fluorescence); 3) sensitivity—enzymatic reaction assays facilitate signal amplification at the steps of both detection and readout; 4) reduced cost of fabrication—likely components of such systems, including, e.g., nanoparticles and/or microfluidic channels (microchannels), may be made from inexpensive materials and can easily be mass produced; 5) small sample size—rapid enzymatic detection in an assay incorporated into a microchannel design only requires nanoliter amounts of plasma per channel; 6) accurate quantification—different amounts of the same tethered enzymes could be placed in adjacent channels in a system according to the present invention, providing variable range sensitivity for each biomarker tested; 7) multiplex capability—coupled biochemical reactions could detect multiple biomarkers in a single card-reader system in certain embodiments of the present invention; 8) use of tethered enzymes facilitates maximum enzyme stability and activity; 9) use of tethered enzymes confines reactions and readouts to specific areas of the system (e.g., a specific region of a card), reducing the size of a photodetector in the reader; 10) use of tethered enzymes confines reactions and readouts allowing for in-line negative controls and controls for background color, luminescence or fluorescence; 11) use of tethered enzymes confines reactions and readouts, reducing light contamination from detection of other biomarkers in the same card-reader system; and 12) a chip/reader system according to certain embodiments of the present invention is small, robust, and portable. Such a system would not require an excitation light source and will, therefore, have low energy demands.

The methods and systems presented herein provide significant advantages involving, inter alia, the detection of neural injury biomarkers in a sample.

BRIEF DESCRIPTION OF THE DRAWINGS

FIGS. 1A-1B are tables showing classification of biomarkers for neural injury or damage by assay modality or detection modality (FIG. 1A), as well as the assay components suitable to detect those neural injury biomarkers according to certain embodiments of the present invention (FIG. 1B). The luminescence transducer represents the bioluminescent ("BL") protein that might be used and the luminescence intermediates would be the substrates for these proteins. Note that variations of coupled reactions for the assay modalities or detection modalities could result in colorimetric readouts (e.g., for HRP mediated readout, luminol will be replaced with chromogenic substrates (e.g., TMB (3,3',5,5'-tetramethylbenzidine), DAB (diaminobenzidine), or ABTS (2,2'-azino-bis(3-ethylbenzthiazoline-6-sulfonic acid)). FIG. 1B provides examples of enzymes, co-factors, substrates, and reactants that may be provided for assays according to the present invention in which the particular neural injury biomarker is to be detected. The abbreviations used throughout these figures include the following: magnetic silica nanoparticles ("MSP"); Neuron-Specific Enolase ("NSE"); Pyruvate Kinase ("PK"); Luciferase ("Luc"); Renilla Luciferase ("R-Luc"); 2-Phosphoglycerate ("2-PG"); Adenosine Diphosphate ("ADP"); Adenosine Monophosphate ("AMP"); Luciferin ("Lun"); Phosphoglyceromutase ("PGM"); Oxygen ("$O_2$"); Hydrogen Peroxide ("$H_2O_2$"); 3-Phosphoglycerate ("3-PG"); 2-Phosphoglycerate ("2-PG"); Glyceraldehyde 3-Phosphate ("GA3P"); 1,3-Bisphospho-glycerate ("1,3,BPG"); Aldolase ("Ald"); Nucleoside-diphosphate Kinase A ("NDK-A"); Guanosine Triphosphate ("GTP"); Guanosine Diphosphate ("GDP"); Horseradish Peroxidase ("HRP"); Total Polyamine Oxidase ("PAO"); N1-acetylspermine ("N1AS"); Matrix Metalloproteinase ("MMP"); Adenosine Triphosphate ("ATP"); phosphoenolpyruvate ("PEP"); Spermine Oxidase ("SMO"); L-Glutamate Oxidase ("LGO"); L-Arginine Oxidase ("LAO"); Glycine Oxidase ("GO"); Glucose Oxidase ("GOx"); Methionine Synthase ("MS"); Methionine Oxidase ("MOx"); Iron Oxidase ("IRo"); Activated Protein C ("APC"); Tissue Plasminogen Activator ("TPA"); Glutathione S-Transferase ("GST"); Glutathione ("GSH"); Chitotriosidase ("Cht"); Glyceraldehyde 3-Phosphate Dehydrogenase ("GAPDH"); Fructose 1,6-Bisphosphate ("F1.6.BP"); Enolase ("ENO"); Glial Fibrillary Acidic Protein ("GFAP"); Rho-Kinase ("ROCK"); Aequorin ("Aeq"); ADP Thymidine Kinase ("ADPTK"); Thymidine 5'-Phosphate ("T5P"); and PhosphoGlycerate Kinase ("PGK").

FIGS. 6A-6B show a reaction schematic for the detection of neuron-specific enolase (NSE) and clinical value of that detection (FIG. 6A), as well as a schematic diagram of the enzymatic assay modality being used to detect the biomarker NSE (FIG. 6B).

FIGS. 7A-7B show a reaction schematic for the detection of PGM and clinical value of that detection (FIG. 7A), as well as a schematic diagram of the enzymatic assay modality being used to detect the biomarker PGM (FIG. 7B).

FIGS. 10A-10B show a reaction schematic for the detection of uric acid (UA) and clinical value of that detection (FIG. 10A), as well as a schematic diagram of the oxidative I (oxidized) assay modality being used to detect the biomarker UA (FIG. 10B).

FIGS. 11A-11B show a reaction schematic for the detection of glutamate and clinical value of that detection (FIG. 11A), as well as a schematic diagram of the oxidative I (oxidized) assay modality being used to detect the biomarker glutamate (FIG. 11B).

FIGS. 12A-12B show a reaction schematic for the detection of arginine and clinical value of that detection (FIG.

12A), as well as a schematic diagram of the oxidative I (oxidized) assay modality being used to detect the biomarker arginine (FIG. 12B).

FIGS. 13A-13B show a reaction schematic for the detection of glycine and clinical value of that detection (FIG. 13A), as well as a schematic diagram of the oxidative I (oxidized) assay modality being used to detect the biomarker glycine (FIG. 13B).

FIGS. 14A-14B show a reaction schematic for the detection of glucose and clinical value of that detection (FIG. 14A), as well as a schematic diagram of the oxidative I (oxidized) assay modality being used to detect the biomarker glucose (FIG. 14B).

Figures 15A, 15B:
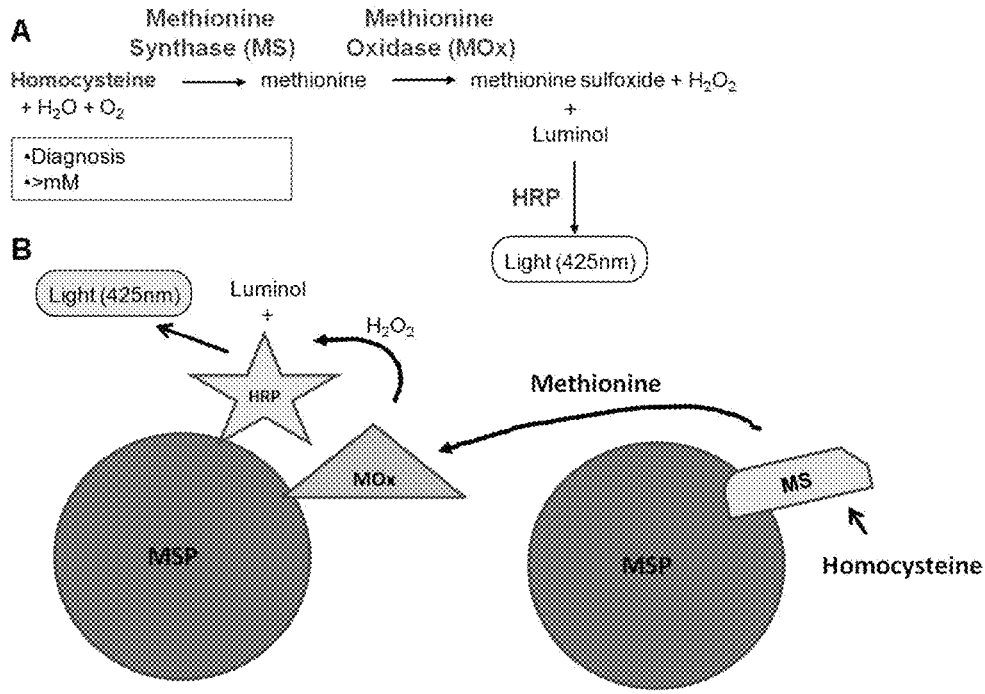

FIGS. 15A-15B show a reaction schematic for the detection of homocysteine and clinical value of that detection (FIG. 15A), as well as a schematic diagram of the oxidative I (oxidized) assay modality being used to detect the biomarker homocysteine (FIG. 15B).

Figures 16A, 16B:
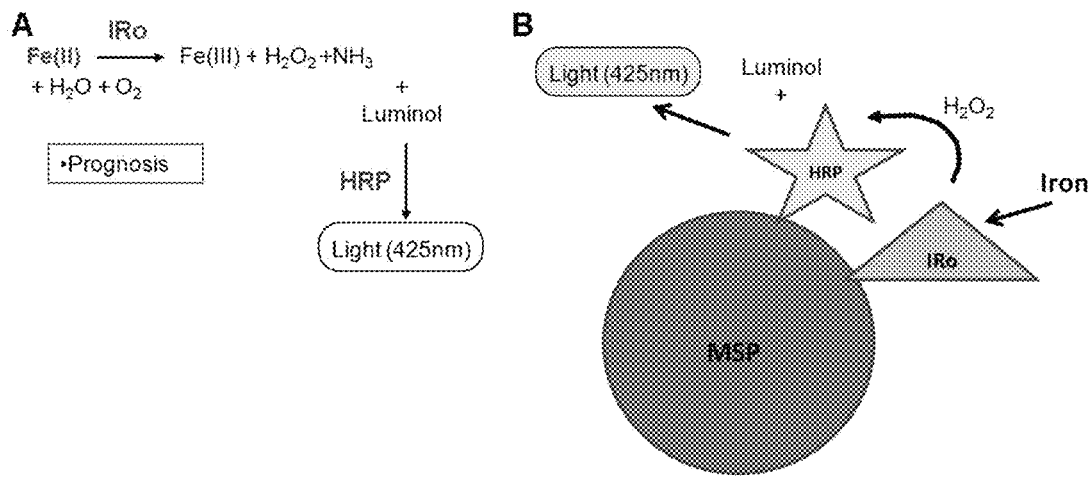

FIGS. 16A-16B show a reaction schematic for the detection of iron and clinical value of that detection (FIG. 16A), as well as a schematic diagram of the oxidative I (oxidized) assay modality being used to detect the biomarker iron (FIG. 16B).

Figure 17A:
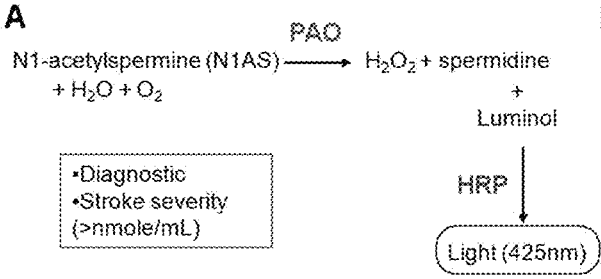
Figure 17B:
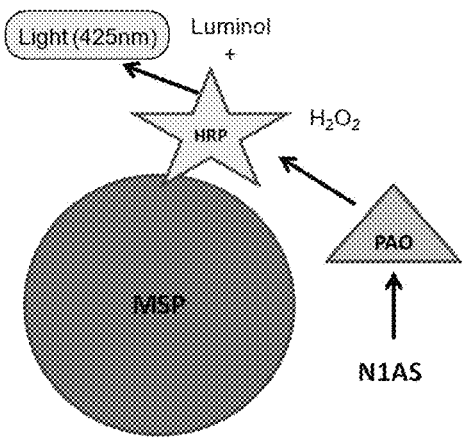
Figure 17C:
Figure 17D:
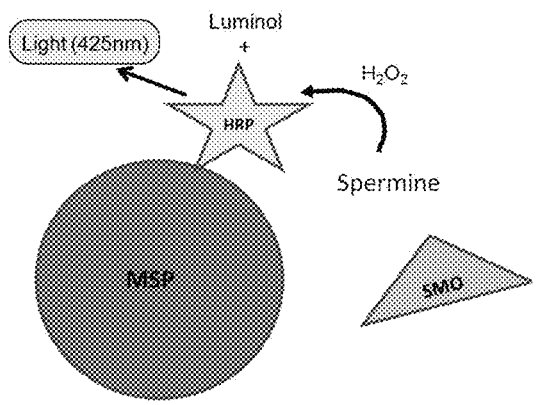

FIGS. 17A-17D show schematics relating to an oxidative II (oxidase) assay modality according to the present invention. FIGS. 17A-17B show a reaction schematic for the detection of total polyamine oxidase (PAO) and clinical value of that detection (FIG. 17A), as well as a schematic diagram of the oxidative II (oxidase) assay modality being used to detect the biomarker PAO (FIG. 17B). FIGS. 17C-17D show a reaction schematic for the detection of spermine oxidase ("SMO") and clinical value of that detection (FIG. 17C), as well as a schematic diagram of the oxidative II (oxidase) assay modality being used to detect the biomarker SMO (FIG. 17D).

Figure 18A:
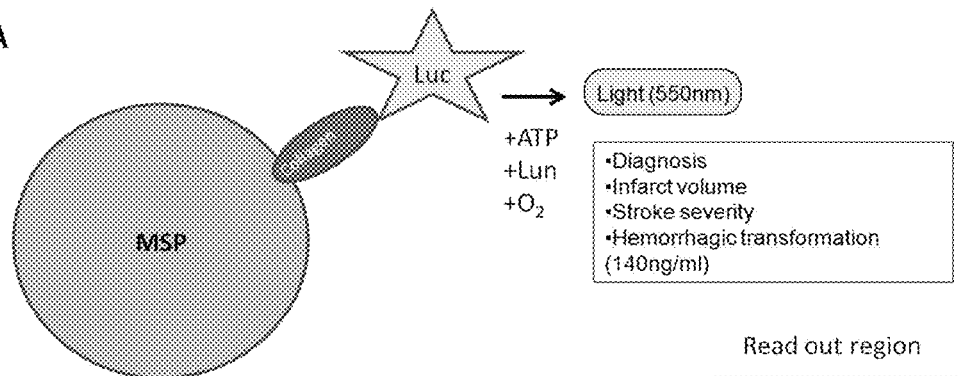
Figure 18B:
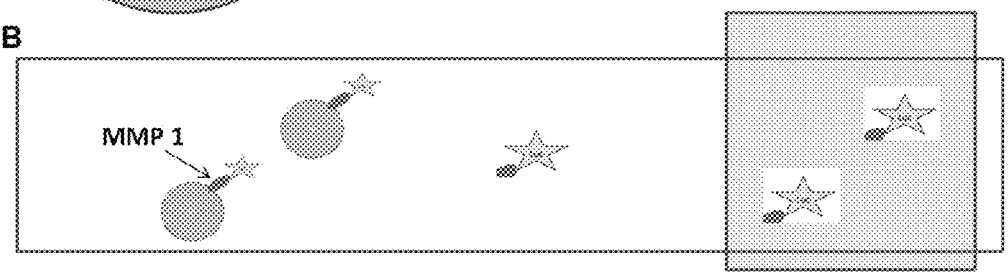
Figure 18C:
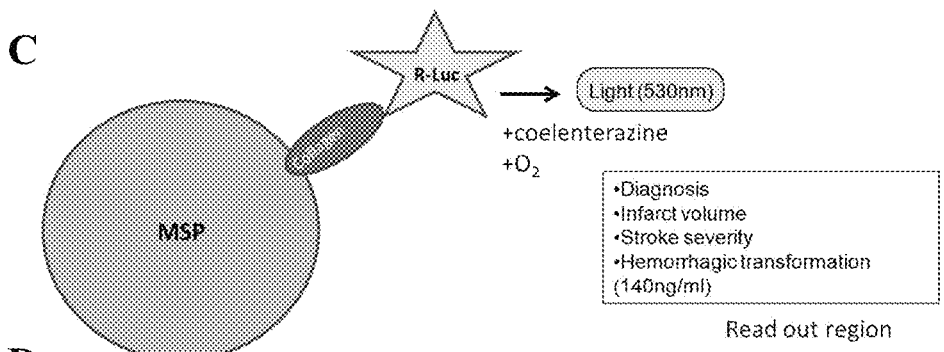
Figure 18D:
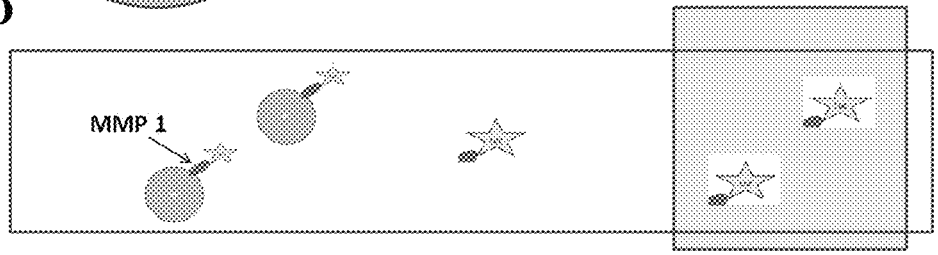

FIGS. 18A-18D show a schematic diagram of the protein assembly for the detection of matrix metalloproteinase (MMP1) and clinical value of that detection (FIGS. 18A; 18C), as well as a schematic diagram of the cleavage I (release of BL enzyme) assay modality being used to detect the biomarker MMP1 (FIGS. 18B; 18D).

Figures 19A, 19B:
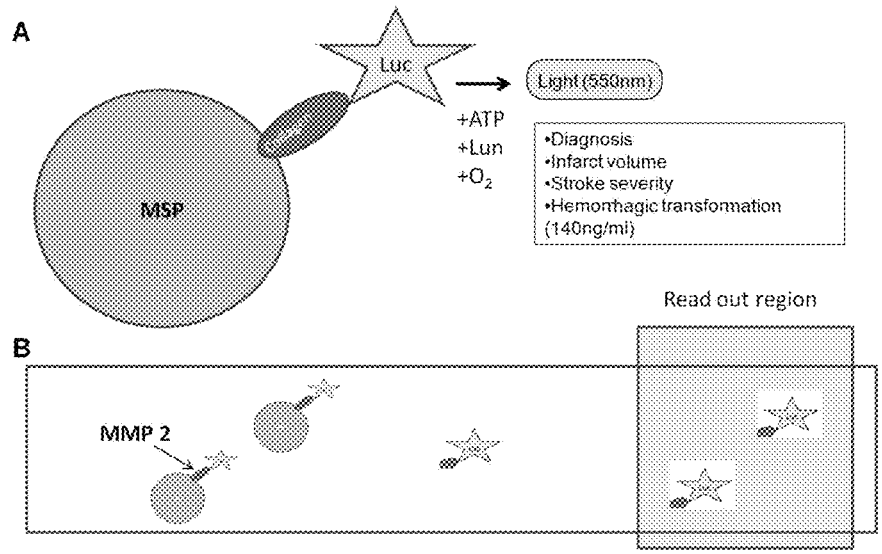

FIGS. 19A-19B show a schematic diagram of the protein assembly for the detection of matrix metalloproteinase ("MMP2") and clinical value of that detection (FIG. 19A), as well as a schematic diagram of the cleavage I (release of BL enzyme) assay modality being used to detect the biomarker MMP2 (FIG. 19B).

Figures 20A, 20B:
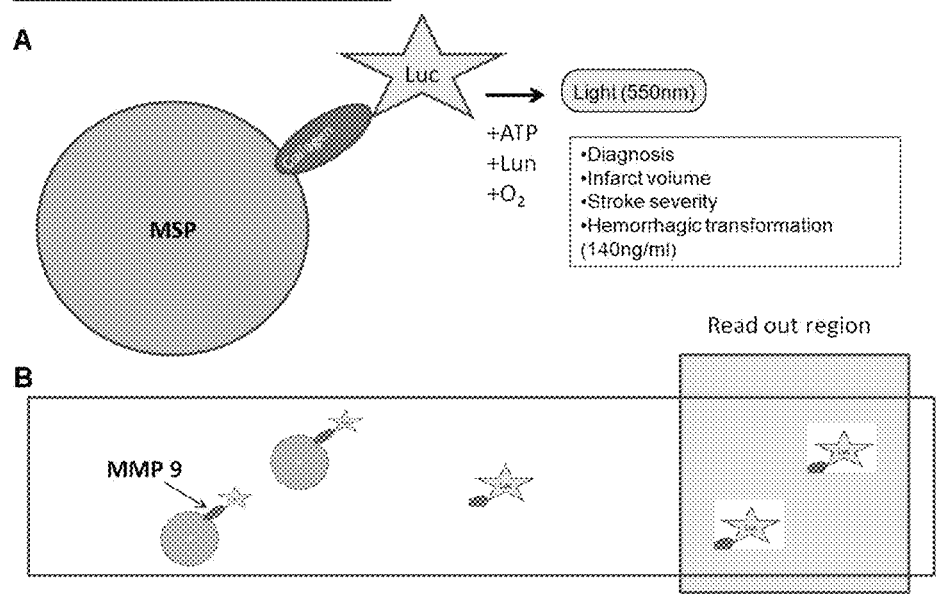

FIGS. 20A-20B show a schematic diagram of the protein assembly for the detection of matrix metalloproteinase ("MMP9") and clinical value of that detection (FIG. 20A), as well as a schematic diagram of the cleavage I (release of BL enzyme) assay modality being used to detect the biomarker MMP9 (FIG. 20B).

FIGS. 21A-21B show a schematic diagram of the protein assembly for the detection of activated protein C ("APC") and clinical value of that detection (FIG. 21A), as well as a schematic diagram of the cleavage I (release of BL enzyme) assay modality being used to detect the biomarker APC (FIG. 21B).

FIGS. 22A-22B show a schematic diagram of the protein assembly for the detection of chitotriosidase ("Cht") and clinical value of that detection (FIG. 22A), as well as a schematic diagram of the cleavage I (release of BL enzyme) assay modality being used to detect the biomarker Cht (FIG. 22B).

FIGS. 23A-23B show a schematic diagram of the protein assembly for the detection of tissue plasminogen activator and clinical value of that detection ("TPA") (FIG. 23A), as well as a schematic diagram of the cleavage I (release of BL enzyme) assay modality being used to detect the biomarker TPA (FIG. 23B).

FIGS. 24A-24B show a reaction schematic for the detection of glutathione S-transferase ("GST") and clinical value of that detection (FIG. 24A), as well as a schematic diagram of the cleavage II (release of BL substrate) assay modality being used to detect the biomarker GST (FIG. 24B).

FIGS. 25A-25B show a reaction schematic for the detection of calcium ($Ca^{2+}$) and clinical value of that detection (FIG. 25A), as well as a schematic diagram of the bioluminescent cofactor assay modality being used to detect the biomarker $Ca^{2+}$ (FIG. 25B).

FIG. 26 depicts an example of how a diagnostic device might use a colorimetric readout to detect the presence of multiple biomarkers. In this example, the presence of 5 biomarkers is interrogated and color changes in the reaction chambers from yellow to purple reveal the positive finding that all 5 were detected.

Figure 27A:
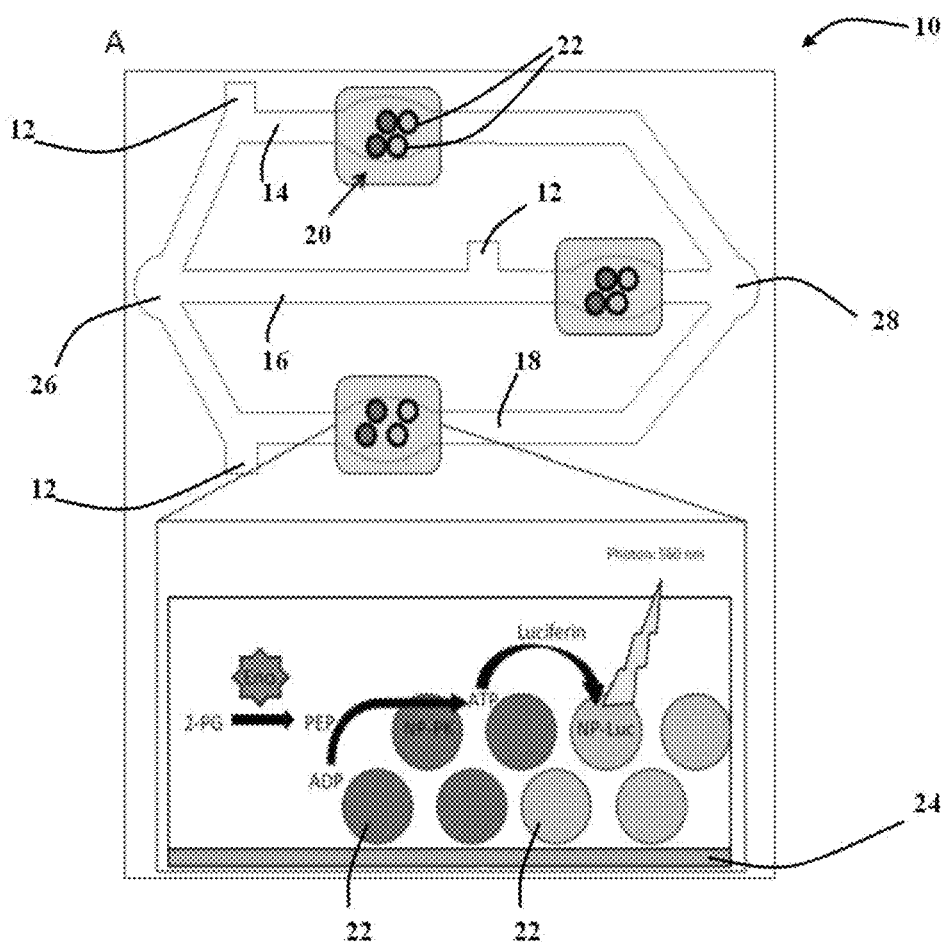
Figure 27B:
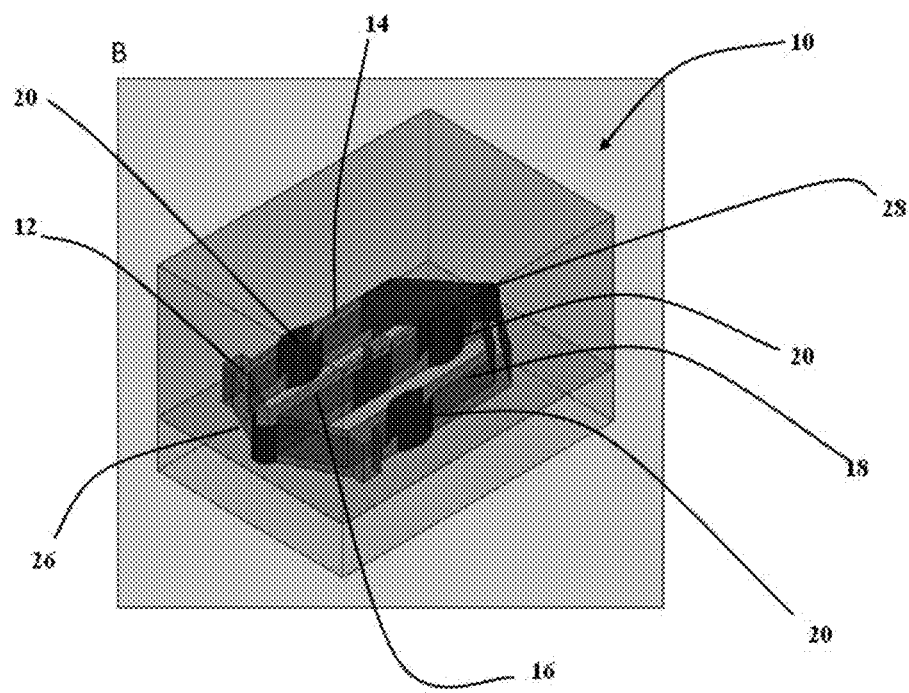

FIGS. 27A-27B show a schematic representation of an embodiment of an enzymatic assay according to the present invention, where the assay is carried out using a three-microchannel card to detect NSE (FIG. 27A). FIG. 27B shows a perspective view of a three-microchannel chip according to the present invention.

Figure 28:
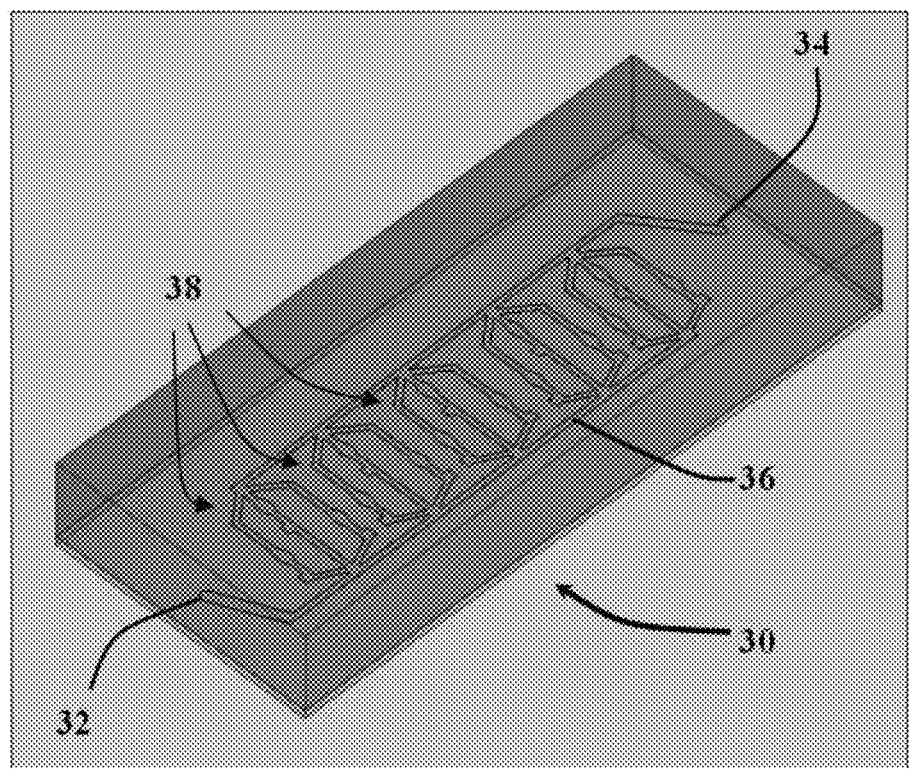

FIG. 28 shows a perspective view of an example of a multiplexed microchannel card for the detection of five biomarkers according to one embodiment of the present invention, each having 3 channels (positive control, negative control, and experimental or test channel).

Figure 29A:
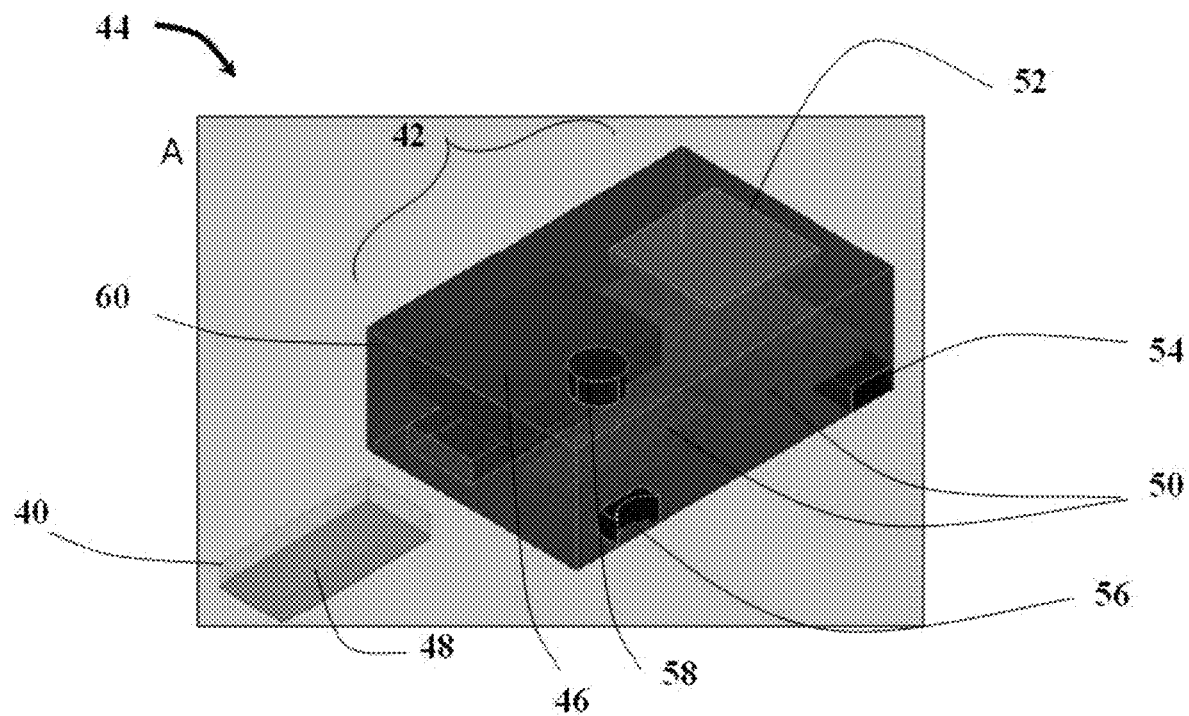
Figures 29B, 29C:
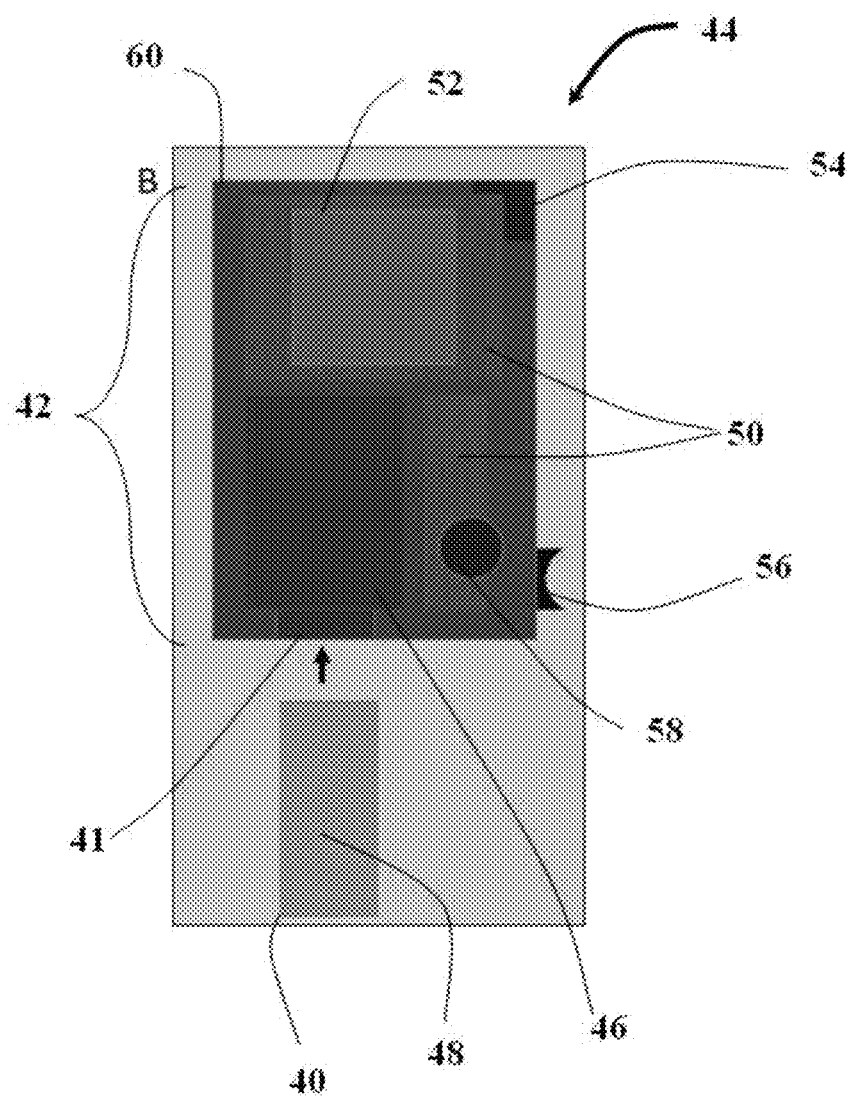

FIGS. 29A-29C show a perspective view of one example of how a PoCT card-reader system diagnostic for neural injury based on tethered enzyme technology according to one embodiment of the present invention would appear and function. FIG. 29A is a perspective view showing one embodiment of a device (e.g., a microfluidic card with a detector unit) according to the present invention. FIG. 29B is a perspective view showing an example of a PoCT detection device for use with a microchannel-based card.

FIG. 29C is an exemplary display layout for the PoCT detection device, showing data for a hypothetical patient sample. Here, biomarkers that are diagnostic for a stroke are separated from those that are prognostic. Depending on the condition being diagnosed and the panel of biomarkers, the data could either be grouped to give a composite assessment of risk/health status, be displayed individually, or both.

Figures 30A, 30B:
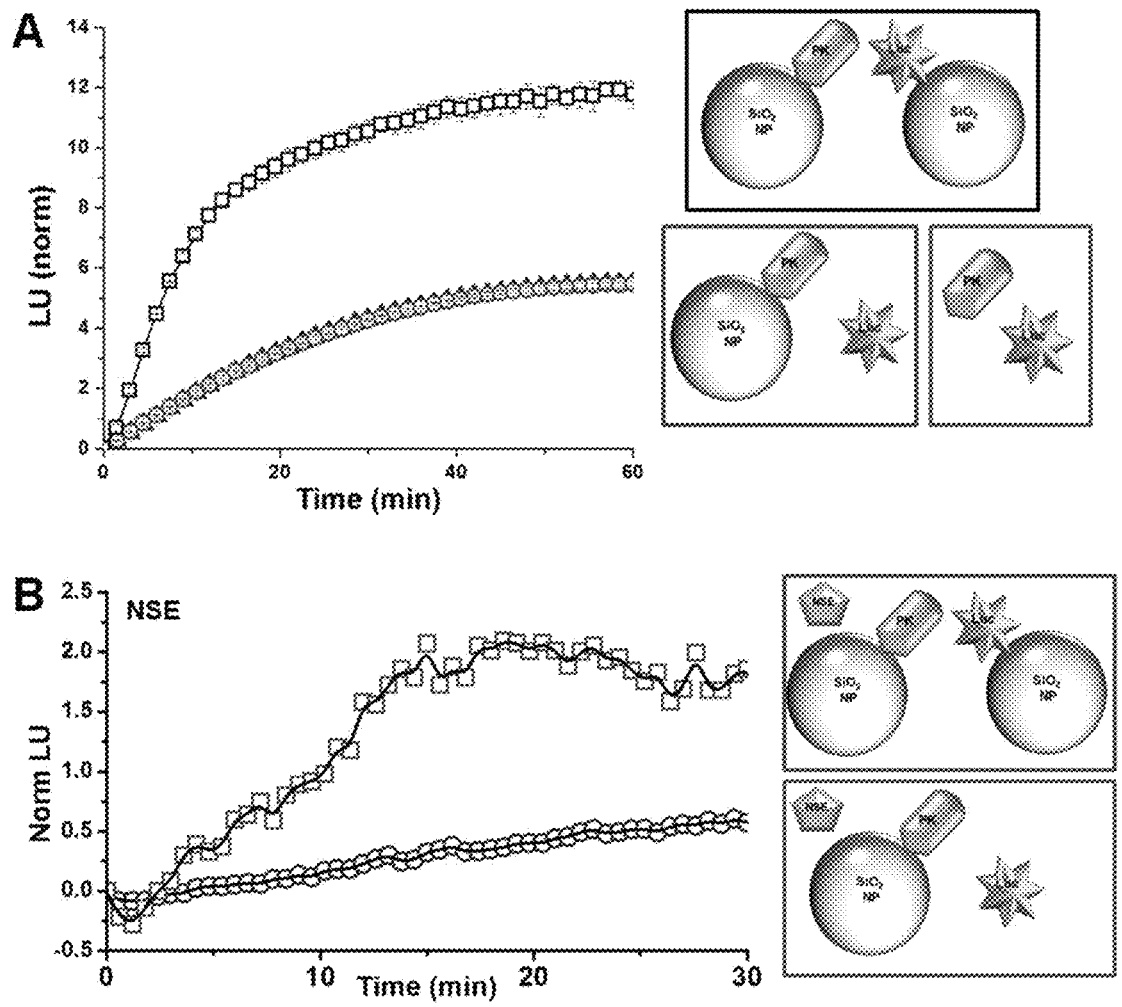

FIGS. 30A-30B show results which demonstrate the increased coupling efficiency of pyruvate kinase (PK) and luciferase (Luc) when tethered to nanoparticles (NPs). Silica nanoparticles ($SiO_2$ NP) were used. FIG. 30A shows NP–PK and NP–Luc (boxes; top inset schematic) reveal increased coupled activity versus NP–PK+soluble Luc (circles; bottom, left inset schematic) or PK+Luc in solution (triangles; bottom, right inset schematic). FIG. 30B shows results demonstrating that having both PK and Luc immobilized on separate NPs (black boxes; top inset schematic) increases sensitivity in detection of soluble NSE versus having only one enzyme tethered (circles; bottom inset schematic).

Figure 31A:
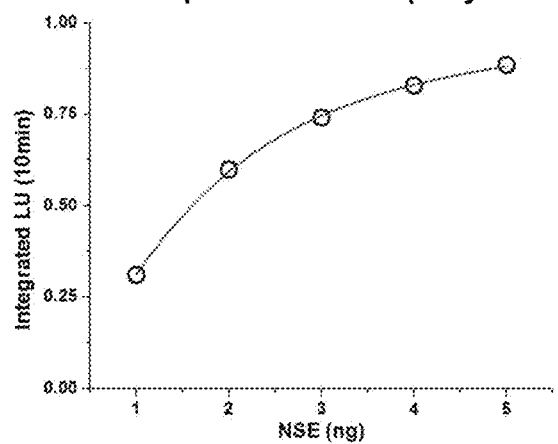
Figure 31B:
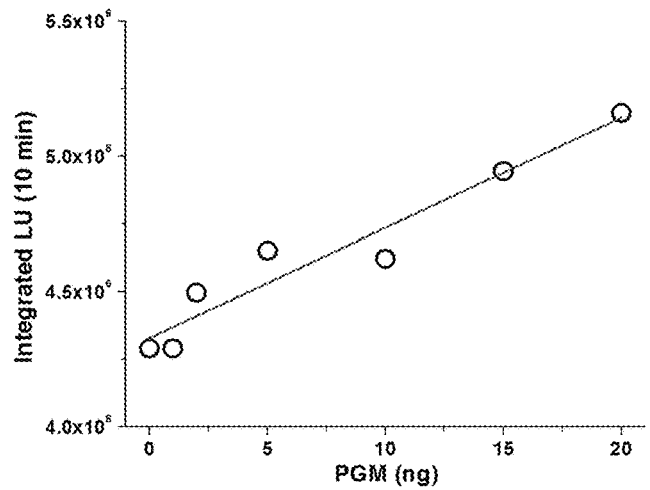
Figure 31C:
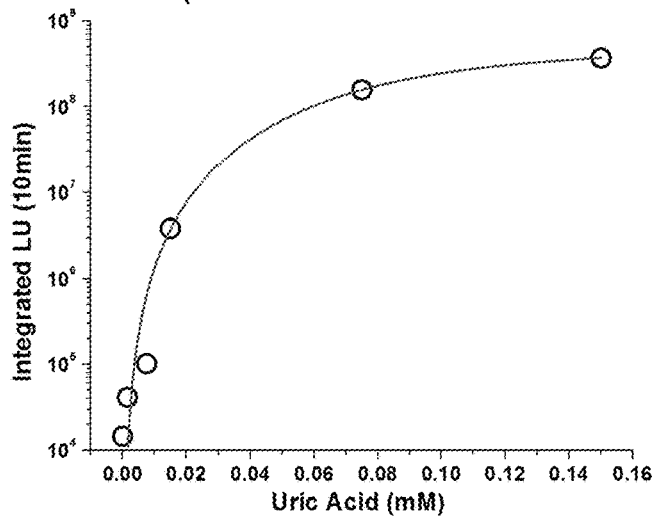
Figure 31D:
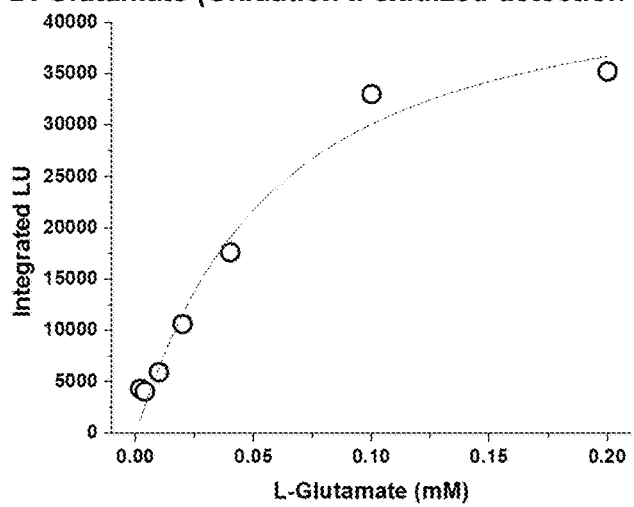
Figure 31E:
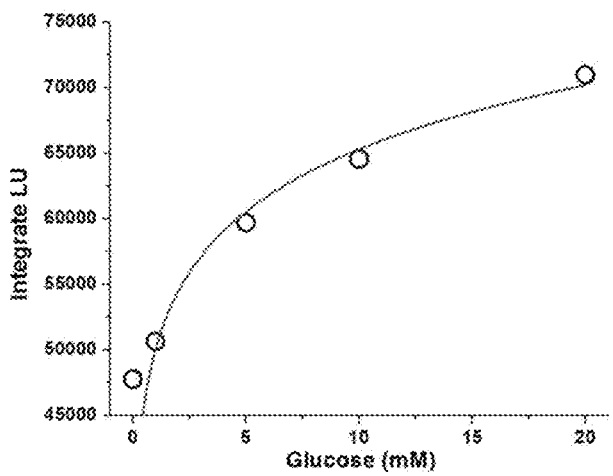
Figure 31F:
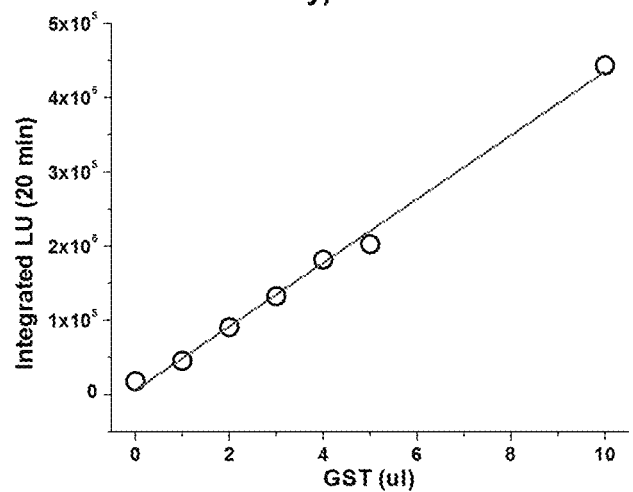
Figure 31G:
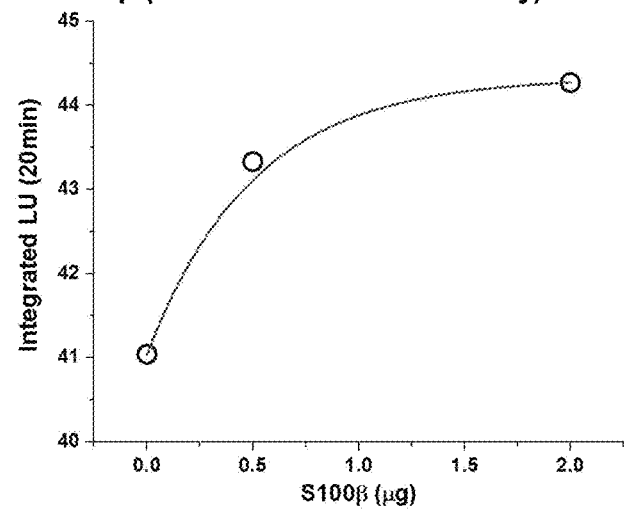

FIGS. 31A-31H are graphs showing results of in solution detection assays performed with human plasma spiked with one or more biomarkers taken from each assay modality. FIGS. 31A-31H represent example biomarkers which were tested: NSE (enzymatic) (FIG. 31A); PGM (enzymatic) (FIG. 31B); UA (oxidation I, oxidized) (FIG. 31C); glutamate (oxidation I, oxidized) (FIG. 31D); glucose (oxidation I, oxidized) (FIG. 31E); GST (cleavage II, release of BL substrate) (FIG. 31F); S100β (affector) (FIG. 31G); and Ca$^{2+}$ (BL cofactors) (FIG. 31H).

FIGS. 32A-32B are graphs showing data from experiments in a rat stroke model using tethered enzymes to detect biomarkers for neural injury. FIG. 32A shows results from detection of NSE using the enzymatic assay modality at time points ranging from one hour before CNS blood vessel occlusion (t-1) to the time just following occlusion (t0), to 1, 3, and 6 hours post-occlusion (t1, t3, and t6, respectively). FIG. 32B shows results from quantification of NSE using the enzymatic assay modality at the 6 hour time point, comparing NSE values from experimental versus sham-operated controls. Asterisks denote $p<0.05$ (**) and $p<0.1$ (*), using students t-test.

Figures 33A, 33B:
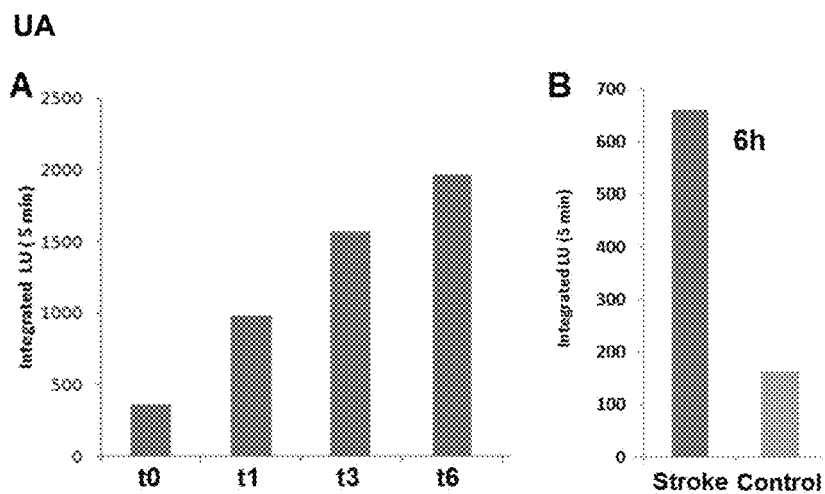

FIGS. 33A-33B are graphs showing data from experiments in a rat stroke model using enzymes to detect biomarkers for neural injury. FIG. 33A shows results from the detection of UA using the oxidation I. oxidized assay modality at time points ranging from the time immediately following CNS blood vessel occlusion (t0) to 1, 3, and 6 hours post-occlusion (t1, t3, and t6, respectively). FIG. 33B shows results from comparison of serum UA between stroke and sham-operated controls, using the oxidation I (oxidized) assay modality, at the 6 hour time point.

Figures 34A, 34B:
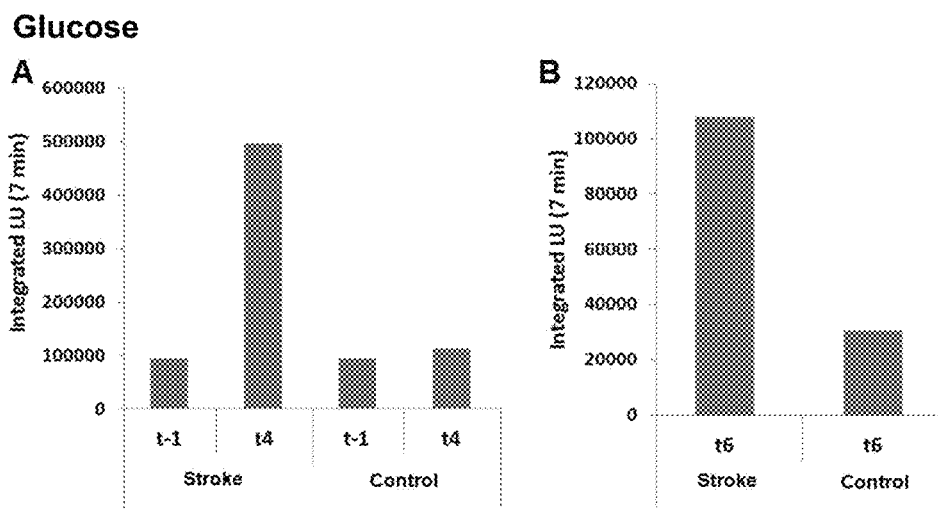

FIGS. 34A-34B are graphs showing data from experiments in a rat stroke model using enzymes to detect biomarkers for neural injury. FIG. 34A shows results of the detection of glucose using the oxidation I. oxidized assay modality at time points ranging from one hour before CNS blood vessel occlusion (t-1) to 4 hours post-occlusion (t4). FIG. 34B shows results from comparison of serum glucose between stroke and sham-operated controls, using the oxidation I (oxidized) assay modality, at the 6 hour time point (t6).

Figure 35:
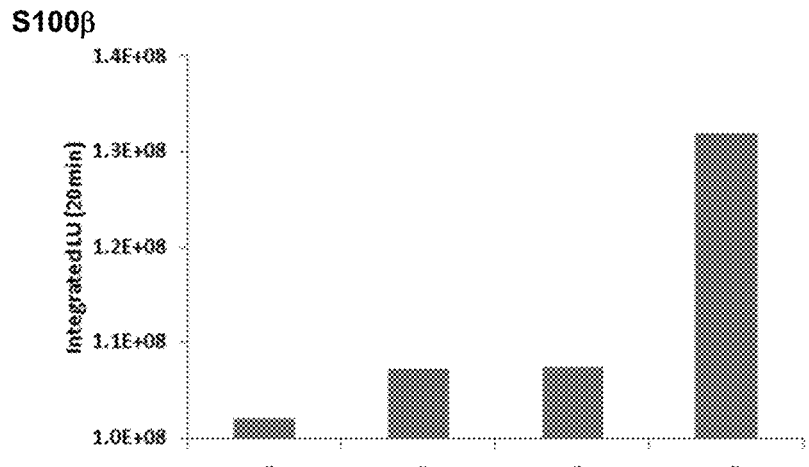

FIG. 35 is a graph showing data from a rat stroke model using enzymes to detect biomarkers for neural injury. The graph shows results from the detection of S100β using the affector assay modality at time points ranging from immediately after CNS blood vessel occlusion (t0) to 1, 3, or 6 hours post-occlusion (t1, t3 and t6, respectively).

Figures 36A, 36B:
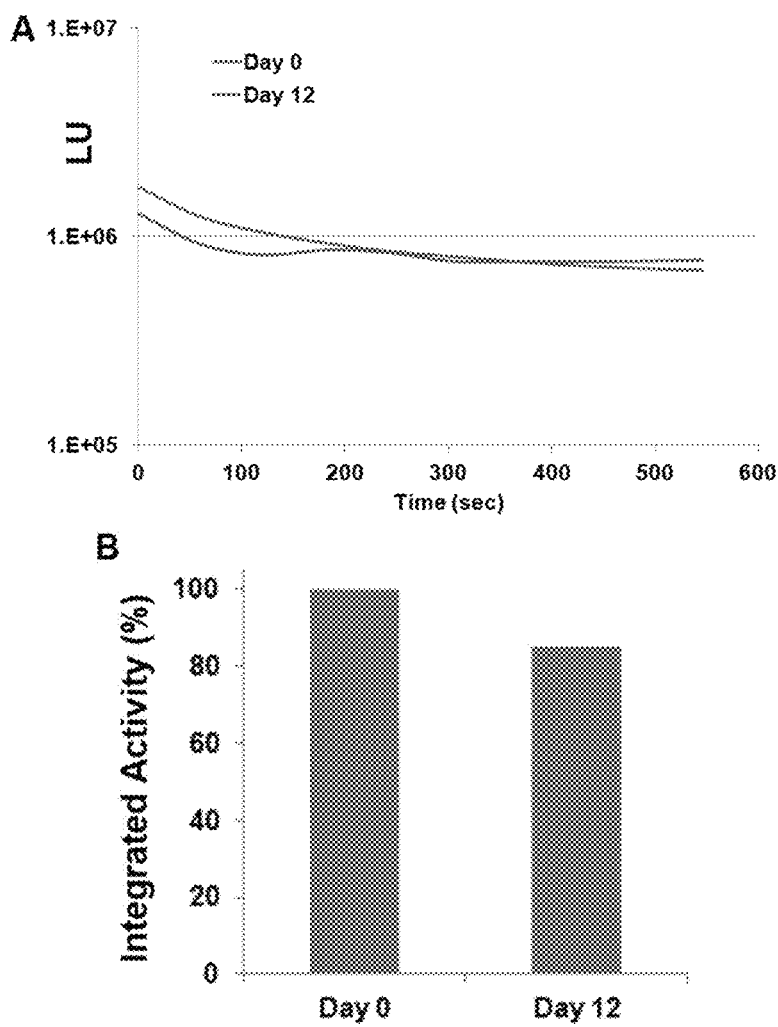

FIGS. 36A-36B are graphs showing results which demonstrate that a lyophilized reaction mix including Luc tethered to magnetic, silica-coated nanoparticles retained high activity after 2 weeks of storage at $-20°$ C.

DETAILED DESCRIPTION OF THE INVENTION

The present invention relates to methods of detecting a biomarker (e.g., a neural injury biomarker). The method includes subjecting a biological sample to an assay according to the present invention that produces a measurable signal and detecting the measurable signal. The presence or absence of the measurable signal indicates the presence or absence of the biomarker in the sample.

As used herein, the term "injury or neural injury" is intended to include a damage which directly or indirectly affects the normal functioning of the central nervous system ("CNS") or peripheral nervous system ("PNS"). For example, the injury can be damage to retinal ganglion cells; a traumatic brain injury; a stroke related injury; a cerebral aneurism related injury; demyelinating diseases such as multiple sclerosis; a spinal cord injury, including monoplegia, diplegia, paraplegia, hemiplegia and quadriplegia; a neuroproliferative disorder or neuropathic pain syndrome. Examples of CNS injuries or disease include traumatic brain injury ("TBI"), stroke, concussion (including post-concussion syndrome), cerebral ischemia, neurodegenerative diseases of the brain such as Parkinson's disease, Dementia Pugilistica, Huntington's disease and Alzheimer's disease, brain injuries secondary to seizures which are induced by radiation, exposure to ionizing or iron plasma, nerve agents, cyanide, toxic concentrations of oxygen, neurotoxicity due to CNS malaria or treatment with anti-malaria agents, malaria pathogens, injury due to trypanosomes, and other CNS traumas. Examples of PNS injuries or diseases include neuropathies induced either by toxins (e.g., cancer chemotherapeutic agents), diabetes, peripheral trauma or any process that produced pathological destruction of peripheral nerves and/or their myelin sheaths.

In one embodiment according to the present invention, the method relates to the detection of a biomarker indicative of stroke.

The term "biomarker" refers to biologically relevant elements that are released into a biofluid (e.g., bloodstream, cerebral spinal fluid, etc.) coincident with, or after, some pathological event or condition.

Several biomarkers for neural injury (shown in FIG. 1) have been reported to confer diagnostic and/or prognostic utility. Assays according to the present invention are suitable to detect such neural injury biomarkers. These will be used as examples for the translation of our tethered enzyme-based methods into systems that provide diagnostic and prognostic information.

Suitable biological samples in accordance with the present invention include a whole blood sample, blood serum sample, blood plasma sample, or a cerebrospinal fluid sample.

Assays according to the present invention are suitable to detect neural injury biomarkers. In one embodiment, the neural injury biomarker is selected from the group consisting of S100β, glial fibrillary acidic protein ("GFAP"), neuron specific enolase ("NSE"), phosphoglycerate mutase ("PGM"), nucleoside-diphosphate kinase A ("NDK-A"), spermine, uric acid, glutamate, arginine, glycine, glucose, homocysteine, iron, poly amine oxidase ("PAO"), spermine oxidase ("SMO"), matrix metalloproteinase-1 ("MMP-1"), matrix metalloproteinase-2 ("MMP-2"), matrix metalloproteinase-9 ("MMP-9"), activated protein C ("APC"), chitotriosidase, tissue plasminogen activator ("TPA"), glutathione s-transferase ("GST"), $Ca_{2+}$, acrolein, and combinations thereof.

Assays according to the present invention relate to enzymatic reaction-based detection assays. Such assays are referred to herein as, for example, assays, assay modalities, detection modalities, assay detection modalities, modalities, and the like.

Enzymatic reaction-based detection assays present a class of biomarker recognition technology with significant advantages arising from the catalytic nature of enzymes, namely increased sensitivity and speed. Biomarker detection via enzymatic reactions has been demonstrated previously for, e.g., NSE (Wevers et al., "A Bioluminescent Assay for Enolase (EC 4.2.1.11) Activity in Human Serum and Cerebrospinal Fluid," *Clin. Chim. Acta* 135(2):159-68 (1983) and Viallard et al., "An Ultramicro Bioluminescence Assay of Enolase: Application to Human Cerebrospinal Fluid," *Neurochem. Res.* 10(12):1555-66 (1985), which are hereby incorporated by reference in their entirety). However, previously, these assays were carried out using enzymes in solution, whereas the currently described technology utilizes, in certain embodiments, immobilized enzymes (e.g., on various surfaces), providing significant advantages as indicated in the Examples described herein. Further, in the past, the use of enzymes to detect biomarkers was largely limited to those biomarkers with enzymatic activity. Alternatively, enzymes were used as signal amplifiers after a capture-based step of biomarker detection (e.g., antibodies would detect the biomarker and then either those antibodies or a secondary antibody would be conjugated with an active enzyme or enzyme substrate).

The components of the assay according to the present invention, e.g., enzymes, substrates, and other reagents, may be immobilized. Such components may be immobilized by binding the components to one or more supports. Suitable supports include organic or inorganic materials and may be of any suitable size or shape (e.g., scaffolds sheets, platforms, and/or nanoparticles). Tethering or immobilizing the components of the assays according to the present invention serves to, for example, confine them spatially as well as to enhance their stability and/or function in carrying out, for example, a cascading or sequential reaction as part of the particular assay. In certain embodiments, the support materials include, e.g., nucleotide sequences or gels. In certain embodiments, the enzymes or components of the assays according to the present invention may be immobilized on or tethered to, for example, a nanoparticle or the luminal surface of a channel (e.g., a microfluidic channel) of a support material such as a platform.

Several techniques can be used to immobilize components of an assay according to the present invention (e.g., enzymes) on surfaces. For example, components may be attached non-specifically or be bound through specific, though non-oriented, chemical reactions (such as carboxyamide binding). Oriented enzyme immobilization may also be used in accordance with methods of the present invention. Oriented enzyme immobilization confers several advantages including, for example, positioning a binding tag (e.g., an affinity tag) so that the activity and stability of the tethered enzyme is optimized (see Mukai et al., "Sequential Reactions of Surface-Tethered Glycolytic Enzymes," *Chem. Biol.* 16(9):1013-20 (2009), which is hereby incorporated by reference in its entirety).

One example of how an enzyme involved in biomarker detection would be tethered to a surface is the use of oriented immobilization. In certain embodiments of the assays according to the present invention, recombinant enzymes or assay components which are involved in the assay's reactions are engineered with an affinity tag, enabling them to bind to a surface such as silica or nickel, or a component of a surface such as nickel-nitrilotriacetic acid. For example, an affinity tag could be attached at the amino or carboxy terminus of a protein to be immobilized, or be embedded within the protein to be immobilized. Optimal location of the tethering domain will depend upon the nature and location of the enzyme's catalytic domain(s), substrate binding domain(s) and any conformational changes the enzyme must make. Such recombinant enzymes are then, in one embodiment, bound to a support, platform, or scaffold (e.g., MSPs, as depicted in FIGS. 2B, 3B, 4B, 5B, 6B, 7B, 8B, 9B, 10B, 11B, 12B, 13B, 14B, 15B, 16B, 17B, 17D, 18A-18D, 19A-19B, 20A-20B, 21A-21B, 22A-22B, 23A-23B, 24B, and 25B).

The surfaces acting as support, platform, or scaffold can take multiple forms, including, for example, various nanoparticles, or strands of nucleic acids, and may include various geometries.

In certain embodiments according to the present invention, the support is a nanoparticle. As used herein, the term "nanoparticle" refers to any particle the average diameter of which is in the nanometer range, i.e., having an average diameter up to 1 µm. The nanoparticle used can be made of any suitable organic or inorganic matter that will be known to those of ordinary skill in the art. For example, nanoparticles may be composed of any polymer, iron (II,III) oxide, gold, silver, carbon, silica, CdSe and/or CdS. In one embodiment the nanoparticle is a magnetic nanoparticle. In one embodiment, the nanoparticle is a magnetic, silica-coated nanoparticle ("MSP").

In addition to nanoparticles (NP), supports or scaffolds of different materials can be in the form of rods, planar surfaces, graphene sheets, nanotubes, DNA scaffolds, gels, or inner channel walls of a microchannel of a larger support. Quantum dots are also contemplated for use as a support in accordance with the present invention. However, in certain embodiments of assays according to the present invention quantum dots may not be desirable. Thus, in certain embodiments, the support does not include a quantum dot or a material that itself produces a measurable signal. Enzyme immobilization can be attained via non-specific binding, chemical modifications, affinity tags, or other conjugation techniques.

In certain embodiments, the present invention uses enzymes in the biomarker detection steps as well as in amplification of a measurable signal. The measurable signal according to the present invention may be any suitable measurable signal. In one embodiment, the measurable signal is a photometrically detectable signal, an electrochemically detectable signal, a colorimetrically detectable signal, a fluorescent signal, an antibody, an oligomarker, or an oligonucleotide molecule. In one embodiment, the measurable signal is a photometrically detectable signal or a colorimetrically detectable signal. It will be understood that variations of the assays according to the present invention could result in colorimetric readouts. For example, replacing the HRP luminescent substrate, luminol, with chromogenic substrates (e.g., TMB (3,3',5,5'-tetramethylbenzidine), DAB (diaminobenzidine), or ABTS (2,2'-azino-bis(3-ethylbenzthiazoline-6-sulfonic acid)) will result in a colorimetric readout that could be detected directly in, for example, an assay employing the oxidative assay modality. As another example, for coupled reactions that utilize PK to produce pyruvate (e.g., for detection of NSE or PGM), pyruvate oxidase (POx) might replace luciferase ("Luc") to produce a colorimetric reaction. Similarly, to obtain colorimetric detection for the cleavage assay modality, Luc can be replaced with HRP. For the detection of S100β, PGK and Luc may be omitted from the assay and the NADH produced by GAPDH utilized to reduce the chromogen tetrazolium chloride, generating a change in color.

Suitable signal-transducing molecules according to the present invention include any molecules capable of producing a measurable signal. In one embodiment, the signal-transducing molecule of an assay according to the present invention is selected from the group consisting of firefly luciferase, Renilla luciferase, horseradish peroxidase, pyruvate oxidase, and a chromogen (e.g., tetrazolium chloride).

In certain embodiments of assays according to the present invention, exogenous cofactors and substrates are provided (e.g., pre-loaded into a microchannel) such that as the plasma or serum sample is subject to the assay (e.g., moves up the microchannel), all required components of the reaction are brought together (e.g., into a reaction chamber or portion of the channel). In this way, the reaction will progress only if the biomarker is present in the sample (excepting for any positive control lanes, in which case a recombinant form of the biomarker itself would be present in that channel).

In various embodiments, the reagents, substrates, and co-factors are for a bioluminescent reaction. The reagents may be lyophilized, liquid, solid, and/or the like. Further, the reagents, substrates, and co-factors may be loaded into systems (e.g., channels) according to the present invention at or about the time of the introduction of the biological sample. Alternative embodiments comprise a step of providing or loading, in the case of the systems according to the present invention, a lyophilized reagent, substrate, and/or co-factor prior to subjecting a biological sample to an assay according to the present invention. In the case of a system according to the present invention, the preloading of these components allows for storage of the system so that it may be "used off the shelf." The reagent may be stabilized to allow for a longer duration of storage prior to use.

In one embodiment according to the present invention, the assay includes an affector assay detection modality. This approach is designed to detect biomarkers that can affect the activity of some enzyme of interest (e.g., S100β). Activity of the enzyme of interest is then coupled to a BL protein in the same way as in the enzymatic assay detection modality. The difference between the two methods is that in this case the biomarker will either enhance or decrease the activity of an enzyme, with the change in signal correlating to the amount of biomarker in the system. In this assay, the biomarker itself is not providing the enzyme activity. FIGS. 2A-2B and 3A-3B provide schematic diagrams of two embodiments of an affector assay detection modality. Detection of the diagnostic biomarker S100β, which is released in neural damage, and predicts infarct volume and stroke severity, is used as an example.

Figures 2A, 2B:
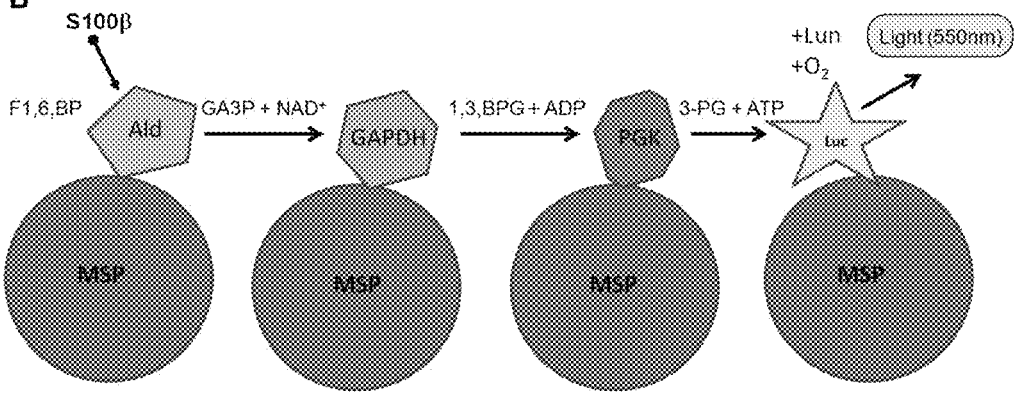
FIGS. 2A-2B show a reaction schematic for the detection of S100β and clinical value of that detection (FIG. 2A) and a schematic diagram of the affector assay modality being used to detect the biomarker S100β according to one embodiment of the present invention (FIG. 2B).

With reference to FIGS. 2A-2B, in the depicted assay embodiment, S100β enhances or promotes the activity of the enzyme aldolase ("Ald"). In one embodiment, recombinant Ald is expressed with a binding tag on one end, tethering it to a suitable substrate (e.g., a magnetic, silica-coated nanoparticle ("MSP")), though other substrates and means of tethering are possible. Similarly, glyceraldehyde 3-phosphate dehydrogenase (GAPDH), phosphoglycerate kinase (PGK) and Firefly Luciferase ("Luc") could be immobilized on separate MSPs (as shown in this embodiment), or in groups of two or more enzymes on individual MSPs. Note that for all tethered enzymes, the substrate and means of attachment might vary. In addition to the enzymes, fructose 1,6-bisphosphate, $NAD^+$, ADP, D-luciferin and other cofactors and reagents may be provided for this assay. If performed within a microchannel card, these additional assay components may be preloaded into such a device (e.g., a pre-loading chamber) to participate in the assay. In the depicted embodiment, if S100β is present, it will stimulate aldolase and the conversion of fructose 1,6-bisphosphate to glyceraldehyde 3-phosphate (GA3P). This will increase the passage of substrate to GAPDH and PGK, therefore increasing phosphorylation of ADP to ATP. Consequently, increased levels of ATP will be available for Luc, resulting in an increase in light emission. In this assay, the increase of a measurable signal (e.g., light) will correlate to the amount of S100β in the system.

Figures 3A, 3B:
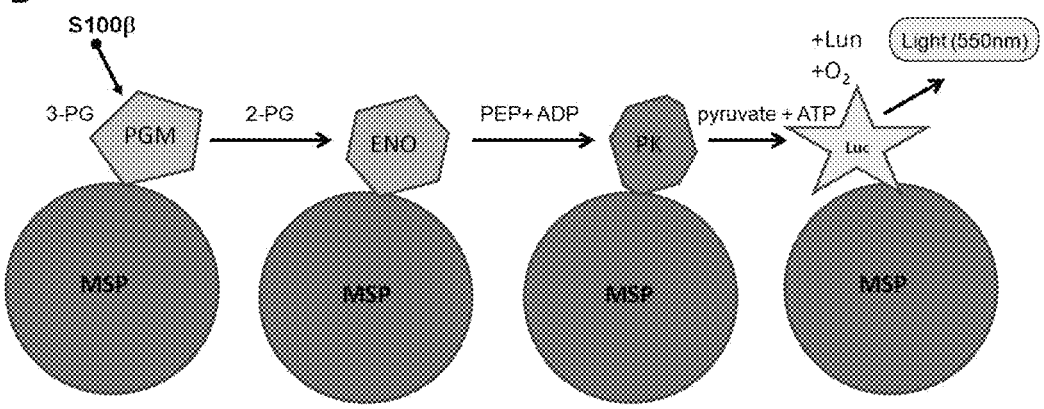
FIGS. 3A-3B show a reaction schematic for the detection of S100β and clinical value of that detection (FIG. 3A) and a schematic diagram of the affector assay modality being used to detect the biomarker S100β according to one embodiment of the present invention (FIG. 3B).
Figures 4A, 4B:
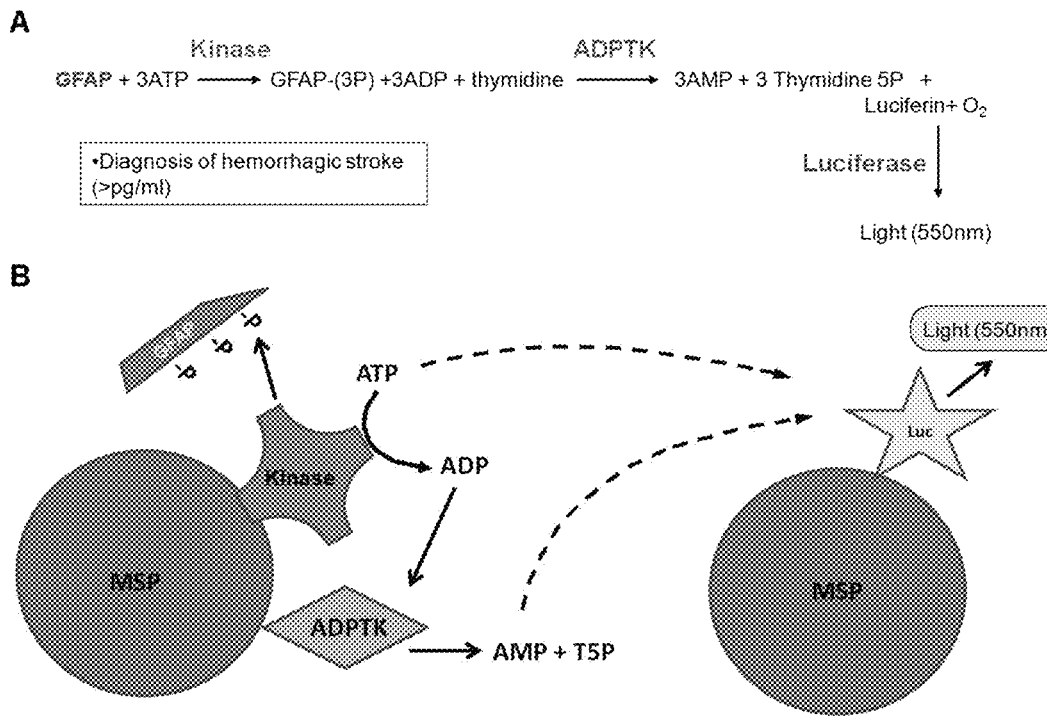
FIGS. 4A-4B show a reaction schematic for the detection of GFAP according to one embodiment of the assay according to the present invention and clinical value of that detection (FIG. 4A), as well as a schematic diagram of the phosphorylation assay modality being used to detect the biomarker GFAP (FIG. 4B). In this reaction, a decrease in luminescence is measured (for example, in the readout zone) versus that in a negative control.

With reference to FIGS. 3A-3B, in the depicted assay embodiment, S100β enhances or promotes the activity of the enzyme phosphoglyceromutase ("PGM"). In this embodiment, enolase, pyruvate kinase, and the signal-transducing molecule Luc are provided. In one embodiment, recombinant PGM, enolase, and/or pyruvate kinase are expressed with a binding tag on one end to allow tethering to a suitable substrate (e.g., a magnetic, silica-coated nanoparticle ("MSP")), though other substrates and means of tethering are possible. This assay also includes providing 3-phosphoglycerate, D-luciferin, and $O_2$. In the depicted embodiment, if S100β is present, it will stimulate PGM to increase the 3-phosphoglycerate to 2-phosphoglycerate conversion rate, the 2-phosphoglycerate reacting with enolase to produce phosphoenolpyruvate ("PEP") and ADP with the PEP and ADP reacting with pyruvate kinase to produce pyruvate and ATP. Consequently, increased levels of ATP will be available for Luc, resulting in an increase in light emission. In this assay, the increase of a measurable signal (e.g., light) will correlate to the amount of S100β in the system.

In one embodiment according to the present invention, the assay includes a phosphorylation assay detection modality. In one embodiment of this assay detection modality, the biomarker (e.g., glial fibrillary acidic protein ("GFAP")) is a target for a protein kinase (e.g., rho-associated protein kinase ("ROCK")) in a process that utilizes ATP molecules. It will be understood that any suitable GFAP-phosphorylating kinase may be used in accordance with this embodiment. In this embodiment, the readout of luminescence depends on the concentration of ATP following the phosphorylation of the target protein. Higher GFAP biomarker concentration in a sample subjected to this assay will result in increased ATP consumption and thus reduced luminescence.

Figures 5A, 5B:
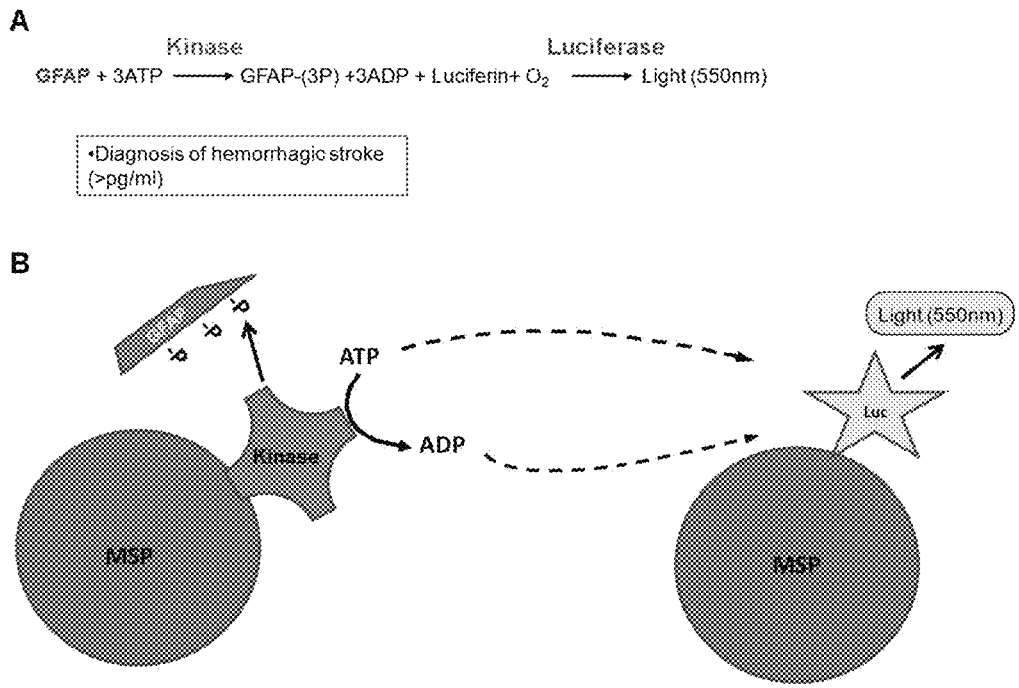
FIGS. 5A-5B show a reaction schematic for the detection of GFAP according to one embodiment of the assay according to the present invention and clinical value of that detection (FIG. 5A), as well as a schematic diagram of the phosphorylation assay modality being used to detect the biomarker GFAP (FIG. 5B). In this reaction, a decrease in luminescence is measured (for example, in the readout zone) versus that in a negative control.
Figures 8A, 8B:
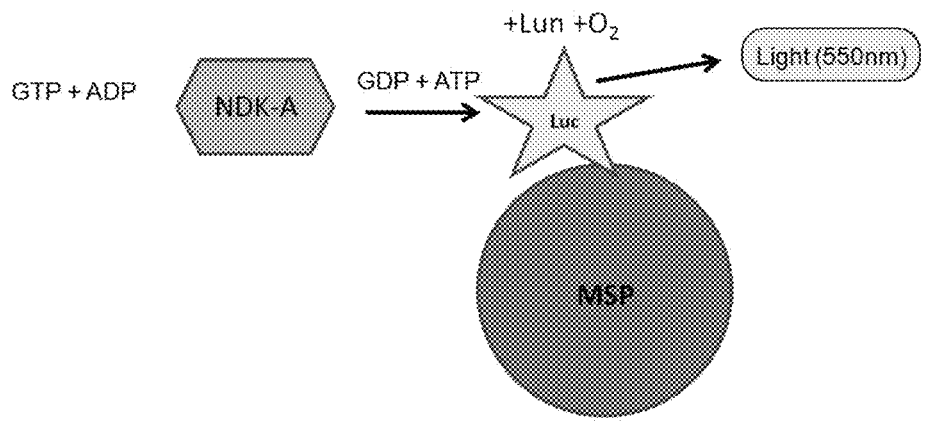
FIGS. 8A-8B show a reaction schematic for the detection of Nucleoside-Diphosphate Kinase (NDK-A) and clinical value of that detection (FIG. 8A), as well as a schematic diagram of the enzymatic assay modality being used to detect the biomarker NDK-A (FIG. 8B).

FIGS. 4A-4B and 5A-5B provide schematic diagrams of embodiments of the phosphorylation assay detection modality. Detection of the biomarker GFAP, which is increased in cases of hemorrhagic stroke, and therefore is used as a biomarker to differentiate between hemorrhagic and ischemic strokes, is presented as an example. In this embodiment, recombinant ROCK and ADP-thymidine kinase (ADPTK) are immobilized singly or in combination on MSPs via silica-binding tags, though other substrates and means of tethering are possible. Thymidine, D-luciferin, ATP and cofactors are also provided for the assay. If performed within a microchannel card, these additional assay components may be preloaded into such a device (e.g., a pre-loading chamber) to participate in the assay. If GFAP is present in a sample, it will be phosphorylated by ROCK with ATP producing ADP which will then be utilized by ADPTK and thymidine to produce AMP and thymidine 5'-phosphate (T5P). The conversion of ATP to AMP by ROCK and ADPTK will decrease the amount of ATP available to Luc, therefore decreasing signal output. The decreased signal can be correlated to the amount of GFAP in the system. It will be understood that the use of ADPTK is optional in this assay. Thus, an alternative embodiment excluding the use of ADPTK and thymidine is shown in FIGS. 5A-5B.

In one embodiment according to the present invention, the assay includes an enzymatic assay detection modality. This approach is useful to detect enzyme biomarkers (e.g., neuron specific enolase ("NSE"), phosphoglyceromutase ("PGM"), and nucleoside diphosphate kinase A ("NDK-A")) that are linked through coupled reactions to a signal transducing molecule (e.g., firefly Luc through the production of ATP).

FIGS. 6A-6B, 7A-7B, and 8A-8B provide schematic diagrams of embodiments of the enzymatic assay detection modality. Detection of the biomarker NSE, which is diagnostic for neural injury and gives information on infarct volume and stroke severity (Kernagis and Laskowitz, "Evolving Role of Biomarkers in Acute Cerebrovascular Disease," *Ann. Neurol.* 71(3):289-303 (2012), which is hereby incorporated by reference in its entirety) is used as an example in FIGS. 6A-6B. NSE is released from neurons upon cell death and is a well-studied biomarker. As shown in FIG. 6B, in the depicted embodiment, pyruvate kinase ("PK") and firefly luciferase ("Luc") are tethered to separate nanoparticles via affinity peptides such as silica-binding peptides, though other substrates and means of attachment are possible. 2-phosphoglycerate ("2PG"), ADP, D-luciferin and cofactors (e.g., magnesium) are provided for the assay. If performed within a microchannel card, these additional assay components may be preloaded into such a device (e.g., a pre-loading chamber) to participate in the assay. If NSE is present, a sequential reaction will occur. One sequential reaction is shown in FIGS. 6A and 6B. As shown, NSE will convert 2PG to phosphoenolpyruvate ("PEP") which will then be converted to pyruvate by the tethered PK, producing ATP in the process. In conjunction with D-luciferin, the ATP will then be used by tethered Luc to make oxyluciferin and emit a photon of light. The amount of light emitted is directly proportional to the amount of ATP in the system, thereby corresponding to the amount of NSE in the system. Light emitted may, in one embodiment, be read quantitatively and/or qualitatively by a photodetector positioned to capture that emitted signal.

With reference to FIGS. 7A-7B, detection of the biomarker PGM is depicted. If PGM is present, a sequential reaction will occur. One sequential reaction is shown in FIGS. 7A and 7B. As shown, 3-phosphoglycerate, enolase, and pyruvate kinase are provided. This embodiment also includes providing D-luciferin and $O_2$, if PGM is present in the biological sample, a sequential reaction will occur. As shown, PGM will react with the 3-phosphoglycerate to produce 2-phosphoglycerate, the 2-phosphoglycerate reacting with enolase to produce PEP and ADP, with the PEP and ADP reacting with pyruvate kinase to produce pyruvate and ATP. The ATP will then react with luciferase to produce a measurable signal With reference to FIGS. 8A-8B, detection of the biomarker PDK-A is depicted. In the depicted embodiment, luciferase, GTP, ADP, D-luciferin and $O_2$, wherein the D-luciferin and $O_2$ are contacted with the biological sample during said contacting under conditions effective to permit a sequential reaction, whereby the NDK-A, if present in the biological sample, will react with the GTP and ADP to produce GDP and ATP, said ATP reacting with luciferase to produce a measurable signal.

In one embodiment the assay includes an oxidative assay detection modality. This modality encompasses two sets of methods or assays to detect biomarkers having different oxidative qualities. "Oxidative I, oxidized" includes biomarkers that can be oxidized (e.g., spermine, uric acid ("UA"), glutamate, arginine, glycine, glucose, homocysteine and iron). "Oxidative II, oxidase" includes biomarkers that are themselves oxidases (e.g., total polyamine oxidase ("PAO") and/or spermine oxidase ("SMO")). Both types of biomarkers utilize an oxidation reaction which will release $H_2O_2$ that can be utilized by an enzyme such as horseradish peroxidase ("HRP") to produce light. In the case of oxidative I biomarkers, the respective oxidase and HRP can be engineered with binding tags and bound to either separate scaffolds or the same scaffold. For oxidative II biomarkers, the HRP may be tethered or immobilized to a support.

Figures 9A, 9B:
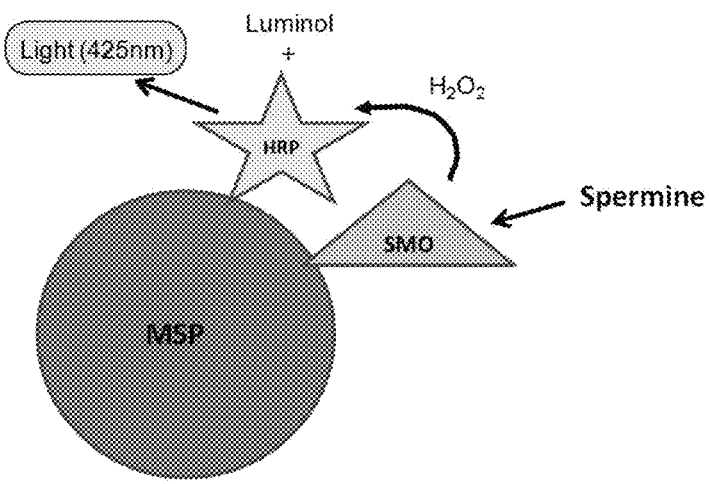
FIGS. 9A-9B show a reaction schematic for the detection of spermine and clinical value of that detection (FIG. 9A), as well as a schematic diagram of the oxidative I (oxidized) assay modality being used to detect the biomarker spermine (FIG. 9B).

FIGS. 9A-9B, 10A-10B, 11A-11B, 12A-12B, 13A-13B, 14A-14B, 15A-15B, and 16A-16B provide a schematic diagrams of the oxidative I assay detection modality. With reference to FIGS. 9A and 9B, in one embodiment, the assay detects the presence or absence of the biomarker spermine. In one embodiment, recombinant SMO and HRP are immobilized on the same support (e.g., MSP via silica-binding tags, though other substrates and means of tethering are possible). This embodiment also includes providing luminol and cofactors for the assay. If performed within a microchannel card, these additional assay components may be preloaded into such a device (e.g., a pre-loading chamber) to participate in the assay. If spermine is present, it will be oxidized by SMO, creating $H_2O_2$ which will then be utilized by HRP with luminol to produce a photon of light. The amount of photons will be proportional to the amount of $H_2O_2$ and thus correlate to the amount of spermine in the system.

With reference to FIGS. 10A-10B, in one embodiment, the assay detects the presence or absence of the biomarker UA. UA is a prognostic biomarker that correlates to the stability of the neural injury (Hozawa et al., "Serum Uric Acid and Risk of Ischemic Stroke: The ARIC Study," *Atherosclerosis* 187(2):401-7 (2006), which is hereby incorporated by reference in its entirety). In one embodiment, recombinant uricase and HRP are immobilized on the same support (e.g., MSP via silica-binding tags, though other substrates and means of tethering are possible). This embodiment also includes providing luminol and cofactors for the assay. If performed within a microchannel card, these additional assay components may be preloaded into such a device (e.g., a pre-loading chamber) to participate in the assay. If UA is present, it will be oxidized by uricase creating $H_2O_2$ which will then be utilized by HRP with luminol to produce a photon of light. The amount of photons will be proportional to the amount of $H_2O_2$ and thus correlate to the amount of UA in the system.

With reference to FIGS. 11A and 11B, in one embodiment, the assay detects the presence or absence of the biomarker glutamate. In one embodiment, recombinant LGO and HRP are immobilized on the same support (e.g., MSP via silica-binding tags, though other substrates and means of tethering are possible). This embodiment also includes providing luminol and cofactors for the assay. If performed within a microchannel card, these additional assay components may be preloaded into such a device (e.g., a pre-loading chamber) to participate in the assay. If glutamate is present, it will be oxidized by LGO, creating $H_2O_2$ which will then be utilized by HRP with luminol to produce a photon of light. The amount of photons will be proportional to the amount of $H_2O_2$ and thus correlate to the amount of glutamate in the system.

With reference to FIGS. 12A and 12B, in one embodiment, the assay detects the presence or absence of the biomarker arginine. In one embodiment, recombinant LAO and HRP are immobilized on the same support (e.g., MSP via silica-binding tags, though other substrates and means of tethering are possible). This embodiment also includes providing luminol and cofactors for the assay. If performed within a microchannel card, these additional assay components may be preloaded into such a device (e.g., a pre-loading chamber) to participate in the assay. If arginine is present, it will be oxidized by LAO, creating $H_2O_2$ which will then be utilized by HRP with luminol to produce a photon of light. The amount of photons will be proportional to the amount of $H_2O_2$ and thus correlate to the amount of arginine in the system.

With reference to FIGS. 13A and 13B, in one embodiment, the assay detects the presence or absence of the biomarker glycine. In one embodiment, recombinant GO and HRP are immobilized on the same support (e.g., MSP via silica-binding tags, though other substrates and means of tethering are possible). This embodiment also includes providing luminol and cofactors for the assay. If performed within a microchannel card, these additional assay components may be preloaded into such a device (e.g., a pre-loading chamber) to participate in the assay. If glycine is present, it will be oxidized by GO, creating $H_2O_2$ which will then be utilized by HRP with luminol to produce a photon of light. The amount of photons will be proportional to the amount of $H_2O_2$ and thus correlate to the amount of glycine in the system.

With reference to FIGS. 14A and 14B, in one embodiment, the assay detects the presence or absence of the biomarker glucose. In one embodiment, recombinant GOx and HRP are immobilized on the same support (e.g., MSP via silica-binding tags, though other substrates and means of tethering are possible). This embodiment also includes providing luminol and cofactors for the assay. If performed within a microchannel card, these additional assay components may be preloaded into such a device (e.g., a pre-loading chamber) to participate in the assay. If glucose is present, it will be oxidized by GOx, creating $H_2O_2$ which will then be utilized by HRP with luminol to produce a photon of light. The amount of photons will be proportional to the amount of $H_2O_2$ and thus correlate to the amount of glucose in the system.

With reference to FIGS. 15A and 15B, in one embodiment, the assay detects the presence or absence of the biomarker homocysteine. In one embodiment, recombinant MS and MOx and HRP are immobilized on separate supports (e.g., MSP via silica-binding tags, though other substrates and means of tethering are possible). This embodiment also includes providing luminol and cofactors for the assay. If performed within a microchannel card, these additional assay components may be preloaded into such a device (e.g., a pre-loading chamber) to participate in the assay. If homocysteine is present, it will be converted by Methionine synthase ("MS") to Methionine, which will be oxidized by MOX, creating $H_2O_2$. The $H_2O_2$ will then be utilized by HRP with luminol to produce a photon of light. The amount of photons will be proportional to the amount of $H_2O_2$ and thus correlate to the amount of homocysteine in the system.

With reference to FIGS. 16A and 16B, in one embodiment, the assay detects the presence or absence of the biomarker iron. In one embodiment, recombinant IRo (i.e., a suitable iron oxidase) and HRP are immobilized on the same support (e.g., MSP via silica-binding tags, though other substrates and means of tethering are possible). This embodiment also includes providing luminol and cofactors for the assay. If performed within a microchannel card, these additional assay components may be preloaded into such a device (e.g., a pre-loading chamber) to participate in the assay. If iron is present, it will be oxidized by IRo, creating $H_2O_2$ which will then be utilized by HRP with luminol to produce a photon of light. The amount of photons will be proportional to the amount of $H_2O_2$ and thus correlate to the amount of iron in the system.

FIGS. 17A-17D provide a schematic diagram of two embodiments of the oxidative II assay detection modality. FIGS. 17A and 17B relate to the detection of the biomarker PAO, which is also elevated in the blood after brain injury, and is presented as an example. With reference to FIGS. 17A and 17B, in this embodiment, recombinant HRP is immobilized on MSPs via a silica binding tag, though other substrates and means of tethering are possible. N1-acetyl-spermine ("N1AS") is also provided. This embodiment also includes providing luminol and cofactors for the assay. If performed within a microchannel card, these additional assay components may be preloaded into such a device (e.g., a pre-loading chamber) to participate in the assay. If PAO is present, it will oxidize N1AS, creating $H_2O_2$, which will then be utilized by HRP with luminol to produce a photon of light. The amount of photons will be proportional to the amount of $H_2O_2$ and thus correlate to the amount of PAO in the system.

With reference to FIGS. 17C and 17D, in one embodiment, the assay detects the presence or absence of the biomarker spermine oxidase ("SMO"). In one embodiment, HRP are immobilized on a support (e.g., MSP via silica-binding tags, though other substrates and means of tethering are possible). This embodiment also includes providing luminal, spermine, and cofactors for the assay. If performed within a microchannel card, these additional assay components may be preloaded into such a device (e.g., in a pre-loading chamber) to participate in the assay. If SMO is present, it will oxidize spermine, creating $H_2O_2$ which will then be utilized by HRP with luminol to produce a photon of light. The amount of photons will be proportional to the amount of $H_2O_2$ and thus correlate to the amount of SMO in the system.

In one embodiment, the assay according to the present invention includes a cleavage assay detection modality. This modality encompasses two sets of methods to detect biomarkers having the ability to cleave proteins or other substrates. "Cleavage I, release of BL enzyme" includes proteolytic or hydrolytic biomarkers (e.g., MMP1, MMP2, MMP9, APC, chitotriosidase and TPA), which would cleave a linker protein (e.g., collagen for MMP1, MMP2, and MMP9; Factor V/VIII for APC; chitin for chitotriosidase; and plasminogen for TPA) that tethers Luc to a scaffold such as a nanoparticle. It will be understood that such linker proteins or neural injury biomarker cleavage substrates may be artificial and engineered to include a cleavable domain (e.g., a cleavable domain having similarity to those of the above-identified linker proteins).

In one embodiment, engineered linker proteins (or neural injury biomarker cleavage substrates) which can be cleaved by these biomarkers will include an affinity tag at one end of the protein attaching it to a support. In one embodiment, the other end of the linker protein is fused with a BL protein (e.g., renilla luciferase). When the biomarker is present, it will cleave the linker protein, releasing the BL protein. It will be understood that any suitable detectable tag or label could be used in place of the BL protein according to this embodiment. Depending on how the reader is configured or positioned, this could then be detected as either a decrease in light emitted in the region where the linkers were originally tethered, or as an increase in signal further downstream (e.g., at a location that is spatially separated from the tethered linker) in a microfluidic system. "Cleavage II, release of BL substrate" includes biomarkers such as glutathione S-transferase ("GST") which are detected by their cleaving of an engineered substrate that then becomes active, enabling it to serve as substrate for a BL enzyme tethered to MSPs, causing photons to be released. Inactive substrate and cofactors may also be provided for the assay. If performed within a microchannel card, these additional assay components may be preloaded into such a device (e.g., a pre-loading chamber) to participate in the assay.

FIGS. 18A-18D, 19A-19B, 20A-20B, 21A-21B, 22A-22B, and 23A-23B provide a schematic diagrams of the linker protein assembly (FIGS. 18A, 18C, 19A, 20A, 21A, 22A, and 23A for MMP1, MMP2, MMP9, APC, chitotriosidase, and TPA, respectively) and the cleavage I assay detection modality (FIGS. 18B, 18D, 19B, 20B, 21B, 22B, and 23B for MMP1, MMP2, MMP9, APC, chitotriosidase, and TPA, respectively). Detection of the biomarker MMP1, MMP2, and MMP9 (FIGS. 18A-20B) are described as an example. In one embodiment, recombinant collagen is expressed with a binding tag on one end, allowing it to be attached to a nanoparticle, support, or scaffold of some type. In this embodiment, this same collagen is expressed as a fusion protein with Luc (FIGS. 18A-18B, and 19A-20B) or renilla Luc (FIGS. 18C-18D), thereby immobilizing the enzyme on a scaffold such as an MSP, though other substrates and means of tethering are possible. Coelenterazine, ATP, and cofactors are also provided for the assay involving renilla Luc and ATP, D-luciferin, and $O_2$ for the assay involving Luc. If performed within a microchannel card, these additional assay components may be preloaded into such a device (e.g., a pre-loading chamber) to participate in the assay. If MMP1, MMP2, or MMP9 is present, it will cleave and dissociate collagen causing the Luc or renilla Luc to be released (or flow downstream). The increased signal in the read out region downstream (shaded) will correlate to the amount of MMP1 MMP2, or MMP9 in the system. In a variation of this approach, the support to which the linker protein is attached can be a quantum dot. This tethering will allow for bioluminescent resonance energy transfer (BRET) between the BL protein and the quantum dot. As the linker protein is cleaved the BRET signal will diminish. The change in signal in both embodiments can quantitatively correlate to the amount of biomarker in the system.

FIGS. 24A-24B provide a schematic diagram of the cleavage II assay detection modality. Detection of the diagnostic biomarker GST is used as an example. Luciferin-NT is a commercially available form of luciferin engineered to be inactive. In one embodiment, recombinant Luc is expressed with a binding tag on one end, tethering it to a support (e.g., MSPs, though other substrates and means of tethering are possible). Luciferin-NT, ATP, glutathione (GSH) and cofactors are also provided for the assay. If performed within a microchannel card, these additional assay components may be preloaded into such a device (e.g., a pre-loading chamber) to participate in the assay. If GST is present in the sample, it will catalyze the conversion of luciferin-NT to D-luciferin which can then be used by MSP-Luc with ATP to produce light. The amount of light emitted is directly proportional to the amount of D-luciferin in the system, thereby corresponding to the amount of GST in the system.

In one embodiment the assay includes a BL cofactor assay detection modality. This approach is used to detect biomarkers (e.g., calcium, $Ca^{2+}$) that affect or enable the activity of a bioluminescent ("BL") enzyme (e.g., aequorin) by serving as a cofactor. The biomarker will allow the BL protein to interact productively with its substrate, and thereby emit light.

FIGS. 25A-25B provide a schematic diagram of the BL cofactor assay detection modality. Detection of the biomarker $Ca^{2+}$, a prognostic indicator for neural damage (i.e., one which will help a physician gauge how well the patient will recover from neural damage), is provided as an example. Aequorin ("Aeq") has three binding domains for $Ca^{2+}$, which must be filled for Aeq to catalyze its reaction with the substrate coelenterazine and emit a photon. In one embodiment, recombinant Aeq is expressed with a binding tag on one end, tethering it to a support (e.g., MSPs, though other substrates and means of tethering are possible). Coelenterazine and oxygen are provided for this assay. If performed within a microchannel card, these additional assay components may be preloaded into such a device (e.g., a pre-loading chamber) to participate in the assay. If $Ca^{2+}$ is present, it will bind to Aeq which will then emit light. The amount of photons collected will be proportional to the amount of $Ca^{2+}$ in the system.

In the above descriptions of the assay detection modalities, transduction into a common luminescent readout is contemplated. As will be understood, these assays may be varied to produce other readouts, such as colorimetric changes. For example, replacing the HRP luminescent substrate, luminol, with chromogenic substrates (e.g., TMB, DAB, ABTS) will result in a colorimetric readout that could be detected directly for the oxidation assay modality. In another example, for modalities that result in pyruvate production via PK (NSE, PGM), pyruvate oxidase (POx) could replace Luc to produce a colorimetric signal-producing reaction. Similarly, to obtain colorimetric signal production for the cleavage assay modality, Luc could be replaced with HRP. For the assay used to detect S100β, PGK and Luc could be omitted and NADH produced by GAPDH could be utilized to reduce the chromogen tetrazolium chloride, producing a color change.

One aspect of the present invention relates to a method for detecting the presence or absence of a neural injury biomarker in a biological sample. This method includes providing a biological sample and subjecting the biological sample to an assay to detect the neural injury biomarker. The assay is selected from the group consisting of: (a) an assay to detect S100β, where the assay includes (i) providing aldolase, glyceraldehyde 3-phosphate dehydrogenase ("GAPDH"), and a signal-transducing molecule, each immobilized on one or more supports, (ii) providing fructose 1,6-bisphosphate and $NAD^+$, and (iii) contacting the biological sample with the one or more supports, $NAD^+$, and fructose 1,6-bisphosphate under conditions effective to cause a cascading biological reaction leading to production of a measurable signal by the signal-transducing molecule if S100β is present in the biological sample; (b) an assay to detect S100β, where the assay includes (i) providing phosphoglyceromutase ("PGM"), enolase, pyruvate kinase, and a signal-transducing molecule, each immobilized on one or more supports, (ii) providing 3-phosphoglycerate and (iii) contacting the biological sample with the one or more supports and 3-phosphoglycerate under conditions effective to cause a cascading biological reaction leading to production of a measurable signal by the signal-transducing molecule if S100β is present in the biological sample; (c) an assay to detect glial fibrillary acidic protein ("GFAP"), where the assay includes (i) providing a GFAP-phosphorylating kinase and luciferase, each immobilized on one or more supports, (ii) providing D-luciferin, $O_2$, and ATP, and (iii) contacting the biological sample with the one or more supports, D-luciferin, $O_2$, and ATP under conditions effective to permit a sequential reaction, whereby GFAP, if present in the biological sample, will react with the GFAP-phosphorylating kinase and ATP thereby producing ADP, whereby a decreased amount of ATP reacts with D-luciferin, $O_2$, and luciferase to produce a measurable signal compared to when GFAP is not present in the biological sample and the sequential reaction does not take place; (d) an assay to detect a neural injury biomarker, wherein the neural injury biomarker is an enzyme, the assay comprising (i) providing one or more substrates of the neural injury-biomarker and one or more co-factors, (ii) providing one or more enzymes capable of acting upon the product of a reaction between the neural injury biomarker and the one or more substrates, wherein at least one enzyme is immobilized on one or more supports and at least one of the one or more enzymes is a signal-transducing molecule; and (iii) contacting the biological sample with the one or more substrates and the one or more enzymes under conditions effective to permit a sequential reaction, whereby the neural injury biomarker, if present in the biological sample, will react with the one or more substrates causing a single reaction or a series of coupled reactions that cause production of a measurable signal by the signal-transducing molecule; and (e) combinations of two or more of (a), (b), (c), and (d). The method also includes detecting, based on said subjecting, the measurable signal, where the measurable signal indicates presence or absence of the neural injury biomarker in the biological sample.

In one embodiment, the measurable signal is a photometrically detectable signal, an electrochemically detectable signal, a colorimetrically detectable signal, a fluorescent signal, an antibody, an oligomarker, or an oligonucleotide molecule. In one embodiment, the measurable signal is a photometrically detectable signal or a colorimetrically detectable signal.

In one embodiment, the nanoparticle comprises a material selected from the group consisting of a polymer, iron (II,III) oxide, gold, silver, carbon, silica, nickel, CdSe, and CdS. In one embodiment, the nanoparticle is a magnetic, silica-coated nanoparticle ("MSP").

As noted above, in one embodiment, the assay is an assay to detect S100β. where the assay includes (i) providing aldolase, glyceraldehyde 3-phosphate dehydrogenase ("GAPDH"), and a signal-transducing molecule, each immobilized on one or more supports, (ii) providing fructose 1,6-bisphosphate and NAD$^+$, and (iii) contacting the biological sample with the one or more supports, NAD$^+$, and fructose 1,6-bisphosphate under conditions effective to cause a cascading biological reaction leading to production of a measurable signal by the signal-transducing molecule if S100β is present in the biological sample. In one embodiment, the aldolase, GAPDH, and signal-transducing molecule are each immobilized on separate supports In one embodiment, the signal-transducing molecule is the chromogen tetrazolium chloride, and the cascading biological reaction comprises S100β modulating the activity of aldolase to increase the fructose 1,6-bisphosphate to glyceraldehyde 3-phosphate conversion rate, the glyceraldehyde 3-phosphate reacting with GAPDH and NAD$^+$ to produce 1,3-bisphosphoglycerate and NADH with the NADH reacting with the chromogen tetrazolium chloride to produce to produce a measurable signal.

In one embodiment, luciferase is the signal-transducing molecule. In this embodiment, the assay further includes providing phosphoglycerate kinase ("PGK"), ADP, D-luciferin, and O$_2$, where the PGK, ADP, D-luciferin, and O$_2$ are contacted with the biological sample during said contacting and the cascading biological reaction includes S100β modulating the activity of aldolase to increase the fructose 1,6-bisphosphate to glyceraldehyde 3-phosphate conversion rate, the glyceraldehyde 3-phosphate reacting with GAPDH and NAD$^+$ to produce 1, 3-bisphosphoglycerate and NADH with the 1, 3-bisphosphoglycerate and ADP reacting with PGK to produce 3-phosphoglycerate and ATP. The ATP then reacts with luciferase to produce a measurable signal.

As noted above, in one embodiment, the assay is an assay to detect S100β, where the assay includes (i) providing phosphoglyceromutase ("PGM"), enolase, pyruvate kinase, and a signal-transducing molecule, each immobilized on one or more supports, (ii) providing 3-phosphoglycerate and (iii) contacting the biological sample with the one or more supports and 3-phosphoglycerate under conditions effective to cause a cascading biological reaction leading to production of a measurable signal by the signal-transducing molecule if S100β is present in the biological sample. In one embodiment, the PGM, enolase, pyruvate kinase, and signal-transducing molecule are each immobilized on separate supports. In one embodiment the PGM, enolase, pyruvate kinase, and signal-transducing molecule are each immobilized on the same support. In another embodiment, at least two or at least three of the PGM, enolase, pyruvate kinase, and signal-transducing molecule are each immobilized on the same support.

In one embodiment, the signal-transducing molecule is luciferase. In this embodiment, the method includes providing D-luciferin and O$_2$, where the D-luciferin and O$_2$ are contacted with the biological sample during said contacting. In this embodiment, the cascading biological reaction includes S100β modulating the activity of PGM to increase the 3-phosphoglycerate to 2-phosphoglycerate conversion rate, the 2-phosphoglycerate reacting with enolase to produce phosphoenolpyruvate ("PEP") and ADP with the PEP and ADP reacting with pyruvate kinase to produce pyruvate and ATP, said ATP reacting with luciferase to produce a measurable signal.

As noted above, in one embodiment, the methods according to the present invention include an assay to detect glial fibrillary acidic protein ("GFAP"), where the assay includes (i) providing a GFAP-phosphorylating kinase and luciferase, each immobilized on one or more supports, (ii) providing D-luciferin, O$_2$, and ATP, and (iii) contacting the biological sample with the one or more supports, D-luciferin, O$_2$, and ATP under conditions effective to permit a sequential reaction, whereby GFAP, if present in the biological sample, will react with the GFAP-phosphorylating kinase and ATP thereby producing ADP, whereby a decreased amount of ATP reacts with luciferase to produce a measurable signal compared to when GFAP is not present in the biological sample and the sequential reaction does not take place In one embodiment, the GFAP-phosphorylating kinase and luciferase are each immobilized on separate supports. In one embodiment, the supports are nanoparticles. In one embodiment the GFAP-phosphorylating kinase and luciferase are each immobilized on the same support.

The GFAP-phosphorylating kinase according to the present invention may be any suitable kinase that is capable of phosphorylating GFAP. In one embodiment, the GFAP-phosphorylating kinase is selected from the group consisting of rho-associated protein kinase ("ROCK"), ROCK1, ROCK2, and Aurora-B kinase.

In one embodiment, the assay also includes providing a GFAP-dephosphorylating phosphatase and contacting the biological sample with the GFAP-dephosphorylating phosphatase prior to contacting the GFAP with the GFAP-phosphorylating kinase.

In one embodiment, a decrease in the measurable signal indicates the presence of the particular neural injury biomarker in the biological sample. In one embodiment, the biological sample is subjected to an assay to detect GFAP according to the present invention where a decrease in the measurable signal, compared to when GFAP is not present in the biological sample, indicates presence of the GFAP in the biological sample. In one embodiment, the biological sample is subjected to an assay to detect GFAP according to the present invention where a decrease in the measurable signal, compared to a positive control indicates presence of the GFAP in the biological sample.

In one embodiment according to the present invention, the assay further comprises carrying out a positive and/or negative control. In one embodiment, detecting the presence or absence of a measurable signal according to the present invention includes comparison with a positive and/or negative control. In one embodiment, the comparison with a control includes detecting an increase or decrease in a measurable signal as compared to a control.

As noted above, in one embodiment, an assay to detect a neural injury biomarker that is an enzyme is carried out. This assay includes providing one or more substrates of the neural injury-biomarker and one or more co-factors. The assay also includes providing one or more enzymes capable of acting upon the product of a reaction between the neural injury biomarker and the one or more substrates, where at least one enzyme is immobilized on one or more supports and at least one of the one or more enzymes is a signal-transducing molecule. This assay also includes contacting the biological sample with the one or more substrates and the one or more enzymes under conditions effective to permit a sequential reaction, whereby the neural injury biomarker, if present in the biological sample, will react with the one or more substrates causing a single reaction or a series of coupled reactions that cause production of a measurable signal by the signal-transducing molecule.

The enzyme detected according to this assay may include any suitable neural injury biomarker that is an enzyme. In one embodiment, the neural injury biomarker that is an enzyme is selected from the group consisting of neuron specific enolase ("NSE"), phosphoglyceromutase ("PGM"), and nucleoside diphosphate kinase A ("NDK-A").

In one embodiment, the neural injury biomarker that is an enzyme is NSE, the signal-transducing molecule is luciferase, the one or more enzyme substrates includes 2-phosphoglycerate and the one or more enzymes includes pyruvate kinase. In this embodiment, at least pyruvate kinase is immobilized on a first support. This assay also includes providing D-luciferin and $O_2$, where the D-luciferin and $O_2$ are contacted with the biological sample during the contacting step under conditions effective to permit a sequential reaction, where the NSE, if present in the biological sample, will react with the 2-phosphoglycerate to produce PEP and ADP, with the PEP and ADP reacting with pyruvate kinase to produce pyruvate and ATP. The ATP will then react with luciferase to produce a measurable signal In another embodiment, the neural injury biomarker that is an enzyme is PGM. In this embodiment, the signal-transducing molecule is luciferase, the one or more substrates include 3-phosphoglycerate, the one or more enzymes include enolase and pyruvate kinase, and at least pyruvate kinase is immobilized on a first support. This assay also includes providing D-luciferin and $O_2$, where the D-luciferin and $O_2$ are also contacted with the biological sample under conditions effective to permit a sequential reaction, whereby the PGM, if present in the biological sample, will react with the 3-phosphoglycerate to produce 2-phosphoglycerate, the 2-phosphoglycerate reacting with enolase to produce PEP and ADP, with the PEP and ADP reacting with pyruvate kinase to produce pyruvate and ATP. The ATP will then react with luciferase to produce a measurable signal.

In another embodiment, the neural injury biomarker that is an enzyme is NDK-A, the signal-transducing molecule is luciferase, the one or more substrates comprise GTP and ADP, and at least luciferase is immobilized on the first support. The method also includes providing D-luciferin and $O_2$, where the D-luciferin and $O_2$ are contacted with the biological sample during the contacting step under conditions effective to permit a sequential reaction, whereby the NDK-A, if present in the biological sample, will react with the GTP and ADP to produce GDP and ATP, said ATP reacting with luciferase to produce a measurable signal.

As noted above, in one embodiment the presence of the measurable signal indicates the presence of the neural injury biomarker. In one embodiment, a biological sample is subjected to an assay to detect the presence or absence of S100β or a neural injury marker that is an enzyme, where the presence of the measurable signal indicates the presence of the neural injury biomarker.

In other embodiments, the absence of or decrease in a measurable signal indicates the presence of a particular neural injury biomarker. In one embodiment the biological sample is subjected to the assay to detect the presence or absence of GFAP, where a reduction in the measurable signal, compared to when GFAP is not present in the biological sample, indicates presence of the GFAP in the biological sample. In one embodiment, the reduction is measured by comparison to a control or standard value.

In one embodiment, the neural injury biomarker is detected and the detecting includes quantifying the amount of neural injury biomarker present in the biological sample.

In one embodiment, the support(s) comprise(s) a nanoparticle. In certain embodiments, the nanoparticle comprises a material selected from the group consisting of a polymer, iron (II,III) oxide, gold, silver, carbon, silica, nickel, CdSe, and CdS.

In one embodiment, the method includes providing a platform or surface comprising one or more channels and subjecting the biological sample to the assay within the one or more channels. In one embodiment, the channel is a microfluidic channel.

In one embodiment, a combination of two or more of the assays according to the present invention are carried out, each assay being carried out in a separate channel of the one or more channels. As noted above, any combination of assays may be carried out according to the present invention.

One embodiment of the present invention involves subjecting the biological sample to at least one assay of (a), (b), (c), and (d) and at least a second assay different than the assays of (a), (b), (c), and (d) to detect a neural injury biomarker. In this embodiment, the second assay produces a measurable signal if the neural injury biomarker is present in the sample. This embodiment also includes detecting, based on said subjecting the biological sample to the at least a second assay, the measurable signal produced by the second assay, wherein the measurable signal produced by the second assay indicates presence or absence of the neural injury biomarker in the biological sample. The measurable signals produced by the assays of (a), (b), (c), and (d) may be the same or different than that of the second assay.

The second assay may be any assay suitable to detect a neural injury biomarker. In one embodiment, the second assay is any assay according to the present invention. In one embodiment, the second assay is selected from the group consisting of an assay that comprises an oxidation reaction, a cleavage reaction, and a reaction where the biomarker is a cofactor. Suitable assays involving an oxidation reaction, a cleavage reaction, or a reaction where the biomarker is a cofactor are described supra as part of an oxidative assay detection modality, a cleavage assay detection modality, or a BL cofactor assay detection modality, respectively. In one embodiment according to the present invention, the sample is subjected to more than one assay to detect at least two neural injury biomarkers, at least three neural injury biomarkers, at least four neural injury biomarkers, at least five neural injury biomarkers, at least six neural injury biomarkers, at least seven neural injury biomarkers, at least eight neural injury biomarkers, at least nine neural injury biomarkers, or at least ten neural injury biomarkers.

In one embodiment, the second assay includes an oxidation reaction. In one embodiment, this assay involves (i) providing one or more reactants, (ii) providing a signal-transducing molecule, (iii) contacting the biological sample with the one or more reactants under conditions effective to permit a sequential reaction involving the one or more reactants and the neural injury biomarker, if present in the biological sample, to cause the signal-transducing molecule to produce a measurable signal.

In one embodiment, the second assay involves an oxidation reaction and detects a neural injury biomarker selected from the group consisting of spermine, uric acid, glutamate, arginine, glycine, glucose, homocysteine, iron, spermine oxidase ("SMO"), and PAO.

In one embodiment, the second assay includes a cleavage reaction. In one embodiment, the assay involves (i) providing a neural injury biomarker cleavage substrate immobilized on a support, (ii) providing label bound to the neural injury biomarker cleavage substrate, wherein the label produces the measurable signal, and (iii) contacting the biological sample with the support under conditions effective to permit the neural injury biomarker, if present in the biological sample, to cleave neural injury biomarker cleavage substrate thereby releasing the measurable signal. In one embodiment, the contacting and the detecting occur at spatially separated locations. In another embodiment, the contacting and the detecting occur at the same location.

In one embodiment, the second assay involves a cleavage reaction and detects a neural injury biomarker selected from the group consisting of MMP1, MMP2, MMP9, APC, chitotriosidase, and TPA.

In one embodiment, the second assay involves a cleavage reaction. In this embodiment the assay involves (i) providing a neural injury biomarker cleavage substrate bound to a substrate for a signal transducing molecule, (ii) providing the signal-transducing molecule, and (iii) contacting the biological sample with the neural injury biomarker cleavage substrate under conditions effective to permit the neural injury biomarker, if present in the biological sample, to cleave neural injury biomarker cleavage substrate thereby releasing the substrate for a signal transducing molecule, the substrate for a signal transducing molecule reacting with the signal-transducing molecule to produce a measurable signal.

In one embodiment, the second assay involves a cleavage reaction and the second assay detects glutathione s-transferase.

In one embodiment, the second assay detects the neural injury biomarker $Ca^{2+}$. In this embodiment, the second assay involves (i) providing aequorin immobilized on a support and (ii) contacting the biological sample with the support under conditions effective to permit the $Ca^{2+}$, if present in the biological sample, to react with aequorin to produce the measurable signal.

In one embodiment, a platform comprising one or more channels is provided and the biological sample is subjected to the assay of (a), (b), (c), and/or (d) and the at least a second assay, each assay being carried out within a separate channel of the one or more channels.

Another aspect of the present invention relates to a method of determining a subject's neural injury state. This method involves carrying out a method for detecting the presence or absence of a neural injury biomarker in a biological sample according to the present invention where the biological sample is provided from a subject. The method also involves determining, based on the detecting, the neural injury state of the subject. Determining the neural injury state of a subject may involve detection of neural injury in a subject, diagnosing the subject as having a particular neural injury, or determining the prognosis of a particular neural injury.

In one embodiment, detecting a measurable signal according to the present invention includes quantifying the amount of the neural injury biomarker present in the biological sample. In one embodiment, the evaluation of or determining a subject's neural injury state includes diagnosing the subject as having a neural injury resulting from ischemic stroke, hemorrhagic stroke, trauma leading to concussion, trauma leading to contusion, or aneurism.

In one embodiment, determining a subject's neural injury state or status involves identifying the presence or nature of a pathologic condition (e.g., stroke). In one embodiment, determining a subject's neural injury state includes diagnosing the subject as having a neural injury. In one embodiment, determining involves detecting a diagnostic amount of a particular neural injury biomarker. A diagnostic amount refers to an amount of a marker in a subject's sample that is consistent with a diagnosis of neural injury (e.g., stroke). A diagnostic amount can be either in absolute amount (e.g., μg/ml) or a relative amount (e.g., relative intensity of signals in a biological sample versus a positive or negative control or control amount). A diagnostic amount may be an amount that is greater than or less than a relative or control amount. The relationship between the amount of a particular neural injury biomarker in a sample and its relevance to diagnosis (or prognosis) of a particular neural injury will be understood based on the biomarker's clinical relevance (see, e.g., Whiteley et al., "Blood Biomarkers in the Diagnosis of Ischemic Stroke: A Systematic Review," *Stroke* 39(10): 2902-9 (2008); Saenger and Christenson, "Stroke Biomarkers: Progress and Challenges for Diagnosis, Prognosis, Differentiation, and Treatment," *Clin. Chem.* 56(1):21-33 (2010); Whiteley et al., "Blood Markers for the Prognosis of Ischemic Stroke: A Systematic Review," *Stroke* 40(5): e380-9 (2009); Hayashi et al., "A New Stroke Marker as Detected by Serum Phosphoglycerate Mutase B-type Isozyme," *Biochem. Biophy. Res. Comm.* 287: 843-845 (2001); Casmiro et al., "Cerebrospinal Fluid and Serum Neuron-Specific Enolase Concentrations in a Normal Population," *European J. Neurol.* 12(5):369-74 (2005); Allard et al., "PARK7 and Nucleoside Diphosphate Kinase A as Plasma Markers for The Early Diagnosis of Stroke," *Clin. Chem.* 51(11):2043-51 (2005); Hasan et al., "Towards the Identification of Blood Biomarkers for Acute Stroke in Humans: A Comprehensive Systematic Review," *British J. Clin. Pharm.* doi: 10.1111/j.1365-2125.2012.04212.x. (2012); Tomotori et al., "Polyamine Oxidase and Acrolein as Novel Biochemical Markers for Diagnosis of Cerebral Stroke" *Stroke* 36:2609-2613 (2005); Castellanos et al., "Plasma Metalloproteinase-9 Concentration Predicts Hemorrhagic Transformation in Acute Ischemic Stroke," *Stroke* January; 34(1):40-6 (2003); Artieda et al., "Serum Chitotriosidase Activity, A Marker of Activated Macrophages, Predicts New Cardiovascular Events Independently of C-Reactive Protein," *Cardiology* 108(4):297-306 (2007), which are hereby incorporated by reference in their entirety).

In one embodiment, determining a subject's neural injury status includes diagnosing the subject as having a neural injury resulting from stroke. In another embodiment the determining includes diagnosing the subject as having a neural injury resulting from ischemic stroke, hemorrhagic stroke, trauma leading to concussion, trauma leading to contusion, or aneurism. In yet another embodiment, determining a subject's neural injury status includes distinguishing between a neural injury resulting from stroke and a stroke mimic (e.g., diseases impairing neural function, electrolyte imbalance, migraine and/or neoplasia).

In one embodiment according to the present invention, diagnosing the subject as having a neural injury resulting from stroke includes subjecting a sample to more than one assay according to the present invention. In one embodiment, at least two neural injury biomarkers, at least three neural injury biomarkers, at least four neural injury biomarkers, at least five neural injury biomarkers, at least six neural injury biomarkers, at least seven neural injury biomarkers, at least eight neural injury biomarkers, at least nine neural injury biomarkers, or at least ten neural injury biomarkers are detected in a diagnostic and/or prognostic amount.

In one embodiment, the methods according to the present invention detect a neural injury biomarker selected from the group consisting of S100β, GFAP, NSE, PGM, NDK-A, and combinations thereof. In one embodiment, a diagnostic amount of a neural injury biomarker selected from the group consisting of S100β, GFAP, NSE, PGM, NDK-A, and combinations thereof is detected.

In one embodiment, the methods according to the present invention detect a neural injury biomarker selected from the group consisting of S100β, GFAP, NSE, PGM, NDK-A, spermine, spermine oxidase, homocysteine, PAO, MMP-1, MMP-2, MMP-9, chitotriosidase, TPA, GST, and combinations thereof. In one embodiment, a diagnostic amount of a neural injury biomarker selected from the group consisting of S100β, GFAP, NSE, PGM, NDK-A, spermine, spermine oxidase, arginine, homocysteine, PAO, MMP-1, MMP-2, MMP-9, chitotriosidase, TPA, GST, and combinations thereof is detected.

In one embodiment, the diagnostic amount of S100β detected in a biological sample is an amount in the range of 0.02 to 0.1 ng/ml. In another embodiment, the amount is from about 0.02 to about 0.1 ng/ml. In one embodiment, detection of a diagnostic amount of S100β is suitable to diagnose stroke. In one embodiment, detection of a diagnostic amount of S100β is suitable to determine infarct volume, stroke severity, and/or hemorrhagic transformation. In one embodiment, a diagnostic amount of S100β is detected and determining a subject's neural injury state includes diagnosing the subject as having a neural injury resulting from stroke.

In one embodiment, the diagnostic amount of GFAP detected in a biological sample is an amount in the range of greater than µg/ml. In one embodiment, detection of a diagnostic amount of GFAP is suitable to diagnose hemorrhagic stroke. In one embodiment, a diagnostic amount of GFAP in accordance with the present invention is detected and determining a subject's neural injury state includes diagnosing the subject as having a neural injury resulting from hemorrhagic stroke.

In one embodiment, GFAP is not detected in a subject and the determining comprises diagnosing the subject as having neural injury resulting from ischemic stroke. In this embodiment, the subject may have been diagnosed as having a neural injury resulting from stroke and an assay to detect GFAP is carried out in accordance with the present invent to determine whether the subject has suffered from ischemic stroke or hemorrhagic stroke.

In one embodiment, determining the subject's neural injury state includes diagnosing the subject as having neural injury resulting from ischemic stroke and the method further includes administering to the subject tissue plasminogen activator.

In one embodiment, the diagnostic amount of NSE detected in a biological sample is an amount greater than about 8.7±3.9 ng/ml. In one embodiment, the diagnostic amount of NSE detected in a biological sample is greater than about 10 ng/ml. In one embodiment, detection of a diagnostic amount of NSE is suitable to diagnose stroke. In one embodiment, detection of a diagnostic amount of NSE is suitable to determine infarct volume and/or stroke severity. In one embodiment, a diagnostic amount of NSE in accordance with the present invention is detected and determining a subject's neural injury state includes diagnosing the subject as having a neural injury resulting from stroke.

In one embodiment, the diagnostic amount of PGM detected in a biological sample is an amount in greater than about 40 U/ml. In one embodiment, detection of a diagnostic amount of PGM is suitable to diagnose stroke. In one embodiment, a diagnostic amount of PGM in accordance with the present invention is detected and determining a subject's neural injury state includes diagnosing the subject as having a neural injury resulting from stroke.

In one embodiment, the diagnostic amount of NDK-A detected in a biological sample is an amount greater than about 2 µg/ml. In one embodiment, detection of a diagnostic amount of NDK-A is suitable to diagnose stroke. In one embodiment, a diagnostic amount of NDK-A in accordance with the present invention is detected and determining a subject's neural injury state includes diagnosing the subject as having a neural injury resulting from stroke.

In one embodiment, the diagnostic amount of spermine detected in a biological sample is an amount less than about 30 nM concentration. In one embodiment, detection of a diagnostic amount of spermine is suitable to diagnose stroke. In one embodiment, a diagnostic amount of spermine in accordance with the present invention is detected and determining a subject's neural injury state includes diagnosing the subject as having a neural injury resulting from stroke. Without being bound by theory, decrease in spermine in the case of stroke and according to this embodiment is thought to result from the conversion of spermine into acrolein.

In one embodiment, the diagnostic amount of arginine detected in a biological sample is an amount in the range of less than about 70 µM concentration. In one embodiment, detection of a diagnostic amount of arginine is suitable to diagnose stroke. In one embodiment, detection of a diagnostic amount of arginine is suitable to determine infarct volume. Arginine level has a negative correlation with infarct volume. In one embodiment, a diagnostic amount of arginine in accordance with the present invention is detected and determining a subject's neural injury state includes diagnosing the subject as having a neural injury resulting from stroke.

In one embodiment, the diagnostic amount of homocysteine detected in a biological sample is an amount in the range of greater than the concentration in a normal sample. Homocysteine is significantly increased following ischemic stroke, with a diagnostic amount detected in the range of mM (Hasan et al., "Towards the Identification of Blood Biomarkers for Acute Stroke in Humans: A Comprehensive Systematic Review," *British J. Clin. Pharm*. doi: 10.1111/j.1365-2125.2012.04212.x. (2012), which is hereby incorporated by reference in its entirety). In one embodiment, detection of a diagnostic amount of homocysteine is suitable to diagnose stroke. In one embodiment, a diagnostic amount of homocysteine in accordance with the present invention is detected and determining a subject's neural injury state includes diagnosing the subject as having a neural injury resulting from stroke.

In one embodiment, the diagnostic amount of PAO detected in a biological sample is an amount greater than about 4 nM. In one embodiment, a diagnostic amount of PAO detected in a biological sample is at least about 8.5 µM. In one embodiment, detection of a diagnostic amount of PAO is suitable to diagnose stroke. In one embodiment, detection of a diagnostic amount of PAO is suitable to determine stroke severity. In one embodiment, a diagnostic amount of PAO in accordance with the present invention is detected and determining a subject's neural injury state includes diagnosing the subject as having a neural injury resulting from stroke.

In one embodiment, a diagnostic amount of spermine oxidase is detected in a biological sample. In one embodiment, detection of a diagnostic amount of spermine oxidase is suitable to diagnose stroke. In one embodiment, a diagnostic amount of spermine oxidase in accordance with the present invention is detected and determining a subject's neural injury state includes diagnosing the subject as having a neural injury resulting from stroke. In one embodiment, both spermine and spermine oxidase are detected and a spermine oxidase/spermine ratio is calculated, and determining a subject's neural injury state includes diagnosing the subject as having a neural injury resulting from stroke based on the spermine oxidase/spermine ratio.

In one embodiment, the diagnostic amount of MMP1, MMP2, and/or MMP9 detected in a biological sample is an amount greater than 140 ng/ml. In one embodiment, detection of a diagnostic amount of MMP1, MMP2, and/or MMP9 is suitable to diagnose stroke. In one embodiment, detection of a diagnostic amount of MMP1, MMP2, and/or MMP9 is suitable to determine infarct volume, stroke severity, and hemorrhagic transformation. In one embodiment, a diagnostic amount of MMP1, MMP2, and/or MMP9 in accordance with the present invention is detected and determining a subject's neural injury state includes diagnosing the subject as having a neural injury resulting from stroke.

In one embodiment, the diagnostic amount of chitotriosidase detected in a biological sample is an amount greater than about 74.2+/−5.69 nmol/ml. In one embodiment, the diagnostic amount is at least about 116+/−30.9 nmol/ml. In one embodiment, detection of a diagnostic amount of chitriosidase is suitable to diagnose stroke. In one embodiment, detection of a diagnostic amount of chitriosidase is suitable to determine stroke severity. In one embodiment, a diagnostic amount of chitriosidase in accordance with the present invention is detected and determining a subject's neural injury state includes diagnosing the subject as having a neural injury resulting from stroke.

In one embodiment, a diagnostic amount of TPA is detected in a biological sample. In one embodiment, detection of a diagnostic amount of TPA is suitable to diagnose stroke. In one embodiment, a diagnostic amount of TPA in accordance with the present invention is detected and determining a subject's neural injury state includes diagnosing the subject as having a neural injury resulting from stroke.

In one embodiment, the diagnostic amount of GST detected in a biological sample is an amount in the range of greater than 18 ng/ml. In one embodiment, detection of a diagnostic amount of GST is suitable to diagnose stroke. In one embodiment, a diagnostic amount of GST in accordance with the present invention is detected and determining a subject's neural injury state includes diagnosing the subject as having a neural injury resulting from stroke.

In one embodiment, detection of a diagnostic or prognostic amount of a neural injury biomarker is carried out by comparison with a control amount. A control amount of a neural injury biomarker can be any amount or a range of amount which is to be compared against a test amount of a neural injury biomarker. For example, a control amount of a neural injury biomarker can be the amount of a neural injury biomarker in a person without neural injury. A control amount may be the amount of a neural injury biomarker in a positive or negative control sample carried out as part of the assay according to the present invention. A control amount can be either an absolute amount (e.g., µg/ml) or a relative amount (e.g., relative intensity of signals).

In one embodiment determining a subject's neural injury status involves identifying a patient's prognosis with respect to a particular neural injury (e.g., stroke).

In certain embodiments according to the present invention, a correlation is carried out between the detection of a neural injury biomarker in a subject's biological sample and the neural injury state of the subject. The correlation step includes correlating the assay result(s) to one or more of diagnosis, risk stratification, staging, prognosis, classifying, and monitoring of the neural injury.

The correlation between neural injury state and the detection of a neural injury biomarker is determined according to the neural injury biomarker's clinical relevance to neural injury (e.g., Whiteley et al., "Blood Biomarkers in the Diagnosis of Ischemic Stroke: A Systematic Review," *Stroke* 39(10):2902-9 (2008); Saenger and Christenson, "Stroke Biomarkers: Progress and Challenges for Diagnosis, Prognosis, Differentiation, and Treatment," *Clin. Chem.* 56(1): 21-33 (2010); Whiteley et al., "Blood Markers for the Prognosis of Ischemic Stroke: A Systematic Review," *Stroke* 40(5):e380-9 (2009); Hayashi et al., "A New Stroke Marker as Detected by Serum Phosphoglycerate Mutase B-type Isozyme," *Biochem. Biophy. Res. Comm.* 287: 843-845 (2001); Casmiro et al., "Cerebrospinal Fluid and Serum Neuron-Specific Enolase Concentrations in a Normal Population," *European J. Neurol.* 12(5):369-74 (2005); Allard et al., "PARK7 and Nucleoside Diphosphate Kinase A as Plasma Markers for The Early Diagnosis of Stroke," *Clin. Chem.* 51(11):2043-51 (2005); Hasan et al., "Towards the Identification of Blood Biomarkers for Acute Stroke in Humans: A Comprehensive Systematic Review," *British J. Clin. Pharm.* doi: 10.1111/j.1365-2125.2012.04212.x. (2012); Tomotori et al., "Polyamine Oxidase and Acrolein as Novel Biochemical Markers for Diagnosis of Cerebral Stroke" *Stroke* 36:2609-2613 (2005); Castellanos et al., "Plasma Metalloproteinase-9 Concentration Predicts Hemorrhagic Transformation in Acute Ischemic Stroke," *Stroke* January; 34(1):40-6 (2003); Artieda et al., "Serum Chitotriosidase Activity, A Marker of Activated Macrophages, Predicts New Cardiovascular Events Independently of C-Reactive Protein," *Cardiology* 108(4):297-306 (2007), which are hereby incorporated by reference in their entirety). Such relevance includes that described above with respect to the neural injury biomarkers and will be understood by those of ordinary skill in the art.

The method according to the present invention also includes determination of treatment regimens or treatments based on the determined neural injury status.

The method of determining a subject's neural injury state according to the present invention may also include selecting a subject having a neural injury and providing a biological sample from the selected subject.

In one embodiment according to the present invention, a prognostic amount of a biomarker is detected. A prognostic indicator for neural damage is one which will help a physician gauge how well the patient will recover from neural damage. A prognostic amount refers to an amount of a marker in a subject's sample that is consistent with a prognosis with respect to a neural injury (e.g., stroke). A prognostic amount can be either in absolute amount (e.g., μg/ml) or a relative amount (e.g., relative intensity of signals in a biological sample versus a positive or negative control or control amount). A prognostic amount may be an amount that is greater than or less than a relative or control amount. The relationship between the amount of a particular neural injury biomarker in a sample and its relevance to prognosis with respect to a particular neural injury will be understood based on the biomarker's clinical relevance, as noted above. In one embodiment according to the present invention, a method of determining a subject's neural injury state detects a prognostic amount of a neural injury biomarker selected from the group consisting of uric acid, glutamate, glycine, glucose, iron, APC, TPA, calcium, and combinations thereof.

In one embodiment, a prognostic amount of uric acid is detected. In one embodiment, detection of a prognostic amount of uric acid is suitable to provide a prognosis for disease recovery. In one embodiment, detection of a prognostic amount of uric acid is suitable to differentiate between a progressive and stable stroke state.

In one embodiment, the prognostic amount of glutamate detected in a biological sample is in the range of greater than about 200 μM. In one embodiment, detection of a prognostic amount of glutamate is suitable to provide a prognosis for disease recovery. In one embodiment, detection of a prognostic amount of glutamate is suitable to differentiate between a progressive and stable stroke state.

In one embodiment, the prognostic amount of glycine detected in a biological sample is in the range of greater than about 100 μM. In one embodiment, detection of a prognostic amount of glycine is suitable to provide a prognosis for disease recovery. In one embodiment, detection of a prognostic amount of glycine is suitable to differentiate between a progressive and stable stroke state.

In one embodiment, a prognostic amount of glucose is detected in a biological sample. In one embodiment, detection of a prognostic amount of glucose is suitable to provide a prognosis for disease recovery. In one embodiment, detection of a prognostic amount of glucose is suitable to differentiate between a progressive and stable stroke state.

In one embodiment, a prognostic amount of iron is detected in a biological sample. In one embodiment, detection of a prognostic amount of iron is suitable to provide a prognosis for disease recovery.

In one embodiment, a prognostic amount of APC is detected in a biological sample. In one embodiment, detection of a prognostic amount of APC is suitable to provide a prognosis for disease recovery.

In one embodiment, a prognostic amount of TPA is detected in a biological sample. In one embodiment, detection of a prognostic amount of TPA is suitable to provide a prognosis for disease recovery.

In one embodiment, the prognostic amount of calcium detected in a biological sample is an amount in the range of greater than 5 mg/dl. In one embodiment, detection of a prognostic amount of calcium is suitable to provide a prognosis for disease recovery.

In one embodiment according to the present invention, the method of determining a subject's neural injury state involves determining the subject's prognosis with regard to the neural injury. In one embodiment, the selected subject displays symptoms of a condition mediated by neural injury. In another embodiment, the selected subject has experienced a traumatic injury.

Another aspect of the present invention is directed to a system. This system includes a platform including one or more channels. At least one channel of the one or more channels includes (a) biological assay components suitable to detect the presence of S100β in a biological sample, said components including: (i) aldolase, GAPDH, and a signal-transducing molecule, each immobilized within the at least one channel and (ii) fructose 1,6-bisphosphate and $NAD^+$, said components positioned in the channel to permit a cascading biological reaction leading to production of a measurable signal by the signal-transducing molecule if S100β is present in the biological sample; (b) biological assay components suitable to detect the presence of S100β in a biological sample, said components including: (i) phosphoglyceromutase ("PGM"), enolase, pyruvate kinase, and a signal-transducing molecule, each immobilized within the at least one channel and (ii) 3-phosphoglycerate, said components positioned in the channel to permit a cascading biological reaction leading to production of a measurable signal by the signal-transducing molecule if S100β is present in the biological sample; (c) biological assay components suitable to detect the presence of GFAP in a biological sample, the components including: (i) a GFAP-phosphorylating kinase and luciferase, each immobilized within the at least one channel, (ii) D-luciferin, $O_2$, and ATP, said components positioned in the at least one channel to permit a sequential reaction in the presence of GFAP, whereby GFAP will react with the GFAP-phosphorylating kinase and ATP to produce ADP; (d) biological assay components suitable to detect the presence of a neural injury biomarker in a biological sample, wherein the neural injury biomarker is an enzyme, said components including: (i) one or more substrates of the neural injury biomarker and one or more co-factors; (ii) one or more enzymes capable of acting upon the product of a reaction between the neural injury biomarker and the one or more substrates, wherein at least one enzyme is immobilized within the at least one channel on one or more supports and at least one enzyme is a signal-transducing molecule, said components positioned in the channel to permit a sequential reaction, whereby the neural injury biomarker, if present in the biological sample, will react with the one or more substrates causing a single reaction or a series of coupled reactions that cause production of a measurable signal by the signal-transducing molecule; or (e) combinations of two or more of (a), (b), (c), and (d).

In one embodiment, the system according to the present invention includes at least one of the one or more channels that serves as a negative control. In one embodiment, at least one of the one or more channels serves as a positive control.

The system according to the present invention may also include a measurable signal detector. Suitable detectors will depend on the type of measurable signal produced and will be readily apparent to those of skill in the art. For example, in one embodiment, the detector is a photodetector (e.g., CCD, CMOS). In one embodiment, the detecting includes quantifying the amount of a biomarker in the system. As will be appreciated, quantifying may be achieved using methods that are known in the art for quantifying measurable signal according to the present invention.

In one embodiment, one or more of the biological assay components is immobilized within the one or more channels. In one embodiment, at least one channel of the one or more channels comprises the biological assay components of (a), where the aldolase, glyceraldehyde 3-phosphate dehydrogenase ("GAPDH"), and signal-transducing molecule are each immobilized on one or more nanoparticles within the at least one channel; the biological assay components of (b), where the PGM, enolase, pyruvate kinase, and signal-transducing molecule are each immobilized on one or more nanoparticles within the at least one channel; the biological assay of (c), wherein the GFAP-phosphorylating kinase and luciferase are each immobilized on one or more nanoparticles within the at least one channel; and/or the biological assay components of (d), wherein the one or more supports comprises a nanoparticle.

Immobilizing (e.g., tethering) one or more proteins involved in the reaction cascades to a scaffold, support, or platform can provide several advantages. First, it can confine either the detection reaction or the readout signal to a certain area (e.g., a certain area of a diagnostic card). This allows in-line background luminescence control readings and also reduces the size of a detector means (e.g., photodetector), if used. In addition, immobilizing enzymes has been shown to provide enhancement of enzyme stability (Liang et al., "Biomedical Application of Immobilized Enzymes," *J. Pharm. Sci.* 89(8):979-90 (2000), which is hereby incorporated by reference in its entirety), which may improve reaction kinetics (see Mukai et al., "Sequential Reactions of Surface-Tethered Glycolytic Enzymes," *Chem. Biol.* 16(9): 1013-20 (2009) and Blum et al., "Collagen Strip with Immobilized Luciferase for ATP Bioluminescent Determination," *Biotechnol. Bioeng.* 27(3):232-7 (1985), which are hereby incorporated by reference in their entirety).

The system according to the present invention may include components for carrying out the assays of the present invention as described herein. Suitable components of such assays are described supra.

In various related aspects, the present invention also relates to devices and kits for performing the methods described herein. Suitable kits comprise reagents sufficient for performing an assay for at least one of the described neural injury markers, together with instructions for performing the described determining of neural injury state.

In certain embodiments, reagents for performing such assays are provided in an assay device, and such assay devices may be included in such a kit.

FIG. 26 illustrates a possible five-biomarker detection device 2 using a colorimetric readout. As shown, the device includes inlet 4 for sample intake or loading, as well as outlet 6. In this embodiment, each of channels 8 (e.g., reaction chambers) hold enzymes required to detect a biomarker of interest according to the assays of the present invention. If the biomarker is present in the biological sample (e.g., plasma), then the color of that reaction chamber would change from, for example, yellow (shown lighter) to purple (shown darker). Note that the readout embodiment (e.g., type of color change or measureable signal), as well as the size and geometry of channels 8 may be selected or designed such that there is either no need for any detection equipment (e.g., visual determination of color change), or there could be a detecting means (e.g., photoreader or other type of detecting means) for quantitative data collection and interpretation.

Channels 8 may also include reaction chambers within the channels where one or more or all of the enzymes necessary to carry out the assay according to the present invention are immobilized. The enzymes may be immobilized on, for example, a nanoparticle or the luminal wall of the channel itself. If immobilized on nanoparticles the nanoparticles may be retained within the channel or portions of the channel (e.g., the reaction chamber) by size and shape of the nanoparticle and or the channel. In one embodiment, the nanoparticles are magnetic nanoparticles and the device further includes a magnet placed within the system (e.g., under one or more channels or portions of the channel(s)) to immobilize the magnetic nanoparticles.

Devices that incorporate systems to carry out the detection modalities according to the present invention may be provided with a single such system or may be provided with more than one such system integrated into a platform or structure (e.g., a single card or chip, such as a microfluidic chip with multiple microfluidic channels). In one embodiment, detection of each biomarker would include at least three microfluidic channels (microchannels), including a positive control channel, negative control channel, and a test channel. More channels could be used for each biomarker, with these containing varying concentrations of preloaded cofactors, substrates, or tethered enzymes for the purpose of providing improved sensitivity for biomarkers that might be present over a very wide range of concentrations. Use of microchannels would confer multiple advantages, such as facilitating rapid diagnosis, using small volumes, integrating detection of multiple biomarkers into one device (i.e., multiplexing), and providing spatial control of where readouts would occur. This latter point could minimize size and cost of the photo-detector apparatus in the reader and would also minimize channel-channel light interference.

FIG. 27A shows a device according to the present invention. A three-microchannel design device useful in the implementation of the enzymatic detection modalities according to the present invention is shown. In this embodiment, the device is shown in use with an assay to detect NSE biomarker. In this embodiment of the three-channel design device 10, substrates and cofactors for all assay reactions are preloaded into each preloading chamber 12, with exogenous NSE added to the positive control channel 14 (and not the negative control channel 16 or test channel 18). In the negative control channel 16, a key substrate or enzyme in the coupled reaction pathway would be absent. For the example of NSE detection, this negative control channel might be devoid of 2-phosphoglycerate ("2PG"), the substrate for NSE, so the reaction cannot commence. As shown, in addition to a preloading chamber, each channel may include reaction chamber 20. Nanoparticles 22 bound to a particular assay component (e.g., NP–PK and NP–Luc) may be retained within the reaction chamber via magnet 24, or other affixation method (e.g., avidin-biotin, antibodies, grids). A small volume of sample (e.g., blood) would be placed in inlet 26, and an integral separator could allow plasma to flow through the channels but prevent the cells from entering them. Alternatively, the patient's serum or plasma could be injected after having been separated from the cellular components. Plasma may drawn through channels 14, 16, 18 by capillary action, advanced through the channels 14, 16, 18 under positive pressure generated by a pump means, or by negative pressure generated by a vacuum means. Such means could be applied to outlet 28 or to another port. In this embodiment, NSE in the plasma sample is detected via the coupled reaction between NSE, PK and Luc (as shown in the test channel schematic view of FIG. 27A). Any NSE in the patient's plasma or serum would convert 2-PG into phosphoenolpyruvate ("PEP"). In the presence of additional ADP, pyruvate kinase ("PK") tethered to a nanoparticle ("NP–PK") would generate ATP. In the depicted example, luciferin would also be loaded in the preloading chamber so that in the presence of ATP and luciferin, luciferase enzyme ("Luc") tethered to nanoparticle ("NP–Luc") would emit light detectable by a reader.

As noted above, the system according to the present invention can be operative to separate a sample into a serum or plasma fraction using techniques known in the art, including but not limited to reagents (e.g., dotting factors), gel, a separation filter, a blood separation filter, a lateral flow device or centrifugal force. For example, optional filter may be included and, for example, can be a blood separation filter operative to remove particulates (e.g., red blood cells) before the sample reaches the assay components. The system according to the present invention can also be operative to immobilize the assay components using any number of techniques (e.g., magnet and magnetic supports (e.g., magnetic particles), as described above).

In one embodiment, the device (e.g., multichannel card) would include the tethered enzymes, cofactors, and substrates for use with each assay modality preloaded into the channels in, for example, a pre-loading chamber. For example, in one embodiment, enzymes tethered to magnetic NPs, substrates, and cofactors are lyophilized to enhance shelf life, and reconstituted by sample plasma as it enters the microchannels and the pre-loading chamber. An additional three dimensional figure of one embodiment of a three channel design is given in FIG. 27B.

As will be known, microchannels can vary in the design layout, dimensions, geometries, materials, methods of fabrication, and chemical modifications. The device according to the present invention may, in certain embodiments, have a multiplexed design so that various combinations of selected biomarkers might be detected on a single device (e.g., a single multichannel card), thereby yielding a simultaneous readout from a single plasma/biofluid sample. A panel of biomarkers can therefore be detected on a single device that contains multiple microchannels. An example of such a multichannel card 30 is shown in FIG. 28. With reference now to FIG. 28, this design includes a single inlet 32 where a sample is introduced and a single outlet 34. From inlet 32, the main channel 36 branches into several three-channel designs 38. Each three-channel design 38 is used for biomarker detection as discussed above. This illustration demonstrates the appearance of an exemplary card designed to detect a panel of five biomarkers.

In one embodiment, a microchannel card 40 is designed to function in concert with a hand-held PoCT detector unit 42, together functioning as a diagnostic system 44. With reference now to FIG. 29A (perspective view) and FIG. 29B (top view), three dimensional schematics of the appearance of one embodiment of a hand-held diagnostic system 44 according to the present invention are shown. In these schematics, the microchannel card 40 is inserted (shown with arrow in FIG. 29B) into a receiving portion 41 of hand-held PoCT detector unit 42. A detector 46 (e.g., a photodetector) capable of operably engaging the microchannel card 40 would detect and quantify the amount of measurable signal (e.g., light) emitted from each channel 48 (e.g., reaction chamber) on the card 40. Printed circuit boards 50 may be used to transfer data to a display 52 as well as to complete calculations. Such a device can be powered by one or more local energy storage devices, such as lithium-ion, nickel-metal hydride, nickel-cadmium, lead acid, carbon zinc, alkaline, or zinc-air batteries. In one embodiment, the detector and display would be battery-powered, with a battery inserted in slot 54, and would be controlled by on/off toggle switch 56. In one embodiment, the detector unit 44 may be activated by operating a control means 58 (e.g., a "START" button). Detector unit may also include a housing 60.

One embodiment of a display 52 layout is shown in FIG. 29C. On this display, the biomarkers are separated into diagnostic and prognostic indicators. On the diagnostic side, results for each biomarker may be displayed in absolute numbers, as concentrations, and/or in terms of relative risk for a given pathology (in which case the absolute value or concentration would be interpreted in terms of the threshold values established for normal versus pathological conditions). An algorithm may be used to provide a single interpretive assessment for the risk of neural damage in that patient. For example, this could include indicator lights and/or text which would convey assessments of either "high risk," "moderate risk," or "low risk." Similarly, for prognostic biomarkers, values might be displayed in absolute numbers, as concentrations, and/or in terms of relative risk for the severity of, and outcome associated with, a given pathology (in which case the absolute value or concentration would be interpreted in terms of the threshold values corresponding to the prognosis). An algorithm might also be run to provide a single interpretive assessment for the prognosis of recovery from neural damage in that patient. In one embodiment, the assessment includes indicator lights and/or text which would convey assessments of either "serious," "guarded," or "good" prognosis.

It should be understood that the same detection modalities described herein could also be used to detect other biomarkers and/or diagnose genetic defects, other than the broad example of neural injury. For example, the enzymatic assay detection modality could be used to diagnose metabolic deficiencies that result in idiopathic hemolytic anemia and which stem from defects in one or more enzymes of glycolysis, a pathway producing energy from glucose (Martinov et al., "Deficiencies of Glycolytic Enzymes as a Possible Cause of Hemolytic Anemia," *Biochim. Biophys. Acta* 1474 (1):75-87 (2000), which is hereby incorporated by reference in its entirety). In that case, a red blood cell lysate would be the biological sample being investigated, and each channel would contain one or more tethered glycolytic enzymes. A luminescent output would correspond to ATP production, which would be maximal in a channel or tube in which a deficient enzyme were complemented.

EXAMPLES

Example 1—Tethered Enzymes Improve Cascading Assay Reaction Kinetics

Tethering one or more proteins involved in the reaction cascades to a scaffold can provide several advantages. First, it can confine either the detection reaction or the readout signal to a certain area of the diagnostic card. This would allow in-line background luminescence control readings and also reduce the size of the photodetector apparatus. In addition, tethering of enzymes has been shown to provide enhancement of enzyme stability (Liang et al., "Biomedical Application of Immobilized Enzymes," *J. Pharm. Sci.* 89(8): 979-90 (2000), which is hereby incorporated by reference in its entirety), and to improve reaction kinetics (FIGS. 30A-30B)) (see Mukai et al., "Sequential Reactions of Surface-Tethered Glycolytic Enzymes," *Chem. Biol.* 16(9):1013-20 (2009) and Blum et al., "Collagen Strip with Immobilized Luciferase for ATP Bioluminescent Determination," *Biotechnol. Bioeng.* 27(3):232-7 (1985), which are hereby incorporated by reference in their entirety).

FIGS. 30A and 30B show the significant increase in the coupled reaction efficiency between PK and Luc when immobilized onto NP's, compared to activity in solution or when only PK is tethered (FIGS. 30A and 30B show inset schematics representing the reaction set up for the corresponding results). As shown in FIG. 30B, tethering or immobilizing both PK and Luc on NPs increases the sensitivity of this assay to NSE.

Example 2—Assays According to the Present Invention Detect Neural Injury Biomarkers Each detection modality described supra was tested to determine that the coupled reactions described could indeed detect the presence of the biomarker in the complex environment of human serum. For these experiments, representative biomarkers we utilized from different detection modalities (enzymatic: NSE, PGM; oxidative: UA, glutamate, glucose; cleavage: GST; affector: S100β; BL cofactor: $Ca^{2+}$). These examples were chosen based on their reported relevance to neural injury (Whiteley et al., "Blood Biomarkers in the Diagnosis of Ischemic Stroke: A Systematic Review," Stroke 39(10):2902-9 (2008); Saenger and Christenson, "Stroke Biomarkers: Progress and Challenges for Diagnosis, Prognosis, Differentiation, and Treatment," Clin. Chem. 56(1):21-33 (2010); Whiteley et al., "Blood Markers for the Prognosis of Ischemic Stroke: A Systematic Review," Stroke 40(5):e380-9 (2009), which are hereby incorporated by reference in their entirety).

To test each modality, the biomarkers, substrates, and cofactors for each of the assays were purchased and the reactions performed in commercial human serum. Tests were carried out in a 96-well plate using multiple wells for each biomarker. Assays were run with both positive control and negative control wells. The negative control well included all reagents discussed previously minus the biomarker. The test wells included all the reagents and used commercial human serum spiked with increasing amounts of biomarker. Photons were collected using a luminescent plate reader. Results are shown in FIGS. 31A-31H. The horizontal axis shows the amount of biomarker spiked into human serum. The vertical axis shows the number of photons collected in luminescent units (LU). LUs were calculated by subtracting the negative control well from all the test wells to exclude background and non-specific luminescence. The signal increased as the amount of biomarker increased, illustrating a positive correlation. These data demonstrate the feasibility for each of the detection modalities.

Example 3—Detection of NSE, UA, Glutamate, and S100β

To demonstrate several detection modalities, an animal model for neural injury was used to generate samples that were then screened for a panel of four biomarkers (NSE, UA, glutamate and S100β). For these experiments, control and experimental rats were anesthetized and given craniectomies to allow access to the brain. A stroke was induced in the experimental rats by heat ligation/coagulation of a major blood vessel. Plasma samples were taken at various time points including −1 hr, 0 hr (stroke is induced), 1 hr, 2 hr, 3 hr, 4 hr and 6 hr for both the control and stroke rat. The control rat data demonstrated the impact of both the anesthesia and the surgical procedure itself on the biomarkers, confirming that any change in biomarker amounts detected did reflect neural damage due to the vessel occlusion and not other aspects of the surgical procedure or anesthesia. A total of 8 rats were included in this experiment. Results are shown in FIGS. 32A-32B, 33A-33B, 34A-34B, and 35. To detect NSE (FIGS. 32A-32B) both PK and firefly Luc were immobilized to MSPs via silica-binding tags. The reactions were again carried out in a 96-well plate. For each time point there was a negative control well (which included all reaction components excluding the NSE substrate 2PG) and a test well (with all the required components) (FIG. 32A). To demonstrate that the system was indeed detecting and quantifying NSE, aliquots of the samples taken at 6 hours were also run using an ELISA detection method. The results matched those of the ELISA detection method (FIG. 32B) showing that the methods were detecting NSE and with great improvements in speed. For example, the ELISA data showed here were obtained using a commercial kit (cat #DENL20 (R&D Systems, Inc., Minneapolis, Minn.)) that requires a 4 hour incubation, whereas the present data were integrated over a 10 minute reaction time period.

For the detection of UA (FIGS. 33A-33B), glucose (FIGS. 34A-34B), and S100β (FIG. 35), commercial enzymes were used as opposed to recombinant, therefore there was no tethering of enzymes to a scaffold. The data in these figures were normalized to the −1 hour time point, which represents the basal amounts of NSE present in the blood before the stroke was induced. Samples from the control rat did not show any significant increases as time progressed or any significant increase from time −1 hour. The experimental (stroke) rat showed a progressively increasing signal as time progressed, with significant increases from time −1 hour in all cases (P=0.05<*<0.1, 0.01<**<0.05). These results display the feasibility of using the enzymatic, oxidative and affector biomarker assay detection modalities to identify biomarkers in freshly drawn rat plasma.

Example 4—Tethered Enzymes are Stable in a Reaction Mix Over Time

For certain card/reader embodiments according to the present invention, it is advantageous for the components contained within the microchannels to be stable over time until used. To demonstrate such stability of tethered enzymes in a reaction mix over time, we lyophilized Luc tethered to MSP in a luciferase reaction mix (including luciferin, $Mg^{2+}$ and $K^+$). This lyophilized mixture was stored at −20° C. for 12 days, at which point the reaction mix was reconstituted and ATP was added to measure Luc activity. FIGS. 36A and 36B show the high activity observed (FIG. 36A), which was approximately 85% of the activity of that same mixture when tested fresh (FIG. 36B).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method for detecting the presence of a neural injury biomarker in a biological sample, the method comprising:
providing a biological sample;
providing a system, the system comprising: a platform comprising one or more channels, at least one channel of said one or more channels comprising: biological assay components suitable to detect the presence of a neural injury biomarker in the biological sample, wherein the neural injury biomarker is an enzyme selected from the group consisting of neuron specific enolase ("NSE"), phosphoglyceromutase ("PGM"), and nucleoside diphosphate kinase A ("NDK-A"), said components comprising: (i) one or more substrates of the neural injury biomarker and one or more co-factors; and (ii) one or more enzymes capable of acting upon the product of a reaction between the neural injury biomarker and the one or more substrates, wherein at least one enzyme is immobilized within the at least one channel on one or more supports and at least one enzyme is a signal-transducing molecule, said components positioned in the at least one channel to permit a sequential reaction;

subjecting the biological sample to an assay to detect the neural injury biomarker within the at least one channel of said one or more channels, whereby the neural injury biomarker, if present in the biological sample, will react with the one or more substrates causing a single reaction or a series of coupled reactions that cause production of a measurable signal by the signal-transducing molecule, wherein the measurable signal is selected from the group consisting of a photometrically detectable signal, an electrochemically detectable signal, a colorimetrically detectable signal, and a fluorescent signal; and detecting, based on said subjecting, the measurable signal, wherein the measurable signal indicates presence of the neural injury biomarker in the biological sample.

2. The method according to claim 1, wherein the signal-transducing molecule of the assay is selected from the group consisting of firefly luciferase, renilla luciferase, horseradish peroxidase, pyruvate oxidase, and a chromogen.

3. The method according to claim 1, wherein said one or more channels comprises at least two channels and wherein the at least two channels of said one or more channels each comprise said biological assay components.

4. The method according to claim 1, wherein the biological sample is provided from a subject.

5. The method according to claim 1, wherein the neural injury biomarker is NSE, the one or more substrates comprises 2-phosphoglycerate, and wherein the one or more enzymes comprises pyruvate kinase.

6. The method according to claim 5, wherein the signal transducing molecule is luciferase.

7. The method according to claim 6, said assay further comprising:
providing D-luciferin and $O_2$, wherein the D-luciferin and $O_2$ are contacted with the biological sample during said contacting to permit a sequential reaction, wherein the NSE, if present in the biological sample, will react with the 2-phosphoglycerate to produce PEP and ADP, with the PEP and ADP reacting with pyruvate kinase to produce pyruvate and ATP, said ATP reacting with luciferase to produce the measurable signal.

8. The method according to claim 1, wherein the neural injury biomarker is PGM, the one or more substrates comprises 3-phosphoglycerate, and the one or more enzymes comprises enolase and pyruvate kinase.

9. The method according to claim 8, wherein the signal transducing molecule is luciferase.

10. The method according to claim 9, said assay further comprising:
providing D-luciferin and $O_2$, wherein the D-luciferin and $O_2$ are contacted with the biological sample during said contacting to permit a sequential reaction, whereby the PGM, if present in the biological sample, will react with the 3-phosphoglycerate to produce 2-phosphoglycerate, the 2-phosphoglycerate reacting with enolase to produce PEP and ADP, with the PEP and ADP reacting with pyruvate kinase to produce pyruvate and ATP, said ATP reacting with luciferase to produce the measurable signal.

11. The method according to claim 1, wherein the neural injury biomarker is NDK-A, and wherein the one or more substrates comprises GTP and ADP.

12. The method according to claim 11, wherein the signal transducing molecule is luciferase.

13. The method according to claim 12, said assay further comprising:
providing D-luciferin and $O_2$, wherein the D-luciferin and $O_2$ are contacted with the biological sample during said contacting to permit a sequential reaction, whereby the NDK-A, if present in the biological sample, will react with GTP and ADP to produce GDP and ATP, said ATP reacting with luciferase to produce the measurable signal.

14. The method according to claim 4, wherein said method comprises quantifying, based on said detecting, the amount of the neural injury biomarker present in the biological sample.

15. The method according to claim 4, wherein the subject has a neural injury resulting from ischemic stroke, hemorrhagic stroke, trauma leading to concussion, trauma leading to contusion, or aneurism.

16. The method according to claim 4, wherein the method further comprises:
selecting a subject having neural injury.

17. The method according to claim 4, wherein the biological sample is a whole blood sample, blood serum sample, blood plasma sample, or a cerebrospinal fluid sample.

18. The method according to claim 4 further comprising:
selecting a subject that displays symptoms of a condition mediated by neural injury.

19. The method according to claim 3, wherein the method further comprises subjecting the biological sample to an assay to detect the neural injury biomarker within each of the at least two channels.

20. The method according to claim 1, wherein the system further comprises: at least one of the one or more channels that serves as a negative control.

21. The method according to claim 1, wherein the system further comprises: at least one of the one or more channels that serves as a positive control.

22. The method according to claim 1, wherein the system further comprises: a measurable signal detector.

23. The method according to claim 1, wherein the one or more supports comprises a nanoparticle.

24. The method according to claim 1, wherein the neural injury biomarker is neuron specific enolase.

25. The method according to claim 1, wherein the neural injury biomarker is phosphoglyceromutase.

26. The method according to claim 1, wherein the neural injury biomarker is nucleoside diphosphate kinase A.

27. The method according to claim 1, wherein the measurable signal is photometrically detectable.

28. The method according to claim 1, wherein the measurable signal is electrochemically detectable.

29. The method according to claim 1, wherein the measurable signal is colorimetrically detectable.

30. The method according to claim 1, wherein the measurable signal is fluorescent.

31. A method of treating a neural injury in a subject, said method comprising:

providing a biological sample from a subject having a neural injury resulting from ischemic stroke, hemorrhagic stroke, trauma leading to concussion, trauma leading to contusion, or aneurism;

providing a system, the system comprising: a platform comprising one or more channels, at least one channel of said one or more channels comprising: biological assay components suitable to detect the presence of a neural injury biomarker in the biological sample, wherein the neural injury biomarker is an enzyme selected from the group consisting of neuron specific enolase ("NSE"), phosphoglyceromutase ("PGM"), and nucleoside diphosphate kinase A ("NDK-A"), said components comprising: (i) one or more substrates of the neural injury biomarker and one or more co-factors; and (ii) one or more enzymes capable of acting upon the product of a reaction between the neural injury biomarker and the one or more substrates, wherein at least one enzyme is immobilized within the at least one channel on one or more supports and at least one enzyme is a signal-transducing molecule, said components positioned in the at least one channel to permit a sequential reaction;

subjecting the biological sample to an assay to detect the neural injury biomarker within the at least one channel of said one or more channels, whereby the neural injury biomarker, if present in the biological sample, will react with the one or more substrates causing a single reaction or a series of coupled reactions that cause production of a measurable signal by the signal-transducing molecule, wherein the measurable signal is selected from the group consisting of a photometrically detectable signal, an electrochemically detectable signal, a colorimetrically detectable signal, and a fluorescent signal;

detecting, based on said subjecting, the measurable signal, wherein the measurable signal indicates presence of the neural injury biomarker in the biological sample; and administering, based on said detecting, to the subject a treatment for the neural injury.

32. The method according to claim 31, wherein the neural injury results from ischemic stroke.

33. The method according to claim 32, wherein the treatment for the neural injury is tissue plasminogen activator.

34. The method according to claim 31, wherein the biological sample is a whole blood sample, blood serum sample, blood plasma sample, or a cerebrospinal fluid sample.

35. The method according to claim 31, wherein the system further comprises: at least one of the one or more channels that serves as a negative control.

36. The method according to claim 31, wherein the system further comprises: at least one of the one or more channels that serves as a positive control.

37. The method according to claim 31, wherein the system further comprises: a measurable signal detector.

38. The method according to claim 31, wherein the one or more supports comprises a nanoparticle.

39. The method according to claim 31, wherein the neural injury biomarker is neuron specific enolase.

40. The method according to claim 31, wherein the neural injury biomarker is phosphoglyceromutase.

41. The method according to claim 31, wherein the neural injury biomarker is nucleoside diphosphate kinase A.

42. The method according to claim 31, wherein the measurable signal is photometrically detectable.

43. The method according to claim 31, wherein the measurable signal is electrochemically detectable.

44. The method according to claim 31, wherein the measurable signal is colorimetrically detectable.

45. The method according to claim 31, wherein the measurable signal is fluorescent.

* * * * *